(12) United States Patent
Hobbs et al.

(10) Patent No.: US 6,821,750 B2
(45) Date of Patent: Nov. 23, 2004

(54) ABCG8 VECTORS, HOST CELLS, AND METHOD OF MAKING

(75) Inventors: Helen H. Hobbs, Dallas, TX (US); Bei Shan, Redwood City, CA (US); Robert Barnes, Frisco, TX (US); Hui Tian, Foster City, CA (US)

(73) Assignees: Tularik Inc., South San Francisco, CA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/989,981

(22) Filed: Nov. 20, 2001

(65) Prior Publication Data

US 2003/0049730 A1 Mar. 13, 2003

Related U.S. Application Data

(60) Provisional application No. 60/252,235, filed on Nov. 20, 2000, and provisional application No. 60/253,645, filed on Nov. 28, 2000.

(51) Int. Cl.$^7$ .................. C12N 15/85; C12N 15/86; C07K 5/00; C07K 14/00
(52) U.S. Cl. .............. 435/69.1; 435/252.3; 435/254.11; 435/320.1; 536/23.1; 536/23.5
(58) Field of Search ............................ 435/69.1, 252.3, 435/254.11, 320.1, 325; 536/23.1, 23.5; 530/300, 350; 514/2

(56) References Cited

FOREIGN PATENT DOCUMENTS

| WO | WO 01/15876 A2 | 3/2001 |
|---|---|---|
| WO | WO 01/40541 A1 | 6/2001 |
| WO | WO 02/27016 A2 | 4/2002 |

OTHER PUBLICATIONS

Beaty et al., *Am. J. Hum. Genet.*, 38:492–504 (1986).
Berge et al., *Science*, 290:1771–1775 (2000).
Bhattacharyya et al., *J. Clin. Invest.*, 53:1033–1043 (1974).
Bingham et al., *Cell* 25:693–704 (1981).
Ewart et al., *J. Biol. Chem.*, 269:10370–7 (1994).
Gould et al., *Metabolism*, 18(8):652–682 (1969).
Gregg et al., *J. Clin. Invest.*, 77:1864–1872 (1986).
Higgins, *Annu. Rev. Cell Biol.*, 8:67–113 (1992).
Hobbs et al., *Hum. Mutat.*, 1:445–466 (1992).
Ikeda et al., *Biophys. Res. Commun.*, 273:1063–1068 (2000).
Janowski et al., *Nature*, 383:728–731 (1996).
Janowski et al., *Proc. Natl. Acad. Sci. USA*, 96:266–271 (1999).
Jones et al., *Biochem.*, 33:3038–3049 (1994).
Klucken et al., *Proc. Natl. Acad. Sci. USA*, 97(2):817–822 (2000).
Kwiterovich, Jr., et al., *Lancet*, 1:466–469 (1981).
Lawn et al., *J. Clin. Invest.*, 104(8):25–31 (1999).
Le Saux et al., *Nat. Genet.*, 25:223–227 (2000).
Lu et al., *Am. J. Hum. Genel.*, 59:278–290 (2001).
Miettinen, Euro. J. Clin. Invest., 10:27–35 (1980).
Morganroth et al., *J. Pediatr.*, 85(5):639–643 (1974).
Nye et al., *N.Z. Med. J.*, 101:418–419 (1988).
Orita et al., *Genomics*, 5:874–879 (1989).
Patel et al., *J. Clin. Invest.*, 102(5):1041–1044 (1998).
Pollner et al., *FEBS Lett.*, 405:31–38 (1997).
Repa et al., *Science*, 289:1524–1529 (2000).
Russell et al., *Biochem.*, 31(20):4737–4749 (1992).
Salen et al., *J. Clin. Invest.*, 49:952–967 (1970).
Salen et al., *J. Lipid Res.*, 26:1126–1133 (1985).
Salen et al., *J. Lipid Res.*, 26:203–209 (1985).
Salen et al., *J. Lipid Res.*, 33:945–955 (1992).
Stell et al., *Top. Clin. Nutr.*, 5(2):63–66 (1990).
Sullivan et al., *J. Exp. Zool.*, 188:225–234 (1974).
Venkateswaran et al., *J. Biol. Chem.*, 275(19):14700–14707 (2000).
Walker et al., *Embo. J.*, 1(6):945–951 (1982).

*Primary Examiner*—Elizabeth Kemmerer
*Assistant Examiner*—Christopher James Nichols
(74) *Attorney, Agent, or Firm*—Townsend and Townsend and Crew LLP

(57) ABSTRACT

The present invention provides nucleic acids encoding a novel ABC family cholesterol transporter, ABCG8. The herein-disclosed sequences can be used for any of a number of purposes, including for the diagnosis and treatment of cholesterol-associated disorders, including sitosterolemia, and for the identification of molecules that associate with and/or modulate the activity of ABCG8.

35 Claims, 8 Drawing Sheets

FIG. 1C.

```
ABCG5  PNIVNSVVALISIAGVLVGSGFLRNIQEM-PIPFKIISYFTEQKYCSEILVVNEFYGLNFTCGSSNVSVT    595
ABCG8  FHMASFFSNALYNSFYLAG-GFMINLSSLWTVP-AWISKVSELRWCFEGLMKIQESRRTYKMPLGNLTIA    623

ABCG5  TNPMCAFTQGIQFIEKTCPGATSRFTMNFLLYSFIPALVILGIVVFKIRDHLISR--                 651
ABCG8  VS------GDKILSAMELDSYPLYAI-YLIVIGLSGGFMVLYYVSLRFIKQKPSQDW                 673
```

ABCG5 Putative Transmembrane Domain
ABCG8 Putative Transmembrane Domain

Walker A Hotif
Walker B Hotif
Signature C-Hotif

*FIG. 1C.* (CONTINUED)

A ABCG8 exon 2 (reverse strand) thru ABCG5 exon 2 (forward strand)

```
acCTGGTAGGTGAGATCTCTGACCTCCAGAGTGTTGGACTGACCACTGTAGGTGAAGTACAGACTGTTGTCACTTTCCGAGGAGA
ACAAGCTGTCCTGGAGGCCctgctgggagacatgtagtcaatgtgtaagggtcacatgtcagagagcgccttccccggttctcatt
tctttgttgtgaaccatcagatctctctccggtctctttgctttgaaagtaaatttattttattttgtgtgtatgact
gtttgcctgcatgcatgtgcgtgcgccacacatacctggcaccctcagaggtcaaaagaggtcactggtcctctgacctgg
agttatggtggttgtgaaccatctgtgtgtgatggaataatagcaatggcttaaactatggtcacccgctgtgcttcagaacactaga
cagctccattctctgatcttttactaaaaataatagcaatggcttaaactatggtcacccgctgtgcttcagaacactaga
atttatgtctcccatctcatttttgatgcccaggatctgactgtgtgtgtgtgtgtgtgtgtgttgggaatcaaatccatagt
aggaatatattggagatatctttttgggtgtgtgtgtgtgtgtgtgtgtgtgtgggtttctttgttttcaaatcaat
atcaaatatactaggccaatcatgatacttgacagaaccatagcaacacatccgggtctagacacttgtactgatacaaagttcttccattgg
tatctttaggagagatcttagttacttgcatggctaggaatttgttcctagacacttgtactgatacaaagttcttccattgg
cttcagagggtggagggctactgaggaggaaagctctcagttactgccagttagtgccagttcgcactcctgcgctaatgtgaagacctgggggggggttagaca
gacagagaggacagagtctgggttcccaggagcctcaacactgcaaactcagctgcaagcttctgaaaggaaaaaaatatctgtCTGGCTTG
tccacacggagagtctgggttcccaggagcctcaactcagctgcaactcagctgtcagaaggattcctgaaggattcctgcaacatcattgaatctgtgacaggtgacaccctaa
TGGATGACTTCTGTTCCATTTTAAAATATTTTCCTTGGCACCCAGAAGGATTCCTGAGGTTTGAATCTGTGACAGGTGACACCCTAA
AAACCCTTAAATAATCTATTCGGCTGAACTAGTGTGCCTGGGCTACAATGTAACGTCTCCTGTATTAACTTCTGGT
AAATTGAAAAGCGGGTTTTATTTGTAGGTAACATGGGAAATCCAGAGGGCACAAAAGGGAGAAATGTGCAGAAACAGTGGTGCCTG
gtgggacatatatgtaagctcttggcccaaggcacatacctggcctctgttgacccctctgttgacccatctctactctcatctgcctct
gcttagagtccaggctttcctatccctgtctgcagtgcgagcatggtgtagaccaggtcctgcgccgcctggtcactcagtgccag
aattccctgtgagatagccctgatctcctccttccaggccatgtagtgccggtctctgtgaagacctga
ctcgaatatgagtagaaagacgtgtgccagcagcagtccggccgctatgtgagttctttgtagagtgagatgctgggtggcagaggagatggat
ggcacggcatggagcagcagcagccagccagctccgcaagaaatgctcagtttctctaaatttgcatacagagatgagaggctgaaa
ccactgggcagtttttagcttgactgcggccatcgacagctttaagaacgaggcacaggcacagtcagtgtcattgtctccccccaccca
agccctgcagtgtcagtttagcttgacgagcccatcgacagctttaagaacgaggcacacaggcacatcagtgtcattgtctccccccaccca
aggcacacttttgaatatagaattctgacagctcattgcctttagctgctgtaatctgaaggcaaaagccccaccaccaact
```

FIG. 3.

```
gattttatatcctactcaggaaggagcatcaaagacgtagaaggagttatttcccatagacgtctgcctcatgggattctga
cagcagagttgcctgttgctgctgttggtagtaggattggtcaatctcaggcaatcctgtctctcccctagaacaggggactgaggcgtcc
ctgttgaatgtgccatcctggttctggtctttgtctccagaaaagtgggccggttgtagaagctgggggaggggagtcgtct
ttgctctgtcttcccatactcctgttctgcttcaaatcctgccacaactcgctgctctctgccactctgcctcctcccagaccataa
ggttaatgaggaggaggcctaggagctcccactcttgtccactctgccagtgtatttgtaaactgcctgaaaccaatgtg
gactgcaagcacacaattctgacgctcccaaacaagcgatcactcacagccagtgggaatggctcagttgtagaacacttggttca
tagccatagaaatattttcttgtaataagagaaaaaataatcgtgggctggggagaaggaagaaggaagaggagaaag
acctccctgttacacacagggggggattatgacctgacttccccagccctgagccctgcccttcagtgagttctctaagcagagcc
aggaaagtggccctcagaggagggattatgacctgacttccccagccctgagccctgcccttcagtgagttctctaagcagagcc
tcaactctacaaggtagcgagatgcctcaaccccctcctggcatttgttcctgacacctgccctttctctcttctctgtcta
ttggtctgtctgtcctgcagcttctcagcctcacacagagaccttaggcttcccccctgcttgttacctcccgctgtctcttgact
ccaaaccaatgccaaggactaacttactacataagtatggcaagctgtgatgcatcctgtgttgttacctccccgctgtctcttgact
accactgagatcttcttggtctgacagtcacatgggtcaacgctctgtgatgaatgtcatttgaaaacatcaatcccgtcattc
acaggagcgtgctgtcgtgggGAAGTGACCTCAGAGGTCTCCTGGCTCCTGAGACTGTTCCCCTCagacactcaacactgaggag
acagggccctgcctgcccgcccccattccattctacttgaagtccaggtggtacattaggactaatcctgtgtaggaagaaagtcag
tctgacactgcctccccccATGgaccagtgctgctgttttgtgtgccctttgtgtggcctctctctgttggctcttttgctcttagag
GTTTCTCAGCCATgaccagtgctgctgttttgtgtgccctttgtgtggcctctctctgttggctcttttgctcttagag
ctgggcacctgagccctgctgtgccagcctTTCTCCCAGCATTCCTYTCTGGCAAACACTTCCTATAAACACCGTGTGTT
CTGCCTATTGTCGAGATAAGGACACTCTGGCTAAAGGTACATCAGATAATGGCATCGTTGGCCAAattggtgaactgttatctca
cgaggattccaggGctggtaggatcggacaggcactccaccattggctcctcagttaaagctgccctggacgcaggccact
agaaaattcacttgcttcctgctagcCATGGGTGAGCTGAGTCCTGAGTCCAGAGGAGCCAGAGGGCCTCACATCA
ACAGAGGGTCTCTGAGCTCCCTGGAGCAAGTTCGGTCACGGCACAGAGGCTCGGCACAGCTTAGGTGTCCTGCATGTGTCCTA
CAGCGTCAGtaagggacctccacagcaaaaagctaggctctctgattgcctttctgaatggtgggtggcctgtgggctttt
gggttgtctgtccagcagatcaggtgaaagtgacagtctgtaacacagtgagtcgttcctcctcctcctgcgcagggca
gagcctgacattaaaacatgccctgaagccgcttgctgaagccgtgctgtctcactgatttctgctctccccttcttgactcgccac
cacctgtcctgtgtagatggagaaagcagtgtgcaggtgtaccatctcccagtcagagaccccagtaatcagagcagcaatgcag
ggttcactccaagaagaaagcagtgtgcaggtgtaccatctcccagtcagagaccccagtaatcagagcagctaatggaggcatg
ctccttggtggtggccaacttgtcattatacctccaaggacaacagagtgtacataaggctaaaacagagttgtcaacctgtc
```

FIG. 3. (CONTINUED)

```
cagggcaactgggatggggtagggctgggagcaggggtctggcacctctgcctttgccctttgtggattt
cctttaaagCAACCGTGTCGGCCCTTGGTGTGAACATCATGCCAGCAGAAGTGGACAGGCAAATCCTCAAAGATGTCTCC
TTGTACATCGAGAGTGGCCAGATTATGTGCATCTTAGGCAGCTCAGgtaagtgcctggggggscsggggctcctgtacttctaag
gcaggctctgggaggctttggctctcygtctaagcacaatgtttaagaagtragttcaaaagtgaggcagccatgcatttggc
atttgaatacaatctggtgacttgtctgctgtccaatagaaccctagtaccaaagtgaaatcttgaggaaatcctgaaagagt
ggaaagtcctgcctaacacgtaagtgcctctttgcttgtttgattgactgtgatgctagagagcaaaccagagcctggcat
gctcagtaaaccttctgccccagcacccagccccaaatgtatttcccctcctttcctttcttttcttttgtttc
tctcccttttctttctttctttcttcttctatatttctcactttgcattctgctcactgacctcctgttggtcttcctgtggagttcct
tttgtttgttgactgtggtgcaggggcctaggagagctaagagcccaggtcaagttgactctgtttgtcaggactaacttc
tcgaaggccccaattctacttctctttttcattatgatggtcatcagacacacagttgagaacagatacacctaaaaagacctcatgtt
tattcctgacctctactttgtctttttcattatgatggtcatcagacacacagttgagaacagatacacctaaaaagacctcatgtt
aatatagtctcaccgagcacacaccaggcttctcttttccaggtgagattttaaccttgactgtgactctcctgagggttcctcctctgccctgcaaaacctatagctgtaaattttcctatctg
gagccacctgtgtgtattccaactgtcattatcctgaggtgtcctcactattctcttccaggtgagattttaacctttgaatgtgactcatgtttgttt
gtcagcagctgggaggggtacactggcccagaagagaggctgggtagcatgccgcagtgttcgcaacactggttattctgaat
gcctctgcttaaggattctgacatattcgactcacagaccgttcttgactgagcagccccttgtaaactgtcagcatttaactgt
cccttgcttgtgctctcttagaaacaggcagtgtaaggctgtgggagagtgtggagagtcaggtatgacactgtttggtgtagctgagagt
gagtcccaa
```

The 4 exons are underlined and the conserved regions are in uppercase. The sequence ends in intron 2 of ABCG5 and is in the following order:

ABCG8    exon 2    (reverse strand)
ABCG8    intron 1  (reverse strand)
ABCG8    exon 1    (reverse strand)

FIG. 3. (CONTINUED)

Gap between genes

ABCG5    exon 1    (forward strand)
ABCG5    intron 1  (forward strand)
ABCG5    exon 2    (forward strand)
ABCG5    intron 2  (forward strand, partial)

B. Sequence Between ABCG5 and ABCG8 Containing the Control Sequences

Gaccagtgctgtttgtgccctttgtgtggcctccctgctgttgggctctctctgtctttgctcctagagctggggcacctgag
ccctcctctgtgccagcctTCTCCCAGCATTCCTYTCTGGCAAACACTTCCTATAAACACCGTGTGTTCTGCCTATTGTCGA
GATAAGGACACTCTGGCTAAAGGTACATCAGATAAATGGCATCGTTGGCCAAattggtgaactgttatctcacgagattccaggg
ctgggtaggatcggacaggcactcccattggctcctcagttaaagctgccctgagccggacaggccactagaaattcacttg
catttgcttcctgctagcc

SEQUENCE LISTING

<160> NUMBER OF SEQ ID NOS: 13

<210> SEQ ID NO 1
<211> LENGTH: 1959
<212> TYPE: DNA
<213> ORGANISM: Mus musculus
<220> FEATURE:
<221> NAME/KEY: CDS
<222> LOCATION: (1)..(1959)
<223> OTHER INFORMATION: mouse ABCG5 (mABCG5)

<400> SEQUENCE: 1

| | | | | | | | | | | | | | | | | |
|---|---|---|---|---|---|---|---|---|---|---|---|---|---|---|---|---|
| atg | ggt | gag | ctg | ccc | ttt | ctg | agt | cca | gag | gga | gcc | aga | ggg | cct | cac | 48 |
| Met | Gly | Glu | Leu | Pro | Phe | Leu | Ser | Pro | Glu | Gly | Ala | Arg | Gly | Pro | His | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| atc | aac | aga | ggg | tct | ctg | agc | tcc | ctg | gag | caa | ggt | tcg | gtc | acg | ggc | 96 |
| Ile | Asn | Arg | Gly | Ser | Leu | Ser | Ser | Leu | Glu | Gln | Gly | Ser | Val | Thr | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| aca | gag | gct | cgg | cac | agc | tta | ggt | gtc | ctg | cat | gtg | tcc | tac | agc | gtc | 144 |
| Thr | Glu | Ala | Arg | His | Ser | Leu | Gly | Val | Leu | His | Val | Ser | Tyr | Ser | Val | |
| | 35 | | | | | 40 | | | | | 45 | | | | | |

| | | | | | | | | | | | | | | | | |
|---|---|---|---|---|---|---|---|---|---|---|---|---|---|---|---|---|
| agc | aac | cgt | gtc | ggg | cct | tgg | tgg | aac | atc | aaa | tca | tgc | cag | cag | aag | 192 |
| Ser | Asn | Arg | Val | Gly | Pro | Trp | Trp | Asn | Ile | Lys | Ser | Cys | Gln | Gln | Lys | |
| 50 | | | | | 55 | | | | | 60 | | | | | | |

| | | | | | | | | | | | | | | | | |
|---|---|---|---|---|---|---|---|---|---|---|---|---|---|---|---|---|
| tgg | gac | agg | caa | atc | ctc | aaa | gat | gtc | tcc | ttg | tac | atc | gag | agt | ggc | 240 |
| Trp | Asp | Arg | Gln | Ile | Leu | Lys | Asp | Val | Ser | Leu | Tyr | Ile | Glu | Ser | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cag | att | atg | tgc | atc | tta | ggc | agc | tca | ggc | tca | ggg | aag | acc | acg | ctg | 288 |
| Gln | Ile | Met | Cys | Ile | Leu | Gly | Ser | Ser | Gly | Ser | Gly | Lys | Thr | Thr | Leu | |
| | | | 85 | | | | | 90 | | | | | 95 | | | |

| | | | | | | | | | | | | | | | | |
|---|---|---|---|---|---|---|---|---|---|---|---|---|---|---|---|---|
| ctg | gac | gcc | atc | tcc | ggg | agg | ctg | cgg | cgc | act | ggg | acc | ctg | gaa | ggg | 336 |
| Leu | Asp | Ala | Ile | Ser | Gly | Arg | Leu | Arg | Arg | Thr | Gly | Thr | Leu | Glu | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| gag | gtg | ttt | gtg | aat | ggc | tgc | gag | ctg | cgc | agg | gac | cag | ttc | caa | gac | 384 |
| Glu | Val | Phe | Val | Asn | Gly | Cys | Glu | Leu | Arg | Arg | Asp | Gln | Phe | Gln | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| tgc | ttc | tcc | tac | gtc | ctg | cag | agc | gac | gtt | ttt | ctg | agc | agc | ctc | act | 432 |
| Cys | Phe | Ser | Tyr | Val | Leu | Gln | Ser | Asp | Val | Phe | Leu | Ser | Ser | Leu | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| gtg | cgc | gag | acg | ttg | cga | tac | aca | gcg | atg | ctg | gcc | ctc | tgc | cgc | agc | 480 |
| Val | Arg | Glu | Thr | Leu | Arg | Tyr | Thr | Ala | Met | Leu | Ala | Leu | Cys | Arg | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tcc | gcg | gac | ttc | tac | aac | aag | aag | gta | gag | gca | gtc | atg | aca | gag | ctg | 528 |
| Ser | Ala | Asp | Phe | Tyr | Asn | Lys | Lys | Val | Glu | Ala | Val | Met | Thr | Glu | Leu | |
| | | | 165 | | | | | 170 | | | | | 175 | | | |

| | | | | | | | | | | | | | | | | |
|---|---|---|---|---|---|---|---|---|---|---|---|---|---|---|---|---|
| agc | ctg | agc | cac | gtg | gcg | gac | caa | atg | att | ggc | agc | tat | aat | ttt | ggg | 576 |
| Ser | Leu | Ser | His | Val | Ala | Asp | Gln | Met | Ile | Gly | Ser | Tyr | Asn | Phe | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| gga | att | tcc | agt | ggc | gag | cgg | cgc | cga | gtt | tcc | atc | gca | gcc | caa | ctc | 624 |
| Gly | Ile | Ser | Ser | Gly | Glu | Arg | Arg | Arg | Val | Ser | Ile | Ala | Ala | Gln | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| ctt | cag | gac | ccc | aag | gtc | atg | atg | cta | gat | gag | cca | acc | aca | gga | ctg | 672 |
| Leu | Gln | Asp | Pro | Lys | Val | Met | Met | Leu | Asp | Glu | Pro | Thr | Thr | Gly | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| gac | tgc | atg | act | gca | aat | caa | att | gtc | ctt | ctc | ttg | gct | gag | ctg | gct | 720 |
| Asp | Cys | Met | Thr | Ala | Asn | Gln | Ile | Val | Leu | Leu | Leu | Ala | Glu | Leu | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cgc | agg | gac | cga | att | gtg | att | gtc | acc | atc | cac | cag | cct | cgc | tct | gag | 768 |
| Arg | Arg | Asp | Arg | Ile | Val | Ile | Val | Thr | Ile | His | Gln | Pro | Arg | Ser | Glu | |
| | | | 245 | | | | | 250 | | | | | 255 | | | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctc | ttc | caa | cac | ttc | gac | aaa | att | gcc | atc | ctg | act | tac | gga | gag | ttg | 816  |
| Leu | Phe | Gln | His | Phe | Asp | Lys | Ile | Ala | Ile | Leu | Thr | Tyr | Gly | Glu | Leu |      |
|     |     |     | 260 |     |     |     | 265 |     |     |     |     | 270 |     |     |     |      |

| gtg | ttc | tgt | ggc | acc | cca | gag | gag | atg | ctt | ggc | ttc | ttc | aat | aac | tgt | 864 |
| Val | Phe | Cys | Gly | Thr | Pro | Glu | Glu | Met | Leu | Gly | Phe | Phe | Asn | Asn | Cys |     |
|     |     |     | 275 |     |     |     | 280 |     |     |     |     | 285 |     |     |     |     |

| ggt | tac | ccc | tgt | cct | gaa | cat | tcc | aat | ccc | ttt | gat | ttt | tac | atg | gac | 912 |
| Gly | Tyr | Pro | Cys | Pro | Glu | His | Ser | Asn | Pro | Phe | Asp | Phe | Tyr | Met | Asp |     |
|     | 290 |     |     |     |     | 295 |     |     |     |     | 300 |     |     |     |     |     |

| ttg | aca | tca | gtg | gac | acc | caa | agc | aga | gag | cgg | gaa | ata | gaa | acg | tac | 960 |
| Leu | Thr | Ser | Val | Asp | Thr | Gln | Ser | Arg | Glu | Arg | Glu | Ile | Glu | Thr | Tyr |     |
| 305 |     |     |     | 310 |     |     |     |     | 315 |     |     |     |     | 320 |     |     |

| aag | cga | gta | cag | atg | ctg | gaa | tgt | gcc | ttc | aag | gaa | tct | gac | atc | tat | 1008 |
| Lys | Arg | Val | Gln | Met | Leu | Glu | Cys | Ala | Phe | Lys | Glu | Ser | Asp | Ile | Tyr |      |
|     |     |     | 325 |     |     |     |     | 330 |     |     |     |     | 335 |     |     |      |

| cac | aaa | att | ctg | gag | aac | att | gaa | aga | gca | cga | tac | ctg | aaa | acc | tta | 1056 |
| His | Lys | Ile | Leu | Glu | Asn | Ile | Glu | Arg | Ala | Arg | Tyr | Leu | Lys | Thr | Leu |      |
|     |     |     | 340 |     |     |     | 345 |     |     |     |     | 350 |     |     |     |      |

| ccc | atg | gtt | cct | ttc | aaa | aca | aaa | gat | cct | cct | ggg | atg | ttc | ggc | aag | 1104 |
| Pro | Met | Val | Pro | Phe | Lys | Thr | Lys | Asp | Pro | Pro | Gly | Met | Phe | Gly | Lys |      |
|     |     |     | 355 |     |     |     | 360 |     |     |     |     | 365 |     |     |     |      |

| ctt | ggt | gtc | ctg | ctg | agg | cga | gta | aca | aga | aac | tta | atg | agg | aat | aag | 1152 |
| Leu | Gly | Val | Leu | Leu | Arg | Arg | Val | Thr | Arg | Asn | Leu | Met | Arg | Asn | Lys |      |
| 370 |     |     |     |     | 375 |     |     |     |     | 380 |     |     |     |     |     |      |

| cag | gca | gtg | att | atg | cgt | ctc | gtt | cag | aat | ctg | atc | atg | ggc | ctc | ttc | 1200 |
| Gln | Ala | Val | Ile | Met | Arg | Leu | Val | Gln | Asn | Leu | Ile | Met | Gly | Leu | Phe |      |
| 385 |     |     |     | 390 |     |     |     |     | 395 |     |     |     |     | 400 |     |      |

| ctc | att | ttc | tac | ctt | ctc | cgc | gtc | cag | aac | aac | acg | cta | aag | ggc | gct | 1248 |
| Leu | Ile | Phe | Tyr | Leu | Leu | Arg | Val | Gln | Asn | Asn | Thr | Leu | Lys | Gly | Ala |      |
|     |     |     |     | 405 |     |     |     |     | 410 |     |     |     |     | 415 |     |      |

| gtg | cag | gac | cgc | gtg | ggg | ctg | ctc | tat | cag | ctt | gtg | ggt | gcc | acc | cca | 1296 |
| Val | Gln | Asp | Arg | Val | Gly | Leu | Leu | Tyr | Gln | Leu | Val | Gly | Ala | Thr | Pro |      |
|     |     |     | 420 |     |     |     |     | 425 |     |     |     |     | 430 |     |     |      |

| tac | acc | ggc | atg | ctc | aat | gct | gtg | aat | ctg | ttt | ccc | atg | ctg | aga | gcc | 1344 |
| Tyr | Thr | Gly | Met | Leu | Asn | Ala | Val | Asn | Leu | Phe | Pro | Met | Leu | Arg | Ala |      |
|     |     | 435 |     |     |     |     | 440 |     |     |     |     | 445 |     |     |     |      |

| gtc | agc | gac | cag | gag | agt | cag | gat | ggc | ctg | tat | cat | aag | tgg | cag | atg | 1392 |
| Val | Ser | Asp | Gln | Glu | Ser | Gln | Asp | Gly | Leu | Tyr | His | Lys | Trp | Gln | Met |      |
| 450 |     |     |     |     | 455 |     |     |     |     | 460 |     |     |     |     |     |      |

| ctg | ctc | gcc | tac | gtg | cta | cac | gtc | ctc | ccc | ttc | agc | gtc | atc | gcc | acg | 1440 |
| Leu | Leu | Ala | Tyr | Val | Leu | His | Val | Leu | Pro | Phe | Ser | Val | Ile | Ala | Thr |      |
| 465 |     |     |     | 470 |     |     |     |     | 475 |     |     |     |     | 480 |     |      |

| gtc | att | ttc | agc | agt | gtg | tgt | tat | tgg | act | ctg | ggc | ttg | tat | cct | gaa | 1488 |
| Val | Ile | Phe | Ser | Ser | Val | Cys | Tyr | Trp | Thr | Leu | Gly | Leu | Tyr | Pro | Glu |      |
|     |     |     |     | 485 |     |     |     |     | 490 |     |     |     |     | 495 |     |      |

| gtt | gcc | aga | ttt | gga | tat | ttc | tct | gct | gct | ctt | ttg | gcc | cct | cac | tta | 1536 |
| Val | Ala | Arg | Phe | Gly | Tyr | Phe | Ser | Ala | Ala | Leu | Leu | Ala | Pro | His | Leu |      |
|     |     |     | 500 |     |     |     |     | 505 |     |     |     |     | 510 |     |     |      |

| att | gga | gaa | ttt | cta | aca | ctt | gtg | ctg | ctt | ggt | ata | gtc | caa | aac | cct | 1584 |
| Ile | Gly | Glu | Phe | Leu | Thr | Leu | Val | Leu | Leu | Gly | Ile | Val | Gln | Asn | Pro |      |
|     |     | 515 |     |     |     |     | 520 |     |     |     |     | 525 |     |     |     |      |

| aat | att | gtc | aac | agt | ata | gtg | gct | ctg | ctc | agc | atc | tct | ggg | ctg | ctt | 1632 |
| Asn | Ile | Val | Asn | Ser | Ile | Val | Ala | Leu | Leu | Ser | Ile | Ser | Gly | Leu | Leu |      |
| 530 |     |     |     |     | 535 |     |     |     |     | 540 |     |     |     |     |     |      |

| att | gga | tct | gga | ttt | atc | aga | aac | ata | caa | gaa | atg | ccc | att | cct | tta | 1680 |
| Ile | Gly | Ser | Gly | Phe | Ile | Arg | Asn | Ile | Gln | Glu | Met | Pro | Ile | Pro | Leu |      |
| 545 |     |     |     | 550 |     |     |     |     | 555 |     |     |     |     | 560 |     |      |

| aaa | atc | ctg | ggt | tat | ttt | aca | ttc | caa | aaa | tac | tgt | tgt | gag | att | ctc | 1728 |
| Lys | Ile | Leu | Gly | Tyr | Phe | Thr | Phe | Gln | Lys | Tyr | Cys | Cys | Glu | Ile | Leu |      |

-continued

```
                565                 570                 575
gtg gtc aat gag ttt tac ggc ctg aac ttc act tgt ggt gga tcc aac    1776
Val Val Asn Glu Phe Tyr Gly Leu Asn Phe Thr Cys Gly Gly Ser Asn
            580                 585                 590 acc tct atg cta aat cac ccg atg tgc gcc atc acc caa ggg gtc cag    1824
Thr Ser Met Leu Asn His Pro Met Cys Ala Ile Thr Gln Gly Val Gln
        595                 600                 605 ttc atc gag aaa acc tgc cca ggt gct aca tcc aga ttc acg gca aac    1872
Phe Ile Glu Lys Thr Cys Pro Gly Ala Thr Ser Arg Phe Thr Ala Asn
    610                 615                 620 ttc ctc atc tta tat ggg ttt atc cca gct ctg gtc atc cta gga ata    1920
Phe Leu Ile Leu Tyr Gly Phe Ile Pro Ala Leu Val Ile Leu Gly Ile
625                 630                 635                 640 gtg att ttt aaa gtc agg gac tac ctg att agc aga tag                1959
Val Ile Phe Lys Val Arg Asp Tyr Leu Ile Ser Arg
                645                 650
```

<210> SEQ ID NO 2
<211> LENGTH: 652
<212> TYPE: PRT
<213> ORGANISM: Mus musculus
<220> FEATURE:
<223> OTHER INFORMATION: mouse ABCG5 (mABCG5)

<400> SEQUENCE: 2

```
Met Gly Glu Leu Pro Phe Leu Ser Pro Glu Gly Ala Arg Gly Pro His
 1               5                  10                  15

Ile Asn Arg Gly Ser Leu Ser Ser Leu Glu Gln Gly Ser Val Thr Gly
            20                  25                  30

Thr Glu Ala Arg His Ser Leu Gly Val Leu His Val Ser Tyr Ser Val
        35                  40                  45

Ser Asn Arg Val Gly Pro Trp Trp Asn Ile Lys Ser Cys Gln Gln Lys
    50                  55                  60

Trp Asp Arg Gln Ile Leu Lys Asp Val Ser Leu Tyr Ile Glu Ser Gly
65                  70                  75                  80

Gln Ile Met Cys Ile Leu Gly Ser Ser Gly Ser Gly Lys Thr Thr Leu
                85                  90                  95

Leu Asp Ala Ile Ser Gly Arg Leu Arg Arg Thr Gly Thr Leu Glu Gly
            100                 105                 110

Glu Val Phe Val Asn Gly Cys Glu Leu Arg Arg Asp Gln Phe Gln Asp
        115                 120                 125

Cys Phe Ser Tyr Val Leu Gln Ser Asp Val Phe Leu Ser Ser Leu Thr
    130                 135                 140

Val Arg Glu Thr Leu Arg Tyr Thr Ala Met Leu Ala Leu Cys Arg Ser
145                 150                 155                 160

Ser Ala Asp Phe Tyr Asn Lys Lys Val Glu Ala Val Met Thr Glu Leu
                165                 170                 175

Ser Leu Ser His Val Ala Asp Gln Met Ile Gly Ser Tyr Asn Phe Gly
            180                 185                 190

Gly Ile Ser Ser Gly Glu Arg Arg Val Ser Ile Ala Ala Gln Leu
        195                 200                 205

Leu Gln Asp Pro Lys Val Met Met Leu Asp Glu Pro Thr Thr Gly Leu
    210                 215                 220

Asp Cys Met Thr Ala Asn Gln Ile Val Leu Leu Ala Glu Leu Ala
225                 230                 235                 240

Arg Arg Asp Arg Ile Val Ile Val Thr Ile His Gln Pro Arg Ser Glu
                245                 250                 255
```

```
Leu Phe Gln His Phe Asp Lys Ile Ala Ile Leu Thr Tyr Gly Glu Leu
            260                 265                 270

Val Phe Cys Gly Thr Pro Glu Glu Met Leu Gly Phe Phe Asn Asn Cys
            275                 280                 285

Gly Tyr Pro Cys Pro Glu His Ser Asn Pro Phe Asp Phe Tyr Met Asp
            290                 295                 300

Leu Thr Ser Val Asp Thr Gln Ser Arg Glu Arg Glu Ile Glu Thr Tyr
305                 310                 315                 320

Lys Arg Val Gln Met Leu Glu Cys Ala Phe Lys Glu Ser Asp Ile Tyr
            325                 330                 335

His Lys Ile Leu Glu Asn Ile Glu Arg Ala Arg Tyr Leu Lys Thr Leu
            340                 345                 350

Pro Met Val Pro Phe Lys Thr Lys Asp Pro Pro Gly Met Phe Gly Lys
            355                 360                 365

Leu Gly Val Leu Leu Arg Arg Val Thr Arg Asn Leu Met Arg Asn Lys
            370                 375                 380

Gln Ala Val Ile Met Arg Leu Val Gln Asn Leu Ile Met Gly Leu Phe
385                 390                 395                 400

Leu Ile Phe Tyr Leu Leu Arg Val Gln Asn Asn Thr Leu Lys Gly Ala
                405                 410                 415

Val Gln Asp Arg Val Gly Leu Leu Tyr Gln Leu Val Gly Ala Thr Pro
            420                 425                 430

Tyr Thr Gly Met Leu Asn Ala Val Asn Leu Phe Pro Met Leu Arg Ala
            435                 440                 445

Val Ser Asp Gln Glu Ser Gln Asp Gly Leu Tyr His Lys Trp Gln Met
            450                 455                 460

Leu Leu Ala Tyr Val Leu His Val Leu Pro Phe Ser Val Ile Ala Thr
465                 470                 475                 480

Val Ile Phe Ser Ser Val Cys Tyr Trp Thr Leu Gly Leu Tyr Pro Glu
                485                 490                 495

Val Ala Arg Phe Gly Tyr Phe Ser Ala Ala Leu Leu Ala Pro His Leu
            500                 505                 510

Ile Gly Glu Phe Leu Thr Leu Val Leu Leu Gly Ile Val Gln Asn Pro
            515                 520                 525

Asn Ile Val Asn Ser Ile Val Ala Leu Leu Ser Ile Ser Gly Leu Leu
            530                 535                 540

Ile Gly Ser Gly Phe Ile Arg Asn Ile Gln Glu Met Pro Ile Pro Leu
545                 550                 555                 560

Lys Ile Leu Gly Tyr Phe Thr Phe Gln Lys Tyr Cys Cys Glu Ile Leu
                565                 570                 575

Val Val Asn Glu Phe Tyr Gly Leu Asn Phe Thr Cys Gly Gly Ser Asn
            580                 585                 590

Thr Ser Met Leu Asn His Pro Met Cys Ala Ile Thr Gln Gly Val Gln
            595                 600                 605

Phe Ile Glu Lys Thr Cys Pro Gly Ala Thr Ser Arg Phe Thr Ala Asn
610                 615                 620

Phe Leu Ile Leu Tyr Gly Phe Ile Pro Ala Leu Val Ile Leu Gly Ile
625                 630                 635                 640

Val Ile Phe Lys Val Arg Asp Tyr Leu Ile Ser Arg
                645                 650
```

<210> SEQ ID NO 3
<211> LENGTH: 2019

-continued

```
<212> TYPE: DNA
<213> ORGANISM: Mus musculus
<220> FEATURE:
<221> NAME/KEY: CDS
<222> LOCATION: (1)..(2019)
<223> OTHER INFORMATION: mouse ABCG8 (mABCG8)

<400> SEQUENCE: 3 atg gct gag aaa acc aaa gaa gag acc cag ctg tgg aat ggg act gta        48
Met Ala Glu Lys Thr Lys Glu Glu Thr Gln Leu Trp Asn Gly Thr Val
  1               5                  10                  15 ctt cag gat gct tcg ggc ctc cag gac agc ttg ttc tcc tcg gaa agt        96
Leu Gln Asp Ala Ser Gly Leu Gln Asp Ser Leu Phe Ser Ser Glu Ser
             20                  25                  30 gac aac agt ctg tac ttc acc tac agt ggt cag tcc aac act ctg gag       144
Asp Asn Ser Leu Tyr Phe Thr Tyr Ser Gly Gln Ser Asn Thr Leu Glu
         35                  40                  45 gtc aga gat ctc acc tac cag gtg gac atc gcc tct cag gtg cct tgg       192
Val Arg Asp Leu Thr Tyr Gln Val Asp Ile Ala Ser Gln Val Pro Trp
     50                  55                  60 ttt gag cag ctg gct cag ttc aag ata ccc tgg agg tct cat agc agc       240
Phe Glu Gln Leu Ala Gln Phe Lys Ile Pro Trp Arg Ser His Ser Ser
 65                  70                  75                  80 caa gac tcc tgt gag ctg ggc atc cga aat cta agc ttc aaa gtg agg       288
Gln Asp Ser Cys Glu Leu Gly Ile Arg Asn Leu Ser Phe Lys Val Arg
                 85                  90                  95 agt gga cag atg ctg gcc atc ata ggg agc tca ggc tgc ggg aga gcc       336
Ser Gly Gln Met Leu Ala Ile Ile Gly Ser Ser Gly Cys Gly Arg Ala
            100                 105                 110 tca cta ctc gac gtg atc aca ggc aga ggc cac ggt ggc aag atg aaa       384
Ser Leu Leu Asp Val Ile Thr Gly Arg Gly His Gly Gly Lys Met Lys
        115                 120                 125 tca gga caa att tgg ata aat ggg caa ccc agt acg cct cag ctg gtg       432
Ser Gly Gln Ile Trp Ile Asn Gly Gln Pro Ser Thr Pro Gln Leu Val
    130                 135                 140 agg aag tgc gtt gcg cat gtg cgg cag cat gac caa ctg ctg ccc aac       480
Arg Lys Cys Val Ala His Val Arg Gln His Asp Gln Leu Leu Pro Asn
145                 150                 155                 160 ctg acc gtc aga gag acc ctg gct ttc att gcc cag atg cgc ctg ccc       528
Leu Thr Val Arg Glu Thr Leu Ala Phe Ile Ala Gln Met Arg Leu Pro
                165                 170                 175 agg acc ttc tcc cag gcc cag cgt gac aaa cgg gtg gaa gac gta atc       576
Arg Thr Phe Ser Gln Ala Gln Arg Asp Lys Arg Val Glu Asp Val Ile
            180                 185                 190 gcc gag ctg cgg ctg cgg cag tgc gcc aac acc aga gtg ggc aac acg       624
Ala Glu Leu Arg Leu Arg Gln Cys Ala Asn Thr Arg Val Gly Asn Thr
        195                 200                 205 tat gta cgt ggg gtg tcc ggg ggt gag cgc cga cga gtg agc att ggg       672
Tyr Val Arg Gly Val Ser Gly Gly Glu Arg Arg Arg Val Ser Ile Gly
    210                 215                 220 gtg cag ctc ctg tgg aac cca gga atc ctc att ctg gat gaa ccc act       720
Val Gln Leu Leu Trp Asn Pro Gly Ile Leu Ile Leu Asp Glu Pro Thr
225                 230                 235                 240 tct ggc ctc gac agc ttc aca gcc cac aat ctg gtg aca acc ttg tcc       768
Ser Gly Leu Asp Ser Phe Thr Ala His Asn Leu Val Thr Thr Leu Ser
                245                 250                 255 cgc ctg gcc aag ggc aac agg ctg gtg ctc atc tcc ctc cac cag cct       816
Arg Leu Ala Lys Gly Asn Arg Leu Val Leu Ile Ser Leu His Gln Pro
            260                 265                 270 cgc tct gac atc ttc agg cta ttt gac ctg gtc ctt ctg atg aca tct       864
Arg Ser Asp Ile Phe Arg Leu Phe Asp Leu Val Leu Leu Met Thr Ser
```

|  |  |
|---|---|
| ggc acc cct atc tac ctg ggg gcg gcg cag caa atg gtg cag tac ttc<br>Gly Thr Pro Ile Tyr Leu Gly Ala Ala Gln Gln Met Val Gln Tyr Phe<br>290                295              300 | 912 |
| aca tcc att ggc cac cct tgt cct cgc tat agc aac cct gcg gac ttc<br>Thr Ser Ile Gly His Pro Cys Pro Arg Tyr Ser Asn Pro Ala Asp Phe<br>305              310              315              320 | 960 |
| tac gtg gac ttg acc agc atc gac aga cgc agc aaa gaa cgg gag gtg<br>Tyr Val Asp Leu Thr Ser Ile Asp Arg Arg Ser Lys Glu Arg Glu Val<br>325            330              335 | 1008 |
| gcc acc gtg gag aag gca cag tct ctt gca gcc ctg ttc cta gaa aaa<br>Ala Thr Val Glu Lys Ala Gln Ser Leu Ala Ala Leu Phe Leu Glu Lys<br>340                345              350 | 1056 |
| gta caa ggc ttt gat gac ttt ctg tgg aaa gct gag gca aag gaa ctc<br>Val Gln Gly Phe Asp Asp Phe Leu Trp Lys Ala Glu Ala Lys Glu Leu<br>355            360              365 | 1104 |
| aac aca agc acc cac aca gtc agc ctg acc ctc aca cag gac act gac<br>Asn Thr Ser Thr His Thr Val Ser Leu Thr Leu Thr Gln Asp Thr Asp<br>370                375              380 | 1152 |
| tgt ggg act gct gtt gag ctg ccc ggg atg ata gag cag ttt tcc acc<br>Cys Gly Thr Ala Val Glu Leu Pro Gly Met Ile Glu Gln Phe Ser Thr<br>385            390              395              400 | 1200 |
| ctg atc cgt cgt cag att tcc aat gac ttc cgg gac ctg ccc acg ctg<br>Leu Ile Arg Arg Gln Ile Ser Asn Asp Phe Arg Asp Leu Pro Thr Leu<br>405            410              415 | 1248 |
| ctc att cat ggg tcg gaa gcc tgc ctg atg tcc ctc atc att ggc ttc<br>Leu Ile His Gly Ser Glu Ala Cys Leu Met Ser Leu Ile Ile Gly Phe<br>420            425              430 | 1296 |
| ctt tac tac ggc cat ggg gcc aag cag ctc tcc ttc atg gac aca gca<br>Leu Tyr Tyr Gly His Gly Ala Lys Gln Leu Ser Phe Met Asp Thr Ala<br>435            440              445 | 1344 |
| gcc ctc ctc ttc atg ata ggg gcg ctc att cct ttc aat gtc atc ctg<br>Ala Leu Leu Phe Met Ile Gly Ala Leu Ile Pro Phe Asn Val Ile Leu<br>450            455              460 | 1392 |
| gat gtc gtc tcc aaa tgt cac tcg gag agg tca atg ctg tac tat gag<br>Asp Val Val Ser Lys Cys His Ser Glu Arg Ser Met Leu Tyr Tyr Glu<br>465            470              475              480 | 1440 |
| ctg gaa gac ggg ctg tac act gct ggt cct tat ttc ttt gcc aag atc<br>Leu Glu Asp Gly Leu Tyr Thr Ala Gly Pro Tyr Phe Phe Ala Lys Ile<br>485            490              495 | 1488 |
| cta gga gaa ttg ccg gag cac tgt gcc tac gtc atc tac gcg atg<br>Leu Gly Glu Leu Pro Glu His Cys Ala Tyr Val Ile Ile Tyr Ala Met<br>500            505              510 | 1536 |
| ccc atc tac tgg ctg aca aac ctg cgg ccc gtg cct gag ctc ttc ctt<br>Pro Ile Tyr Trp Leu Thr Asn Leu Arg Pro Val Pro Glu Leu Phe Leu<br>515            520              525 | 1584 |
| cta cac ttc ctg ctc gtg tgg ttg gtg gtc ttc tgc tgc agg acc atg<br>Leu His Phe Leu Leu Val Trp Leu Val Val Phe Cys Cys Arg Thr Met<br>530            535              540 | 1632 |
| gcc ctg gct gcc tct gcc atg ctg ccc acc ttc cac atg tcc tcc ttc<br>Ala Leu Ala Ala Ser Ala Met Leu Pro Thr Phe His Met Ser Ser Phe<br>545            550              555              560 | 1680 |
| ttc tgc aat gcc ctc tac aac tcc ttc tac ctt act gcc ggc ttc atg<br>Phe Cys Asn Ala Leu Tyr Asn Ser Phe Tyr Leu Thr Ala Gly Phe Met<br>565            570              575 | 1728 |
| ata aac ttg gac aac ctg tgg ata gtg cct gca tgg atc tcc aag ctg<br>Ile Asn Leu Asp Asn Leu Trp Ile Val Pro Ala Trp Ile Ser Lys Leu<br>580            585              590 | 1776 |
| tcg ttc ctc cgg tgg tgc ttc tcg ggg ctg atg cag att caa ttt aat | 1824 |

```
                                                              -continued

Ser Phe Leu Arg Trp Cys Phe Ser Gly Leu Met Gln Ile Gln Phe Asn
        595                 600                 605 gga cac ctt tac acc aca caa atc ggc aac ttc acc ttc tcc atc ctc        1872
Gly His Leu Tyr Thr Thr Gln Ile Gly Asn Phe Thr Phe Ser Ile Leu
    610                 615                 620 gga gac acg atg atc agt gcc atg gac ctg aac tcg cat cca ctc tat        1920
Gly Asp Thr Met Ile Ser Ala Met Asp Leu Asn Ser His Pro Leu Tyr
625                 630                 635                 640 gcg atc tac ctc att gtc atc ggc atc agc tac ggc ttc ctg ttc ctg        1968
Ala Ile Tyr Leu Ile Val Ile Gly Ile Ser Tyr Gly Phe Leu Phe Leu
                645                 650                 655 tac tat cta tcc ttg aag ctc atc aaa cag aag tca att caa gac tgg        2016
Tyr Tyr Leu Ser Leu Lys Leu Ile Lys Gln Lys Ser Ile Gln Asp Trp
            660                 665                 670 tga                                                                     2019

<210> SEQ ID NO 4
<211> LENGTH: 672
<212> TYPE: PRT
<213> ORGANISM: Mus musculus
<220> FEATURE:
<223> OTHER INFORMATION: mouse ABCG8 (mABCG8)

<400> SEQUENCE: 4

Met Ala Glu Lys Thr Lys Glu Glu Thr Gln Leu Trp Asn Gly Thr Val
 1               5                  10                  15

Leu Gln Asp Ala Ser Gly Leu Gln Asp Ser Leu Phe Ser Ser Glu Ser
            20                  25                  30

Asp Asn Ser Leu Tyr Phe Thr Tyr Ser Gly Gln Ser Asn Thr Leu Glu
        35                  40                  45

Val Arg Asp Leu Thr Tyr Gln Val Asp Ile Ala Ser Gln Val Pro Trp
    50                  55                  60

Phe Glu Gln Leu Ala Gln Phe Lys Ile Pro Trp Arg Ser His Ser Ser
65                  70                  75                  80

Gln Asp Ser Cys Glu Leu Gly Ile Arg Asn Leu Ser Phe Lys Val Arg
                85                  90                  95

Ser Gly Gln Met Leu Ala Ile Ile Gly Ser Ser Gly Cys Gly Arg Ala
            100                 105                 110

Ser Leu Leu Asp Val Ile Thr Gly Arg Gly His Gly Lys Met Lys
        115                 120                 125

Ser Gly Gln Ile Trp Ile Asn Gly Gln Pro Ser Thr Pro Gln Leu Val
    130                 135                 140

Arg Lys Cys Val Ala His Val Arg Gln His Asp Gln Leu Leu Pro Asn
145                 150                 155                 160

Leu Thr Val Arg Glu Thr Leu Ala Phe Ile Ala Gln Met Arg Leu Pro
                165                 170                 175

Arg Thr Phe Ser Gln Ala Gln Arg Asp Lys Arg Val Glu Asp Val Ile
            180                 185                 190

Ala Glu Leu Arg Leu Arg Gln Cys Ala Asn Thr Arg Val Gly Asn Thr
        195                 200                 205

Tyr Val Arg Gly Val Ser Gly Gly Glu Arg Arg Arg Val Ser Ile Gly
    210                 215                 220

Val Gln Leu Leu Trp Asn Pro Gly Ile Leu Ile Leu Asp Glu Pro Thr
225                 230                 235                 240

Ser Gly Leu Asp Ser Phe Thr Ala His Asn Leu Val Thr Thr Leu Ser
                245                 250                 255
```

-continued

```
Arg Leu Ala Lys Gly Asn Arg Leu Val Leu Ile Ser Leu His Gln Pro
            260                 265                 270
Arg Ser Asp Ile Phe Arg Leu Phe Asp Leu Val Leu Leu Met Thr Ser
        275                 280                 285
Gly Thr Pro Ile Tyr Leu Gly Ala Ala Gln Gln Met Val Gln Tyr Phe
    290                 295                 300
Thr Ser Ile Gly His Pro Cys Pro Arg Tyr Ser Asn Pro Ala Asp Phe
305                 310                 315                 320
Tyr Val Asp Leu Thr Ser Ile Asp Arg Ser Lys Glu Arg Glu Val
                325                 330                 335
Ala Thr Val Glu Lys Ala Gln Ser Leu Ala Ala Leu Phe Leu Glu Lys
            340                 345                 350
Val Gln Gly Phe Asp Asp Phe Leu Trp Lys Ala Glu Ala Lys Glu Leu
        355                 360                 365
Asn Thr Ser Thr His Thr Val Ser Leu Thr Leu Thr Gln Asp Thr Asp
    370                 375                 380
Cys Gly Thr Ala Val Glu Leu Pro Gly Met Ile Glu Gln Phe Ser Thr
385                 390                 395                 400
Leu Ile Arg Arg Gln Ile Ser Asn Asp Phe Arg Asp Leu Pro Thr Leu
                405                 410                 415
Leu Ile His Gly Ser Glu Ala Cys Leu Met Ser Leu Ile Ile Gly Phe
            420                 425                 430
Leu Tyr Tyr Gly His Gly Ala Lys Gln Leu Ser Phe Met Asp Thr Ala
        435                 440                 445
Ala Leu Leu Phe Met Ile Gly Ala Leu Ile Pro Phe Asn Val Ile Leu
    450                 455                 460
Asp Val Val Ser Lys Cys His Ser Glu Arg Ser Met Leu Tyr Tyr Glu
465                 470                 475                 480
Leu Glu Asp Gly Leu Tyr Thr Ala Gly Pro Tyr Phe Phe Ala Lys Ile
                485                 490                 495
Leu Gly Glu Leu Pro Glu His Cys Ala Tyr Val Ile Ile Tyr Ala Met
            500                 505                 510
Pro Ile Tyr Trp Leu Thr Asn Leu Arg Pro Val Pro Glu Leu Phe Leu
        515                 520                 525
Leu His Phe Leu Leu Val Trp Leu Val Val Phe Cys Cys Arg Thr Met
    530                 535                 540
Ala Leu Ala Ala Ser Ala Met Leu Pro Thr Phe His Met Ser Ser Phe
545                 550                 555                 560
Phe Cys Asn Ala Leu Tyr Asn Ser Phe Tyr Leu Thr Ala Gly Phe Met
                565                 570                 575
Ile Asn Leu Asp Asn Leu Trp Ile Val Pro Ala Trp Ile Ser Lys Leu
            580                 585                 590
Ser Phe Leu Arg Trp Cys Phe Ser Gly Leu Met Gln Ile Gln Phe Asn
        595                 600                 605
Gly His Leu Tyr Thr Thr Gln Ile Gly Asn Phe Thr Phe Ser Ile Leu
    610                 615                 620
Gly Asp Thr Met Ile Ser Ala Met Asp Leu Asn Ser His Pro Leu Tyr
625                 630                 635                 640
Ala Ile Tyr Leu Ile Val Ile Gly Ile Ser Tyr Gly Phe Leu Phe Leu
                645                 650                 655
Tyr Tyr Leu Ser Leu Lys Leu Ile Lys Gln Lys Ser Ile Gln Asp Trp
            660                 665                 670
```

```
<210> SEQ ID NO 5
<211> LENGTH: 2340
<212> TYPE: DNA
<213> ORGANISM: Homo sapiens
<220> FEATURE:
<221> NAME/KEY: CDS
<222> LOCATION: (107)..(2062)
<223> OTHER INFORMATION: human ABCG5 (hABCG5)

<400> SEQUENCE: 5
gtcaggtgga gcaggcaggg cagtctgcca cgggctcccc aactgaagcc actctgggga      60
gggtccggcc accagaaaat tgcccagct  ttgctgcctg ttggcc atg ggt gac        115
                                                Met Gly Asp
                                                  1 ctc tca tct ttg acc ccc gga ggg tcc atg ggt ctc caa gta aac aga       163
Leu Ser Ser Leu Thr Pro Gly Gly Ser Met Gly Leu Gln Val Asn Arg
      5                  10                  15 ggc tcc cag agc tcc ctg gag ggg gct cct gcc acc gcc ccg gag cct       211
Gly Ser Gln Ser Ser Leu Glu Gly Ala Pro Ala Thr Ala Pro Glu Pro
 20                  25                  30                  35 cac agc ctg ggc atc ctc cat gcc tcc tac agc gtc agc cac cgc gtg       259
His Ser Leu Gly Ile Leu His Ala Ser Tyr Ser Val Ser His Arg Val
                 40                  45                  50 agg ccc tgg tgg gac atc aca tct tgc cgg cag cag tgg acc agg cag       307
Arg Pro Trp Trp Asp Ile Thr Ser Cys Arg Gln Gln Trp Thr Arg Gln
             55                  60                  65 atc ctc aaa gat gtc tcc ttg tac gtg gag agc ggg cag atc atg tgc       355
Ile Leu Lys Asp Val Ser Leu Tyr Val Glu Ser Gly Gln Ile Met Cys
         70                  75                  80 atc cta gga agc tca ggc tcc ggg aaa acc acg ctg ctg gac gcc atg       403
Ile Leu Gly Ser Ser Gly Ser Gly Lys Thr Thr Leu Leu Asp Ala Met
     85                  90                  95 tcc ggg agg ctg ggg cgc gcg ggg acc ttc ctg ggg gag gtg tat gtg       451
Ser Gly Arg Leu Gly Arg Ala Gly Thr Phe Leu Gly Glu Val Tyr Val
100                 105                 110                 115 aac ggc cgg gcg ctg cgc cgg gag cag ttc cag gac tgc ttc tcc tac       499
Asn Gly Arg Ala Leu Arg Arg Glu Gln Phe Gln Asp Cys Phe Ser Tyr
                120                 125                 130 gtc ctg cag agc gac acc ctg ctg agc agc ctc acc gtg cgc gag acg       547
Val Leu Gln Ser Asp Thr Leu Leu Ser Ser Leu Thr Val Arg Glu Thr
            135                 140                 145 ctg cac tac acc gcg ctg ctg gcc atc cgc cgc ggc aat ccc ggc tcc       595
Leu His Tyr Thr Ala Leu Leu Ala Ile Arg Arg Gly Asn Pro Gly Ser
        150                 155                 160 ttc cag aag aag gtg gag gcc gtc atg gca gag ctg agt ctg agc cat       643
Phe Gln Lys Lys Val Glu Ala Val Met Ala Glu Leu Ser Leu Ser His
    165                 170                 175 gtg gca gac cga ctg att ggc aac tac agc ttg ggg ggc att tcc acg       691
Val Ala Asp Arg Leu Ile Gly Asn Tyr Ser Leu Gly Gly Ile Ser Thr
180                 185                 190                 195 ggt gag cgg cgc cgg gtc tcc atc gca gcc cag ctg ctc cag gat cct       739
Gly Glu Arg Arg Arg Val Ser Ile Ala Ala Gln Leu Leu Gln Asp Pro
                200                 205                 210 aag gtc atg ctg ttt gat gag cca acc aca ggc ctg gac tgc atg act       787
Lys Val Met Leu Phe Asp Glu Pro Thr Thr Gly Leu Asp Cys Met Thr
            215                 220                 225 gct aat cag att gtc gtc ctc ctg gtg gaa ctg gct cgc agg aac cga       835
Ala Asn Gln Ile Val Val Leu Leu Val Glu Leu Ala Arg Arg Asn Arg
        230                 235                 240 att gtg gtt ctc acc att cac cag ccc cgt tct gag ctt ttt cag ctc       883
Ile Val Val Leu Thr Ile His Gln Pro Arg Ser Glu Leu Phe Gln Leu
```

```
                245                250                255
ttt gac aaa att gcc atc ctg agc ttc gga gag ctg att ttc tgt ggc    931
Phe Asp Lys Ile Ala Ile Leu Ser Phe Gly Glu Leu Ile Phe Cys Gly
260                265                270                275 acg cca gcg gaa atg ctt gat ttc ttc aat gac tgc ggt tac cct tgt    979
Thr Pro Ala Glu Met Leu Asp Phe Phe Asn Asp Cys Gly Tyr Pro Cys
                280                285                290 cct gaa cat tca aac cct ttt gac ttc tat atg gac ctg acg tca gtg   1027
Pro Glu His Ser Asn Pro Phe Asp Phe Tyr Met Asp Leu Thr Ser Val
            295                300                305 gat acc caa agc aag gaa cgg gaa ata gaa acc tcc aag aga gtc cag   1075
Asp Thr Gln Ser Lys Glu Arg Glu Ile Glu Thr Ser Lys Arg Val Gln
        310                315                320 atg ata gaa tct gcc tac aag aaa tca gca att tgt cat aaa act ttg   1123
Met Ile Glu Ser Ala Tyr Lys Lys Ser Ala Ile Cys His Lys Thr Leu
    325                330                335 aag aat att gaa aga atg aaa cac ctg aaa acg tta cca atg gtt cct   1171
Lys Asn Ile Glu Arg Met Lys His Leu Lys Thr Leu Pro Met Val Pro
340                345                350                355 ttc aaa acc aaa gat tct cct gga gtt ttc tct aaa ctg ggt gtt ctc   1219
Phe Lys Thr Lys Asp Ser Pro Gly Val Phe Ser Lys Leu Gly Val Leu
                360                365                370 ctg agg aga gtg aca aga aac ttg gtg aga aat aag ctg gca gtg att   1267
Leu Arg Arg Val Thr Arg Asn Leu Val Arg Asn Lys Leu Ala Val Ile
                375                380                385 acg cgt ctc ctt cag aat ctg atc atg ggt ttg ttc ctc ctt ttc ttc   1315
Thr Arg Leu Leu Gln Asn Leu Ile Met Gly Leu Phe Leu Leu Phe Phe
            390                395                400 gtt ctg cgg gtc cga agc aat gtg cta aag ggt gct atc cag gac cgc   1363
Val Leu Arg Val Arg Ser Asn Val Leu Lys Gly Ala Ile Gln Asp Arg
        405                410                415 gta ggt ctc ctt tac cag ttt gtg ggc gcc acc ccg tac aca ggc atg   1411
Val Gly Leu Leu Tyr Gln Phe Val Gly Ala Thr Pro Tyr Thr Gly Met
420                425                430                435 ctg aac gct gtg aat ctg ttt ccc gtg ctg cga gct gtc agc gac cag   1459
Leu Asn Ala Val Asn Leu Phe Pro Val Leu Arg Ala Val Ser Asp Gln
                440                445                450 gag agt cag gac ggc ctc tac cag aag tgg cag atg atg ctg gcc tat   1507
Glu Ser Gln Asp Gly Leu Tyr Gln Lys Trp Gln Met Met Leu Ala Tyr
                455                460                465 gca ctg cac gtc ctc ccc ttc agc gtt gtt gcc acc atg att ttc agc   1555
Ala Leu His Val Leu Pro Phe Ser Val Val Ala Thr Met Ile Phe Ser
            470                475                480 agt gtg tgc tac tgg acg ctg ggc tta cat cct gag gtt gcc cga ttt   1603
Ser Val Cys Tyr Trp Thr Leu Gly Leu His Pro Glu Val Ala Arg Phe
        485                490                495 gga tat ttt tct gct gct ctc ttg gcc ccc cac tta att ggt gaa ttt   1651
Gly Tyr Phe Ser Ala Ala Leu Leu Ala Pro His Leu Ile Gly Glu Phe
500                505                510                515 cta act ctt gtg cta ctt ggt atc gtc caa aat cca ata tca aac       1699
Leu Thr Leu Val Leu Leu Gly Ile Val Gln Asn Pro Asn Ile Val Asn
                520                525                530 agt gta gtg gct ctg ctg tcc att gcg ggg gtg ctt gtt gga tct gga   1747
Ser Val Val Ala Leu Leu Ser Ile Ala Gly Val Leu Val Gly Ser Gly
                535                540                545 ttc ctc aga aac ata caa gaa atg ccc att cct ttt aaa atc atc agt   1795
Phe Leu Arg Asn Ile Gln Glu Met Pro Ile Pro Phe Lys Ile Ile Ser
            550                555                560 tat ttt aca ttc caa aaa tat tgc agt gag att ctt gta gtc aat gag   1843
```

-continued

| | | |
|---|---|---|
| Tyr Phe Thr Phe Gln Lys Tyr Cys Ser Glu Ile Leu Val Val Asn Glu<br>565 570 575 | | |
| ttc tac gga ctg aat ttc act tgt ggc agc tca aat gtt tct gtg aca<br>Phe Tyr Gly Leu Asn Phe Thr Cys Gly Ser Ser Asn Val Ser Val Thr<br>580 585 590 595 | 1891 | |
| act aat cca atg tgt gcc ttc act caa gga att caa ttc att gag aaa<br>Thr Asn Pro Met Cys Ala Phe Thr Gln Gly Ile Gln Phe Ile Glu Lys<br>600 605 610 | 1939 | |
| acc tgc cca ggt gca aca tct aga ttc aca atg aac ttt ctg att ttg<br>Thr Cys Pro Gly Ala Thr Ser Arg Phe Thr Met Asn Phe Leu Ile Leu<br>615 620 625 | 1987 | |
| tat tca ttt att cca gct ctt gtc atc cta gga ata gtt gtt ttc aaa<br>Tyr Ser Phe Ile Pro Ala Leu Val Ile Leu Gly Ile Val Val Phe Lys<br>630 635 640 | 2035 | |
| ata agg gat cat ctc att agc agg tag tgaaagccat ggctgggaaa<br>Ile Arg Asp His Leu Ile Ser Arg<br>645 650 | 2082 | |
| atggaagtga agctgccgac tgtgcatgac tgctctgaac gtctgaaatg agagtgccat | 2142 | |
| gtatttcttt cttgacagga catctcaagt cttttaacca ttaagactcc atttgtgcct | 2202 | |
| cttggatcca agcaggcctt gaatgcaatg gaagtggttt atagtccctt gctcttacaa | 2262 | |
| cttgcaggga catgtggtta tttggaaatt gtgactgagc ggacccaaga atgtaaataa | 2322 | |
| tattcataaa cctatggg | 2340 | |

<210> SEQ ID NO 6
<211> LENGTH: 651
<212> TYPE: PRT
<213> ORGANISM: Homo sapiens
<220> FEATURE:
<223> OTHER INFORMATION: human ABCG5 (hABCG5)

<400> SEQUENCE: 6

Met Gly Asp Leu Ser Ser Leu Thr Pro Gly Gly Ser Met Gly Leu Gln
1               5                   10                  15

Val Asn Arg Gly Ser Gln Ser Ser Leu Glu Gly Ala Pro Ala Thr Ala
                20                  25                  30

Pro Glu Pro His Ser Leu Gly Ile Leu His Ala Ser Tyr Ser Val Ser
        35                  40                  45

His Arg Val Arg Pro Trp Trp Asp Ile Thr Ser Cys Arg Gln Gln Trp
    50                  55                  60

Thr Arg Gln Ile Leu Lys Asp Val Ser Leu Tyr Val Glu Ser Gly Gln
65                  70                  75                  80

Ile Met Cys Ile Leu Gly Ser Ser Gly Ser Gly Lys Thr Thr Leu Leu
                85                  90                  95

Asp Ala Met Ser Gly Arg Leu Gly Arg Ala Gly Thr Phe Leu Gly Glu
                100                 105                 110

Val Tyr Val Asn Gly Arg Ala Leu Arg Arg Glu Gln Phe Gln Asp Cys
            115                 120                 125

Phe Ser Tyr Val Leu Gln Ser Asp Thr Leu Leu Ser Ser Leu Thr Val
        130                 135                 140

Arg Glu Thr Leu His Tyr Thr Ala Leu Leu Ala Ile Arg Arg Gly Asn
145                 150                 155                 160

Pro Gly Ser Phe Gln Lys Lys Val Glu Ala Val Met Ala Glu Leu Ser
                165                 170                 175

Leu Ser His Val Ala Asp Arg Leu Ile Gly Asn Tyr Ser Leu Gly Gly
            180                 185                 190

-continued

Ile Ser Thr Gly Glu Arg Arg Val Ser Ile Ala Ala Gln Leu Leu
        195                 200                 205

Gln Asp Pro Lys Val Met Leu Phe Asp Glu Pro Thr Thr Gly Leu Asp
    210                 215                 220

Cys Met Thr Ala Asn Gln Ile Val Val Leu Leu Val Glu Leu Ala Arg
225                 230                 235                 240

Arg Asn Arg Ile Val Val Leu Thr Ile His Gln Pro Arg Ser Glu Leu
                245                 250                 255

Phe Gln Leu Phe Asp Lys Ile Ala Ile Leu Ser Phe Gly Glu Leu Ile
            260                 265                 270

Phe Cys Gly Thr Pro Ala Glu Met Leu Asp Phe Phe Asn Asp Cys Gly
        275                 280                 285

Tyr Pro Cys Pro Glu His Ser Asn Pro Phe Asp Phe Tyr Met Asp Leu
    290                 295                 300

Thr Ser Val Asp Thr Gln Ser Lys Glu Arg Glu Ile Glu Thr Ser Lys
305                 310                 315                 320

Arg Val Gln Met Ile Glu Ser Ala Tyr Lys Lys Ser Ala Ile Cys His
                325                 330                 335

Lys Thr Leu Lys Asn Ile Glu Arg Met Lys His Leu Lys Thr Leu Pro
            340                 345                 350

Met Val Pro Phe Lys Thr Lys Asp Ser Pro Gly Val Phe Ser Lys Leu
        355                 360                 365

Gly Val Leu Leu Arg Arg Val Thr Arg Asn Leu Val Arg Asn Lys Leu
    370                 375                 380

Ala Val Ile Thr Arg Leu Leu Gln Asn Leu Ile Met Gly Leu Phe Leu
385                 390                 395                 400

Leu Phe Phe Val Leu Arg Val Arg Ser Asn Val Leu Lys Gly Ala Ile
                405                 410                 415

Gln Asp Arg Val Gly Leu Leu Tyr Gln Phe Val Gly Ala Thr Pro Tyr
            420                 425                 430

Thr Gly Met Leu Asn Ala Val Asn Leu Phe Pro Val Leu Arg Ala Val
        435                 440                 445

Ser Asp Gln Glu Ser Gln Asp Gly Leu Tyr Gln Lys Trp Gln Met Met
    450                 455                 460

Leu Ala Tyr Ala Leu His Val Leu Pro Phe Ser Val Val Ala Thr Met
465                 470                 475                 480

Ile Phe Ser Ser Val Cys Tyr Trp Thr Leu Gly Leu His Pro Glu Val
                485                 490                 495

Ala Arg Phe Gly Tyr Phe Ser Ala Ala Leu Leu Ala Pro His Leu Ile
            500                 505                 510

Gly Glu Phe Leu Thr Leu Val Leu Leu Gly Ile Val Gln Asn Pro Asn
        515                 520                 525

Ile Val Asn Ser Val Val Ala Leu Leu Ser Ile Ala Gly Val Leu Val
    530                 535                 540

Gly Ser Gly Phe Leu Arg Asn Ile Gln Glu Met Pro Ile Pro Phe Lys
545                 550                 555                 560

Ile Ile Ser Tyr Phe Thr Phe Gln Lys Tyr Cys Ser Glu Ile Leu Val
                565                 570                 575

Val Asn Glu Phe Tyr Gly Leu Asn Phe Thr Cys Gly Ser Ser Asn Val
            580                 585                 590

Ser Val Thr Thr Asn Pro Met Cys Ala Phe Thr Gln Gly Ile Gln Phe
        595                 600                 605

Ile Glu Lys Thr Cys Pro Gly Ala Thr Ser Arg Phe Thr Met Asn Phe

```
                    610                 615                  620
Leu Ile Leu Tyr Ser Phe Ile Pro Ala Leu Val Ile Leu Gly Ile Val
625                 630                  635                 640

Val Phe Lys Ile Arg Asp His Leu Ile Ser Arg
                645                 650

<210> SEQ ID NO 7
<211> LENGTH: 2669
<212> TYPE: DNA
<213> ORGANISM: Homo sapiens
<220> FEATURE:
<221> NAME/KEY: CDS
<222> LOCATION: (100)..(2121)
<223> OTHER INFORMATION: human ABCG8 (hABCG8)

<400> SEQUENCE: 7
gtgtccctgc tccaggaaac agagtgaaga cactggccct ggcaggcagc agctgggtct    60
aagagagctg cagcccaggg tcacagacct gtgggcccc atg gcc ggg aag gcg      114
                                            Met Ala Gly Lys Ala
                                              1               5 gca gag gag aga ggg ctg ccg aaa ggg gcc act ccc cag gat acc tcg     162
Ala Glu Glu Arg Gly Leu Pro Lys Gly Ala Thr Pro Gln Asp Thr Ser
             10                  15                  20 ggc ctc cag gat aga ttg ttc tcc tct gaa agt gac aac agc ctg tac    210
Gly Leu Gln Asp Arg Leu Phe Ser Ser Glu Ser Asp Asn Ser Leu Tyr
         25                  30                  35 ttc acc tac agt ggc cag ccc aac acc ctg gag gtc aga gac ctc aac   258
Phe Thr Tyr Ser Gly Gln Pro Asn Thr Leu Glu Val Arg Asp Leu Asn
     40                  45                  50 tac cag gtg gac ctg gcc tct cag gtc cct tgg ttt gag cag ctg gct   306
Tyr Gln Val Asp Leu Ala Ser Gln Val Pro Trp Phe Glu Gln Leu Ala
 55                  60                  65 cag ttc aag atg ccc tgg aca tct ccc agc tgc cag aat tct tgt gag   354
Gln Phe Lys Met Pro Trp Thr Ser Pro Ser Cys Gln Asn Ser Cys Glu
 70                  75                  80                  85 ctg ggc atc cag aac cta agc ttc aaa gtg aga agt ggg cag atg ctg   402
Leu Gly Ile Gln Asn Leu Ser Phe Lys Val Arg Ser Gly Gln Met Leu
                 90                  95                 100 gcc atc ata ggg agc tca ggt tgt ggg aga gcc tcc ttg cta gat gtg   450
Ala Ile Ile Gly Ser Ser Gly Cys Gly Arg Ala Ser Leu Leu Asp Val
            105                 110                 115 atc act ggc cga ggt cac ggc ggc aag atc aag tca ggc cag atc tgg   498
Ile Thr Gly Arg Gly His Gly Gly Lys Ile Lys Ser Gly Gln Ile Trp
        120                 125                 130 atc aat ggg cag ccc agc tcg cct cag ctg gtg agg aag tgt gtg gcc   546
Ile Asn Gly Gln Pro Ser Ser Pro Gln Leu Val Arg Lys Cys Val Ala
    135                 140                 145 cac gtg cgc cag cac aac cag ctg ctc ccc aac ttg act gtg cga gag   594
His Val Arg Gln His Asn Gln Leu Leu Pro Asn Leu Thr Val Arg Glu
150                 155                 160                 165 acc ttg gcc ttc att gcc cag atg cgg ctg ccc aga acc ttc tcc cag   642
Thr Leu Ala Phe Ile Ala Gln Met Arg Leu Pro Arg Thr Phe Ser Gln
                170                 175                 180 gcc cag cgt gac aaa agg gtg gag gac gtg atc gcg gag ctg cgg ctt   690
Ala Gln Arg Asp Lys Arg Val Glu Asp Val Ile Ala Glu Leu Arg Leu
            185                 190                 195 agg cag tgc gct gac acc cgc gtg ggc aac atg tac gtg cgg ggg ttg   738
Arg Gln Cys Ala Asp Thr Arg Val Gly Asn Met Tyr Val Arg Gly Leu
        200                 205                 210 tcg ggg ggt gag cgc agg aga gtc agc att ggg gtg cag ctc ctg tgg   786
```

-continued

```
Ser Gly Gly Glu Arg Arg Val Ser Ile Gly Val Gln Leu Leu Trp
215                 220                 225 aac cca gga atc ctt att ctc gac gaa ccc acc tct ggg ctc gac agc     834
Asn Pro Gly Ile Leu Ile Leu Asp Glu Pro Thr Ser Gly Leu Asp Ser
230                 235                 240                 245 ttc aca gcc cac aac ctg gtg aag acc ttg tcc agg ctg gcc aaa ggc     882
Phe Thr Ala His Asn Leu Val Lys Thr Leu Ser Arg Leu Ala Lys Gly
                250                 255                 260 aac cgg ctg gtg ctc atc tcc ctc cac cag cct cgc tct gac atc ttc     930
Asn Arg Leu Val Leu Ile Ser Leu His Gln Pro Arg Ser Asp Ile Phe
            265                 270                 275 agg ctg ttt gat ctg gtc ctc ctg atg acg tct ggc acc ccc atc tac     978
Arg Leu Phe Asp Leu Val Leu Leu Met Thr Ser Gly Thr Pro Ile Tyr
        280                 285                 290 tta ggg gcg gcc cag cac atg gtc cag tat ttc aca gcc atc ggc tac    1026
Leu Gly Ala Ala Gln His Met Val Gln Tyr Phe Thr Ala Ile Gly Tyr
    295                 300                 305 ccc tgt cct cgc tac agc aat cct gct gac ttc tat gtg gac ctg acc    1074
Pro Cys Pro Arg Tyr Ser Asn Pro Ala Asp Phe Tyr Val Asp Leu Thr
310                 315                 320                 325 agc att gac agg cgc agc aga gag cag gaa ttg gcc acc agg gag aag    1122
Ser Ile Asp Arg Arg Ser Arg Glu Gln Glu Leu Ala Thr Arg Glu Lys
                330                 335                 340 gct cag tca ctc gca gcc ctg ttt cta gaa aaa gtg cgt gac tta gat    1170
Ala Gln Ser Leu Ala Ala Leu Phe Leu Glu Lys Val Arg Asp Leu Asp
            345                 350                 355 gac ttt cta tgg aaa gca gag acg aag gat ctt gac gag gac acc tgt    1218
Asp Phe Leu Trp Lys Ala Glu Thr Lys Asp Leu Asp Glu Asp Thr Cys
        360                 365                 370 gtg gaa agc agc gtg acc cca cta gac acc aac tgc ctc ccg agt cct    1266
Val Glu Ser Ser Val Thr Pro Leu Asp Thr Asn Cys Leu Pro Ser Pro
    375                 380                 385 acg aag atg cct ggg gcg gtg cag cag ttt acg acg ctg atc cgt cgt    1314
Thr Lys Met Pro Gly Ala Val Gln Gln Phe Thr Thr Leu Ile Arg Arg
390                 395                 400                 405 cag att tcc aac gac ttc cga gac ctg ccc acc ctc ctc atc cat ggg    1362
Gln Ile Ser Asn Asp Phe Arg Asp Leu Pro Thr Leu Leu Ile His Gly
                410                 415                 420 gcg gag gcc tgt ctg atg tca atg acc atc ggc ttc ctc tat ttt ggc    1410
Ala Glu Ala Cys Leu Met Ser Met Thr Ile Gly Phe Leu Tyr Phe Gly
            425                 430                 435 cat ggg agc atc cag ctc tcc ttc atg gat aca gcc gcc ctc ttg ttc    1458
His Gly Ser Ile Gln Leu Ser Phe Met Asp Thr Ala Ala Leu Leu Phe
        440                 445                 450 atg atc ggt gct ctc atc cct ttc aac gtc att ctg gat gtc atc tcc    1506
Met Ile Gly Ala Leu Ile Pro Phe Asn Val Ile Leu Asp Val Ile Ser
    455                 460                 465 aaa tgt tac tca gag agg gca atg ctt tac tat gaa ctg gaa gac ggg    1554
Lys Cys Tyr Ser Glu Arg Ala Met Leu Tyr Tyr Glu Leu Glu Asp Gly
470                 475                 480                 485 ctg tac acc act ggt cca tat ttc ttt gcc aag atc ctc ggg gag ctt    1602
Leu Tyr Thr Thr Gly Pro Tyr Phe Phe Ala Lys Ile Leu Gly Glu Leu
                490                 495                 500 ccg gag cac tgt gcc tac atc atc atc tac ggg atg ccc acc tac tgg    1650
Pro Glu His Cys Ala Tyr Ile Ile Ile Tyr Gly Met Pro Thr Tyr Trp
            505                 510                 515 ctg gcc aac ctg agg cca ggc ctc cag ccc ttc ctg ctg cac ttc ctg    1698
Leu Ala Asn Leu Arg Pro Gly Leu Gln Pro Phe Leu Leu His Phe Leu
        520                 525                 530
```

-continued

| | | |
|---|---|---|
| ctg gtg tgg ctg gtg gtc ttc tgt tgc agg att atg gcc ctg gcc gcc<br>Leu Val Trp Leu Val Val Phe Cys Cys Arg Ile Met Ala Leu Ala Ala<br>535                       540                       545 | 1746 |
| gcg gcc ctg ctc ccc acc ttc cac atg gcc tcc ttc ttc agc aat gcc<br>Ala Ala Leu Leu Pro Thr Phe His Met Ala Ser Phe Phe Ser Asn Ala<br>550                       555                       560                    565 | 1794 |
| ctc tac aac tcc ttc tac ctc gcc ggg ggc ttc atg ata aac ttg agc<br>Leu Tyr Asn Ser Phe Tyr Leu Ala Gly Gly Phe Met Ile Asn Leu Ser<br>                   570                       575                       580 | 1842 |
| agc ctg tgg aca gtg ccc gcg tgg att tcc aaa gtg tcc ttc ctg cgg<br>Ser Leu Trp Thr Val Pro Ala Trp Ile Ser Lys Val Ser Phe Leu Arg<br>585                       590                       595 | 1890 |
| tgg tgt ttt gaa ggg ctg atg aag att cag ttc agc aga aga act tat<br>Trp Cys Phe Glu Gly Leu Met Lys Ile Gln Phe Ser Arg Arg Thr Tyr<br>                   600                       605                       610 | 1938 |
| aaa atg cct ctc ggg aac ctc acc atc gcg gtc tca gga gat aaa atc<br>Lys Met Pro Leu Gly Asn Leu Thr Ile Ala Val Ser Gly Asp Lys Ile<br>615                       620                       625 | 1986 |
| ctc agt gcc atg gag ctg gac tcg tac cct ctc tac gcc atc tac ctc<br>Leu Ser Ala Met Glu Leu Asp Ser Tyr Pro Leu Tyr Ala Ile Tyr Leu<br>630                       635                       640                    645 | 2034 |
| atc gtc att ggc ctc agc ggt ggc ttc atg gtc ctg tac tac gtg tcc<br>Ile Val Ile Gly Leu Ser Gly Gly Phe Met Val Leu Tyr Tyr Val Ser<br>                   650                       655                    660 | 2082 |
| tta agg ttc atc aaa cag aaa cca agt caa gac tgg tga ttcacgccag<br>Leu Arg Phe Ile Lys Gln Lys Pro Ser Gln Asp Trp<br>                   665                       670 | 2131 |
| acgtctgccc gctggtgggg gacctgagca gacccttcaa ctgcactccc tcctcaggag | 2191 |
| cccccttcctg gggacagtga ggacaatgac cctacagatg ctcagctaca tccggcccag | 2251 |
| ggtgctgcag tggcacagac cagccacagg atggcagtag aataaagaca gtcgaaaggg | 2311 |
| atttctgctc actggcagga gactgcgatg actgggagaa aacctgcact cggtggcacc | 2371 |
| tacaacgttg ctaatttatt ccttttgat atgcatttat ataggcaact cgatatagga | 2431 |
| tgggagcaaa ctaggaatga attgggtagc tagactgtgc aggaattgtt ggaacctgga | 2491 |
| gggaacaata acagtagcta gcagatttgg cttcatcttc caggggcccc acactccgtg | 2551 |
| gtgagccacc atcaatacag aaagtgacct aagatgtacc agcaagatgc catcccttct | 2611 |
| ttttgtgtgg ggtcatgggc tccaaaagcc aacgtgaaca attaaaaatg tattgagc | 2669 |

<210> SEQ ID NO 8
<211> LENGTH: 673
<212> TYPE: PRT
<213> ORGANISM: Homo sapiens
<220> FEATURE:
<223> OTHER INFORMATION: human ABCG8 (hABCG8)

<400> SEQUENCE: 8

Met Ala Gly Lys Ala Ala Glu Glu Arg Gly Leu Pro Lys Gly Ala Thr
1                 5                   10                 15

Pro Gln Asp Thr Ser Gly Leu Gln Asp Arg Leu Phe Ser Ser Glu Ser
                   20                   25                 30

Asp Asn Ser Leu Tyr Phe Thr Tyr Ser Gly Gln Pro Asn Thr Leu Glu
             35                   40                  45

Val Arg Asp Leu Asn Tyr Gln Val Asp Leu Ala Ser Gln Val Pro Trp
50                   55                   60

Phe Glu Gln Leu Ala Gln Phe Lys Met Pro Trp Thr Ser Pro Ser Cys
65                 70                   75                   80

-continued

```
Gln Asn Ser Cys Glu Leu Gly Ile Gln Asn Leu Ser Phe Lys Val Arg
                85                  90                  95
Ser Gly Gln Met Leu Ala Ile Ile Gly Ser Ser Gly Cys Gly Arg Ala
            100                 105                 110
Ser Leu Leu Asp Val Ile Thr Gly Arg Gly His Gly Gly Lys Ile Lys
            115                 120                 125
Ser Gly Gln Ile Trp Ile Asn Gly Gln Pro Ser Ser Pro Gln Leu Val
        130                 135                 140
Arg Lys Cys Val Ala His Val Arg Gln His Asn Gln Leu Leu Pro Asn
145                 150                 155                 160
Leu Thr Val Arg Glu Thr Leu Ala Phe Ile Ala Gln Met Arg Leu Pro
                165                 170                 175
Arg Thr Phe Ser Gln Ala Gln Arg Asp Lys Arg Val Glu Asp Val Ile
            180                 185                 190
Ala Glu Leu Arg Leu Arg Gln Cys Ala Asp Thr Arg Val Gly Asn Met
            195                 200                 205
Tyr Val Arg Gly Leu Ser Gly Gly Glu Arg Arg Val Ser Ile Gly
        210                 215                 220
Val Gln Leu Leu Trp Asn Pro Gly Ile Leu Ile Leu Asp Glu Pro Thr
225                 230                 235                 240
Ser Gly Leu Asp Ser Phe Thr Ala His Asn Leu Val Lys Thr Leu Ser
                245                 250                 255
Arg Leu Ala Lys Gly Asn Arg Leu Val Leu Ile Ser Leu His Gln Pro
            260                 265                 270
Arg Ser Asp Ile Phe Arg Leu Phe Asp Leu Val Leu Leu Met Thr Ser
        275                 280                 285
Gly Thr Pro Ile Tyr Leu Gly Ala Ala Gln His Met Val Gln Tyr Phe
        290                 295                 300
Thr Ala Ile Gly Tyr Pro Cys Pro Arg Tyr Ser Asn Pro Ala Asp Phe
305                 310                 315                 320
Tyr Val Asp Leu Thr Ser Ile Asp Arg Arg Ser Arg Glu Gln Glu Leu
                325                 330                 335
Ala Thr Arg Glu Lys Ala Gln Ser Leu Ala Ala Leu Phe Leu Glu Lys
            340                 345                 350
Val Arg Asp Leu Asp Asp Phe Leu Trp Lys Ala Glu Thr Lys Asp Leu
            355                 360                 365
Asp Glu Asp Thr Cys Val Glu Ser Ser Val Thr Pro Leu Asp Thr Asn
370                 375                 380
Cys Leu Pro Ser Pro Thr Lys Met Pro Gly Ala Val Gln Gln Phe Thr
385                 390                 395                 400
Thr Leu Ile Arg Arg Gln Ile Ser Asn Asp Phe Arg Asp Leu Pro Thr
                405                 410                 415
Leu Leu Ile His Gly Ala Glu Ala Cys Leu Met Ser Met Thr Ile Gly
            420                 425                 430
Phe Leu Tyr Phe Gly His Gly Ser Ile Gln Leu Ser Phe Met Asp Thr
        435                 440                 445
Ala Ala Leu Leu Phe Met Ile Gly Ala Leu Ile Pro Phe Asn Val Ile
        450                 455                 460
Leu Asp Val Ile Ser Lys Cys Tyr Ser Glu Arg Ala Met Leu Tyr Tyr
465                 470                 475                 480
Glu Leu Glu Asp Gly Leu Tyr Thr Thr Gly Pro Tyr Phe Phe Ala Lys
                485                 490                 495
Ile Leu Gly Glu Leu Pro Glu His Cys Ala Tyr Ile Ile Ile Tyr Gly
```

```
                 500             505             510
Met Pro Thr Tyr Trp Leu Ala Asn Leu Arg Pro Gly Leu Gln Pro Phe
        515                 520                 525
Leu Leu His Phe Leu Leu Val Trp Leu Val Val Phe Cys Cys Arg Ile
        530                 535                 540
Met Ala Leu Ala Ala Ala Leu Leu Pro Thr Phe His Met Ala Ser
545                 550                 555                 560
Phe Phe Ser Asn Ala Leu Tyr Asn Ser Phe Tyr Leu Ala Gly Gly Phe
                565                 570                 575
Met Ile Asn Leu Ser Ser Leu Trp Thr Val Pro Ala Trp Ile Ser Lys
        580                 585                 590
Val Ser Phe Leu Arg Trp Cys Phe Glu Gly Leu Met Lys Ile Gln Phe
        595                 600                 605
Ser Arg Arg Thr Tyr Lys Met Pro Leu Gly Asn Leu Thr Ile Ala Val
        610                 615                 620
Ser Gly Asp Lys Ile Leu Ser Ala Met Glu Leu Asp Ser Tyr Pro Leu
625                 630                 635                 640
Tyr Ala Ile Tyr Leu Ile Val Ile Gly Leu Ser Gly Gly Phe Met Val
                645                 650                 655
Leu Tyr Tyr Val Ser Leu Arg Phe Ile Lys Gln Lys Pro Ser Gln Asp
                660                 665                 670
Trp
```

<210> SEQ ID NO 9
<211> LENGTH: 6043
<212> TYPE: DNA
<213> ORGANISM: Homo sapiens
<220> FEATURE:
<223> OTHER INFORMATION: ABCG8 exon 2 (reverse strand) through ABCG5
      exon 2 (forward strand)

<400> SEQUENCE: 9

```
acctggtagg tgagatctct gacctccaga gtgttggact gaccactgta ggtgaagtac      60
agactgttgt cactttccga ggagaacaag ctgtcctgga ggccctgctg ggagacatgt     120
agtcaatgtg taagggtcac atgcagagag cgccttcccc ggttctcatt tctttgtgtt     180
ggaaaccatc agattcttct ctccgggtct tttgctttga aagtaaaatt tttattttat     240
tttgtgtgta tgactgtttg cctgcatgca tgtgcgtgcg ccacacacat acctggcacc     300
ctcagaggtc aaaagaggtc actgggtcct ctggacctgg agttatgggt ggttgtgaac     360
catctgtgtg tgatgggaat ggggtccagg tattctcagg tgcttttaat gtttgagcat     420
caccccagct ccattctctg atctttacta aaaataata atagcaatgg cttaaactat     480
ggtcaccccg ctgtgcttca gaacactaga atttatgtct cccatctcat tttgatgccc     540
aggatctgac tgccaaccat cccctaccct gtaatataat tcatctctct gaagtaggaa     600
tatattggag atatcttttg gggtgtgtgt gtgtgtgtgt gtgtgtgtgt gtgtgtgtgt     660
tggggaatca aatccatagc atcaaatata ctaggccaat catgatactg acagaaccat     720
agcaacacat ccgggtccc  tggggtttct tgttttcaaa tcaattatct ttaggagaga     780
tcttagttac ttgcatgggc taggaatttg ttcctagaca cttgtactga tacaaagttt     840
cttccattgg cttcaggagt ggaggggcta ctgagggagg aaagctctca ggttactgcg     900
ctaatgtgaa gacctggggg ggggggggtt agacagacag agaggacaga gtggaagaca     960
gggatgcagt tgattagtgc ccaggtcgcc actctgactc actcaaaccc actgacccg    1020
```

```
tccacacgga gagtctgggt ttccaggagc ctcacagtca actcagcttc tgaaaggaaa    1080
aaaaaaatat atcctgtctg gcttgtggat gacttctgtt ccatttaaa atatttcct     1140 tggcacccag gaaggattcc tgaggttttg acaaattctc tctatttttc aaacccttaa   1200
atatctattc ggctgacaca ttaatcagca cgactgtcag aacatcattt gaatctgtga   1260
caggtgacac cctaaaaaag tgaaagcggg tttatttgta ggtaactagt gtggctcctg   1320
ctgggctaca atgtaacgtc tccttgtatt aacttctggt tacattcctg agtcagaagc   1380
acagacacat gggaaaatcc agagggcaca aaaagggaga atgtgcaga aaacagtggt    1440 gcctggtggg gacatatatg gtaagtcttt ggcccaaggc acatacctgg ccctctgttg   1500 accccctgcag acaccatctc atctgcctct gcttagagtc caggctttcc tatccctgtc  1560
tgcagtgcga ggagctgtag accatgggtc ctggcgccct ggtactcagt gccagaattc   1620
cctgtgagat agccctgatc tcctccctcc ttccaggcca tcactgagta tgggtagtgc   1680
cggtctctgt gaagacctga ctcgaatatg agtagaaaga cggtgtggcc gctatgtgag   1740
ttctttgtag agtgagatgc tgggtgggca gaggaggaga tggatggcca cggcatggag   1800
cagaagccag ccagctccgc aagaaatgct cagttttcta aatttgcata cagagatgag   1860
aggctggaaa ccactgggca gtttttagct tgactgacag cttttaagaa cggaggcaca   1920
gggcatatca gtgtcattgt ctccccccca ccccaagccc tgcagttgtc agtggcgggc   1980
catcacaggg cacctacaac agtgggacct cacagaagga acttgtaggt ggcaggacct   2040
aggcacactt ttgaatatag aattctgaca gctcattgcc ttttagctg taatctgaag    2100 ggcaaaagcc cccacaccca ccactgattt tatatcctac tcaggaaggg agcatcaaag   2160
acgtagaagt agttatttcc ccatagacgt ctgcctcatg gggattctga cagcagagtt   2220
gcctgttgct gtggtagtag gattggtcaa tctcaggcaa tcctgtctcc cctagaacag   2280
gggactgagg cgtccctgtt gaatgtggcc atcctgttct ggtctttgtc tccagaaaag   2340
tgggccgggt gtagaagctg gggggagggg gaggtcgtct ttgctctgtc ttcccatact   2400
gccttctgct tcaaatcctg cccacaactc gagtcaaagg ccatttatca agcaaatgtt   2460
tctccggtta atgaggaagg aggcctagga gctccacttc ctggccacct cgctgctctc   2520
tgtccactct gcctccctcc cagaccataa gactgcaagc acacaattct gacgctccca   2580
aacaagcgat cactatcaca gccagtgtat ttgtaaactg cctgaaacca atgtgtagcc   2640
atagaaatat tttcttgtaa taagagaaaa aaataaatcg tgggctgggg gaatggctca   2700
gttgtagaac acttggttca acctccctgt tacacacagg ggggggggg agaagtgggg    2760 gggcagaagg agaggaagga agaaggaaga gggaagagga gaaagaggaa agtggccctc   2820
agagggattt atgacctgac ttcccagccg tgagccctgc cctttcagtg aggtttctct   2880
aagcagagcc tcaactctac aaggtagcga gatgcctcaa cccctccttg gcatttgttc   2940
ctgacacctg ccctttctct ctgtctctct gtctattggt ctgtctgtcc ctgcagcttc   3000
tcagcctcac acagagacct ttaggcttcc ccctggcctt ctctttcctc ctggttctca   3060
ccaaacaatg ccaaggacta acttactaca taagtatggc aagcgtagcg atcctgttgt   3120
tacctccccc gctgtctctt gactaccact gagattcttg gtctgacagt cacatgggtc   3180
aacgctctgt gatggaatgt catttggaaa acatcaatcc cggtcattca caggagcgtg   3240
ctgtcgtggg gaagtgacct cagaggtctc ctggctcctg agactgttcc cctcagacca   3300
tcaacactga ggagacaggg ccctgccgcc ccatttccat tctacttgaa gtccaggtgg   3360
tacattagga ctaatcctgt ggtaggaaag aaaagtcagt ctgacactgc ctcccccctg   3420
```

-continued

```
gcagagctca ctcaccgaag catcctgaag tacagtccca ttccacagct gggtctcttc     3480
tttggttttc tcagccatga ccagtgctgt ttgtgccctt tgtgtggcct cccctgctgt     3540
tgggctctct ctgtctttgc tccttagagc tggggcacct gagccctcct ctgtgccagc     3600 cttctctccca gcattcctyt ctggcaaaca cttcctataa acacaccgtg tgttctgcct     3660
attgtcgaga taaggacact ctggctaaag gtacatcaga taatggcatc gttggccaaa     3720
ttggtgaact gttatctcac gaggattcca gggctgggta ggatcggaca gggcactccc     3780
attggctcct cagttaaagc tgccctggag ccggacaggc cactagaaaa ttcacttgca     3840
tttgcttcct gctagccatg ggtgagctgc cctttctgag tccagaggga gccagagggc     3900
ctcacatcaa cagagggtct ctgagctccc tggagcaagg ttcggtcacg ggcacagagg     3960
ctcggcacag cttaggtgtc ctgcatgtgt cctacagcgt caggtaaggg gacctccaca     4020
gcaaaaagct aggctctctg attgccttt ctgaatgggt gggtgggcct gtgggctttg     4080
ggttgtctgt ccagcagatc agggtgaaag tggacagtct gtaacaacag tgagtcgttc     4140
ctcctcctcc tcctgcgcag ggcagagcct ggacattaaa acatgccctg cctgaagccg     4200
cttgctgctt ctcactgatt tctgctctcc ccttccttga ctcgcccacc acctgtcctg     4260
tgtagatgga gaaggctcgg agagtggggg tgctgggggc acaaaatgga atgaacactg     4320
ctgaaggaat gcagggttca cttcaagaag aaagcagtgt gcaggtgtac catctcccag     4380
tcagagaccc agtaatcaga gcagctaatg ggaggcatgc tccttgggtg gtggccaact     4440
tgtcattata cctccaagga caacagagtg gtacataagg ctaaacaga gttgtcaacc     4500 tgtccagggg caactgggat ggggtagggc tgggagcagg ggtctggcac cttccaggac     4560
cctactctgc ctttgcccct gtgggatttc ctttaaagca accgtgtcgg gccttggtgg     4620
aacatcaaat catgccagca gaagtgggac aggcaaatcc tcaaagatgt ctccttgtac     4680
atcgagagtg gccagattat gtgcatctta ggcagctcag gtaagtgcct ggggggscsg     4740
gggctcctgt acttctaagg caggctctgg gaggctttgg ctcygtctaa gcacaatgtt     4800
taagaagtra gtttaagttg tagagaggca gccatgcatt tggcatttga atacaatctg     4860
gtgacttgtc tggctgccaa tagaacctag taccaaagtg aaatcttgag gaaaatccct     4920
ggaaagagtg gaaagtcctg cctaacacgt aagtgccttc tttgcttgtt tgattgactg     4980
tgatgctaga gagcaaaccc agagccttgg gcatgctcag taaaccttct gccccagcac     5040
cccagcccca aatgtatttc cctcccttcc tccttccctt cctttcccttt cctcccttct     5100 ctcccttttt ttctttcttc cttctatatt tctttctttt cttccttcc tttcttcctt     5160 tcttcctttc ttttctttg tttctttgtt tcttctttc tttcttcctt actttctttc     5220
tcactttgca ttctgctcac tgaccttctc ctggccaccc ctcctgattg tttgattgac     5280
tgtggtgcag ggaggcctag gagagctaag agcccaggtc aagttgactc tgttggtctt     5340
cctgtggagt tccttcgaag gcccccaatt ctactttcaa ctgatattcc cacatctgga     5400
aagtttttgt caaggagttg ttaggcagga cttaacttct attcctgacc ctacttgtct     5460
tttcattatg atggtcatca gacacacagt tgagaacaga taccactaaa aaagacctca     5520
tgttaatata gtctcaccga gcacaccaag cacaccaggc tttctttggg cctctctctt     5580
caggagttaa gcatcacaca cactgcgctg agcccacctg tgtgtattcc ccgtgtctca     5640
ctattctttc caggtgagat tttaacctt gaatgtgact tccatgtttg ttttgtgttc     5700
ttccactaac tgtcattatc ctctgagggg tttcctcctc tgcccctgca aaacctatag     5760
```

-continued

```
ctgtaaattt tcctatctgc agcagctggg gagggtaca ctggcccaga agagggctc      5820 tgggtagcat gccgcagtgt tcgcaacact gggttattct gaatgcctct gcttaaggat    5880
tctggcatat tcgactcaca gaccgttctt gactgagcag ccccttgtaa actgtcagca   5940
tttaactgtc cccttgcctt gtgctctctt agaaacaggc agtgtaaggc tgtggggaga   6000
gtcaggtatg acactgttgg gtgtagctga gagtgagtcc caa                      6043
```

<210> SEQ ID NO 10
<211> LENGTH: 359
<212> TYPE: DNA
<213> ORGANISM: Homo sapiens
<220> FEATURE:
<223> OTHER INFORMATION: sequence between ABCG5 and ABCG8 containing control sequences (bidirectional promoter)

<400> SEQUENCE: 10

```
gaccagtgct gtttgtgccc tttgtgtggc ctcccctgct gttgggctct ctctgtcttt     60
gctccttaga gctggggcac ctgagccctc ctctgtgcca gcctttctcc cagcattcct   120
ytctggcaaa cacttcctat aaacacaccg tgtgttctgc ctattgtcga gataaggaca   180
ctctggctaa aggtacatca gataatggca tcgttggcca aattggtgaa ctgttatctc    240
acgaggattc cagggctggg taggatcgga cagggcactc ccattggctc ctcagttaaa    300
gctgccctgg agccggacag gccactagaa aattcacttg catttgcttc ctgctagcc     359
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:6-His epitope tag

<400> SEQUENCE: 11

```
His His His His His His
 1               5
```

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: anti-DYKDDDDK epitope tag

<400> SEQUENCE: 12

```
Asp Tyr Lys Asp Asp Asp Asp Lys
 1               5
```

<210> SEQ ID NO 13
<211> LENGTH: 200
<212> TYPE: PRT
<213> ORGANISM: Artificial Sequence
<220> FEATURE:
<223> OTHER INFORMATION: Description of Artificial Sequence:flexible linker
<220> FEATURE:
<221> NAME/KEY: MOD_RES
<222> LOCATION: (6)..(200)
<223> OTHER INFORMATION: Gly at positions 6-200 may be present or absent

<400> SEQUENCE: 13

```
Gly Gly Gly Gly Gly Gly Gly Gly Gly Gly Gly Gly Gly Gly Gly Gly
 1               5                  10                  15
```

-continued

```
Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
            35                  40                  45

Gly Gly Gly Gly Gly Gly Gly Gly Gly Gly Gly Gly Gly Gly Gly
 50                      55                  60

Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
            115                 120                 125

Gly Gly Gly Gly Gly Gly Gly Gly Gly Gly Gly Gly Gly Gly Gly
            130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly
            180                 185                 190

Gly Gly Gly Gly Gly Gly Gly Gly
            195                 200
```

ABCG8 VECTORS, HOST CELLS, AND METHOD OF MAKING

CROSS REFERENCE TO RELATED APPLICATIONS

The present application claims priority to U.S. Provisional Patent Application No. 60/252,235, filed Nov. 20, 2000, and No. 60/253,645, filed Nov. 28, 2000, the teachings of both of which are incorporated herein by reference for all purposes.

BACKGROUND OF THE INVENTION

In humans the intestine presents a barrier that prevents the absorption of plant sterols and partially blocks the absorption of cholesterol. This barrier is disrupted in the rare autosomal recessive disorder, sitosterolemia (Bhattacharyya, et al., *J. Clin. Invest.* 53:1033 (1974)). Sitosterolemic patients Hyperabsorb the plant sterols such as sitosterol, which provide the identifying feature of this disease (Bhattacharyya, et al., *J. Clin. Invest.* 53:1033 (1974); Bjorkhem and Boberg, in *The Metabolic and Molecular Bases of Inherited Disease*, Scriver, et al., Eds., pp. 2073 vol. 2, chap. 65 [seventh edition] (McGraw Hill, New York, 1995); Salen, et al., *J. Lipid Res.* 33:945 (1992)). These patients also hyperabsorb cholesterol and are usually hypercholesterolemic, resulting in the development of xanthomas (cholesterol deposits in skin and tendons) and premature coronary artery disease (Bjorkhem and Boberg, in *The Metabolic and Molecular Bases of Inherited Disease*, Scriver, et al., Eds., pp. 2073 vol. 2, chap. 65 [seventh edition] (McGraw Hill, New York, 1995); Salen, et al., *J. Lipid Res.* 33:945 (1992)). Unlike other forms of hyperlipidemia, sitosterolemic subjects respond to restriction in dietary cholesterol and to bile acid resin treatment with dramatic reductions in plasma cholesterol levels (Bjorkhem and Boberg, in *The Metabolic and Molecular Bases of Inherited Disease*, Scriver et al., Eds., pp. 2073 vol. 2, chap. 65 [seventh edition] (McGraw Hill, New York, 1995); Salen, et al., *J. Lipid Res.* 33:945 (1992); T. A. Miettinen, *Eur. J. Clin. Invest.* 10:27 (1980); Morganroth, et al., *J. Pediatr.* 85:639 (1974)).

Patients with sitosterolemia have markedly elevated (>30-fold) plasma levels of plant sterols (sitosterol, stigmasterol and campesterol) as well as other neutral sterols with modified side chains (Bhattacharyya, et al., *J. Clin. Invest.* 53:1033 (1974); Salen, et al., *J. Lipid Res.* 26:203 (1985); Gregg, et al., *J. Clin. Invest.* 77:1864 (1986)). Normal humans absorb only ~5% of the 200 to 300 mg of plant sterols consumed each day (Gould, et al., *Metabolism* 18:652 (1969); Salen, et al., *J. Clin. Invest.* 49:952 (1970)). Almost all of the absorbed sitosterol is quickly secreted into the bile so that only trace amounts of sitosterol and other plant sterols remain in the blood (Gould, et al., *Metabolism* 18:652 (1969); Salen, et al., *J. Clin. Invest.* 49:952 (1970)). In contrast, subjects with sitosterolemia absorb between 15 and 60% of ingested sitosterol, and they excrete only a fraction into the bile (Bhattacharyya, et al., *J. Clin. Invest.* 53:1033 (1974); Bjorkhem and Boberg, in *The Metabolic and Molecular Bases of Inherited Disease*, Scriver, et al., Eds., pp. 2073 vol. 2, chap. 65 [seventh edition] (McGraw Hill, New York, 1995); Salen, et al., *J. Lipid Res.* 33:945 (1992); T. A. Miettinen, *Eur. J. Clin. Invest.* 10:27 (1980)). The liver secretes sitosterol into the bloodstream where it is transported as a constituent of low density and high density lipoprotein particles (Bhattacharyya, et al., *J. Clin. Invest.* 53:1033 (1974)). With the exception of the brain, the relative proportion of sterol represented by sitosterol in tissues matches that in plasma (10–25%) (Salen, et al., *J. Lipid Res.* 26:1126 (1985)). Hyperabsorption and inefficient secretion is not limited to plant sterols. Sitosterolemic subjects absorb a higher fraction of dietary cholesterol than normal subjects, and they secrete less cholesterol into the bile (Bhattacharyya, et al., *J. Clin. Invest.* 53:1033 (1974); Bjorkhem and Boberg, in *The Metabolic and Molecular Bases of Inherited Disease*, Scriver, et al., Eds., pp. 2073 vol. 2, chap. 65 [seventh edition] (McGraw Hill, New York, 1995); Salen, et al., *J. Lipid Res.* 33:945 (1992); T. A. Miettinen, *Eur. J. Clin. Invest.* 10, 27 (1980)). Taken together, the genetic and metabolic data indicate that sitosterolemic patients lack a gene product that normally limits the absorption and accelerates the biliary excretion of sterols (Bjorkhem and Boberg, in *The Metabolic and Molecular Bases of Inherited Disease*, Scriver et al., Eds., pp. 2073 vol. 2, chap. 65 [seventh edition] (McGraw Hill, New York, 1995); Salen, et al., *J. Lipid Res.* 33:945 (1992)).

The molecular mechanisms that limit sterol absorption are poorly understood, but clues have emerged recently from studies of the orphan nuclear hormone receptor LXR (Repa, et al., *Science* 289:1524 (2000)). Mice treated with an LXR agonist have a marked decrease in cholesterol absorption and a corresponding increase in the intestinal expression of mRNA encoding the ATP binding cassette protein (ABC) 1, a membrane-associated protein that has been implicated in the transport of cholesterol (Repa, et al., *Science* 289:1524 (2000); Lawn, et al., *J. Clin. Invest.* 104:25 (1999)).

Clearly, new approaches for reducing the absorption of dietary cholesterol, for maximizing the elimination of excess cholesterol from the liver, and for treating sterol-associated disorders such as sitosterolemia would have tremendous public health benefits. The present invention addresses these and other needs.

SUMMARY OF THE INVENTION

The present invention provides nucleic acids encoding a novel ABC family sterol transporter, called ABCG8. The herein-disclosed sequences can be used for any of a number of purposes, including for the diagnosis and treatment of sterol-associated disorders, including sitosterolemia, and for the identification of molecules that associate with and/or modulate the activity of ABCG8 and, in turn, modulate the absorption of dietary cholesterol.

In one aspect, the present invention provides an isolated nucleic acid encoding an ABCG8 polypeptide, the polypeptide comprising at least about 70% amino acid sequence identity to an amino acid sequence as set forth in SEQ ID NO:4 or 8.

In one embodiment, the polypeptide specifically binds to polyclonal antibodies generated against a polypeptide that comprises an amino acid sequence of SEQ ID NO:4 or 8. In another embodiment, the polypeptide comprises an amino acid sequence of SEQ ID NO:4 or 8. In another embodiment, the polypeptide forms a dimer with a second ABC polypeptide, wherein the dimer comprises sterol transport activity. In another embodiment, the dimer is a heterodimer. In another embodiment, the sterol is cholesterol. In another embodiment, the second ABC polypeptide is ABCG5. In another embodiment, the ABCG5 polypeptide (1) comprises an amino acid sequence that is at least about 70% identical to an amino acid sequence as set forth in SEQ ID NO:2 or 6; (2) selectively binds to polyclonal antibodies generated against a polypeptide comprising an amino acid sequence as set forth in SEQ ID NO:2 or 6; (3) comprises an amino acid sequence selected from the group consisting of SEQ ID NO:2 and SEQ ID NO:6; (4) is encoded by a nucleic acid that hybridizes under moderately stringent (or stringent conditions) conditions to a nucleic acid comprising a nucleotide sequence as set forth in SEQ ID NO:1 or 5; (5) is encoded by a nucleic acid that comprises a nucleotide sequence that is at least about 70% identical to a sequence as set forth in SEQ ID NO:1 or 5; or (6) is encoded by a nucleic acid that comprises a nucleotide sequence of SEQ ID NO:1 or 5.

In another embodiment, the nucleic acid hybridizes under moderately stringent hybridization conditions to a nucleic acid comprising a nucleotide sequence of SEQ ID NO:3 or 7. In another embodiment, the nucleic acid hybridizes under stringent hybridization conditions to a nucleic acid comprising a nucleotide sequence of SEQ ID NO:3 or 7. In another embodiment, the nucleic acid comprises a nucleotide sequence that is at least about 70% identical to SEQ ID NO:3 or 7. In another embodiment, the nucleic acid comprises a nucleotide sequence of SEQ ID NO:3 or 7. In another embodiment, the nucleic acid is greater than 500, 1000, 1500, 2000, or more nucleotides in length. In another embodiment, the nucleic acid is from a mouse or a human. In another embodiment, the nucleic acid is expressed in the intestine or the liver in the presence of an LXR agonist. In another embodiment, the nucleic acid is expressed in the liver, the jejunum, the ileum, or the duodenum.

In another aspect, the present invention provides an expression cassette comprising any of the above-described nucleic acids. In another aspect, the present invention provides an isolated cell comprising the expression cassette.

In another aspect, the present invention provides an isolated ABCG8 polypeptide, the polypeptide comprising an amino acid sequence that is at least about 70% identical to SEQ ID NO:4 or 8.

In one embodiment, the polypeptide selectively binds to polyclonal antibodies generated against a polypeptide comprising an amino acid sequence of SEQ ID NO:4 or 8. In another embodiment, the polypeptide comprises an amino acid sequence of SEQ ID NO:4 or 8. In another embodiment, the polypeptide forms a dimer with a second ABC polypeptide, wherein the dimer comprises sterol transport activity. In another embodiment, the dimer is a heterodimer. In another embodiment, the second ABC polypeptide is ABCG5. In another embodiment, the sterol is cholesterol. In another embodiment, the polypeptide is expressed in the intestine or the liver in the presence of an LXR agonist. In another embodiment, the polypeptide is expressed in the liver, jejunum, ileum, or duodenum. In another embodiment, the polypeptide is from a mouse or a human.

In another aspect, the present invention provides antibodies generated against a polypeptide comprising an amino acid sequence having at least about 70% amino acid sequence identity to SEQ ID NO:4 or 8.

In another aspect, the present invention provides a method of making an ABCG8 polypeptide, the method comprising (i) introducing a nucleic acid encoding an ABCG8 polypeptide comprising an amino acid sequence having at least about 70% amino acid sequence identity to SEQ ID NO:4 or 8 into a host cell or cellular extract; (ii) incubating the host cell or cellular extract under conditions such that the ABCG8 polypeptide is expressed in the host cell or cellular extract.

In one embodiment, the method further comprises recovering the ABCG8 polypeptide from the host cell or cellular extract.

In another aspect, the present invention provides a method of identifying a compound useful in the treatment or prevention of a sterol-related disorder, the method comprising contacting an ABCG8 polypeptide with a test agent, and determining the functional effect of the test agent upon the polypeptide, wherein a functional effect exerted on the polypeptide by the test agent indicates that the test agent is a compound useful in the treatment or prevention of the sterol-related disorder.

In one embodiment, the sterol is cholesterol. In another embodiment, the polypeptide comprises an amino acid sequence that is at least about 70% amino acid sequence identical to an amino acid sequence of SEQ ID NO:4 or 8. In another embodiment, the polypeptide is present in a cell or cell membrane. In another embodiment, the polypeptide is bound to a heterologous ABC polypeptide, forming a heterodimer. In another embodiment, the functional effect comprises an increase in the sterol transport activity of the polypeptide. In another embodiment, the functional effect comprises a physical interaction between the test agent and the polypeptide. In another embodiment, the physical interaction is detected using a direct binding assay. In another embodiment, the sterol-related disorder is sitosterolemia. In another embodiment, the sterol-related disorder is selected from the group consisting of hypercholesterolemia, hyperlipidemia, gall stones, HDL deficiency, atherosclerosis, and nutritional deficiencies.

In another aspect, the present invention provides a method of identifying a compound useful in the treatment or prevention of a sterol-related disorder, the method comprising contacting a cell with a test agent and determining the functional effect of the test agent upon the cell, wherein the cell expresses or is capable of expressing an ABCG8 polypeptide, and wherein a functional effect exerted on the cell by the test agent indicates that the test agent is a compound useful in the treatment or prevention of the sterol-related disorder.

In one embodiment, the sterol is cholesterol. In another embodiment, the polypeptide comprises an amino acid sequence that is at least about 70% amino acid sequence identical to an amino acid sequence of SEQ ID NO:4 or 8. In another embodiment, the compound produces an increase in the expression of an ABCG8 gene that encodes the polypeptide. In another embodiment, the increase in the expression of the ABCG8 gene is detected by detecting the level of ABCG8 mRNA in the cell. In another embodiment, the increase in the expression of the ABCG8 gene is detected by detecting the level of ABCG8 polypeptide in the cell. In another embodiment, the increase in the expression of the ABCG8 gene is detected by detecting the level of ABCG8 protein activity in the cell. In another embodiment, the compound modulates the level of sterol transport activity in the cell. In another embodiment, the sterol transport activity is detected by detecting the rate of sterol efflux in the cell. In another embodiment, the increase in the level of expression of the ABCG8 gene is mediated by LXR or RXR. In another embodiment, the sterol-related disorder is sitosterolemia. In another embodiment, the sterol-related disorder is selected from the group consisting of hypercholesterolemia, hyperlipidemia, gall stones, HDL deficiency, atherosclerosis, and nutritional deficiencies.

In another aspect, the present invention provides a method of treating or preventing a sterol-related disorder in a mammal, the method comprising administering to the mammal a compound that increases the level of expression or activity of an ABCG8 polypeptide in a plurality of cells of the mammal.

In one embodiment, the sterol is cholesterol. In another embodiment, the cholesterol-related disorder is sitosterolemia. In another embodiment, the sterol-related disorder is selected from the group consisting of hypercholesterolemia, hyperlipidemia, gall stones, HDL deficiency, atherosclerosis, and nutritional deficiencies. In another embodiment, the compound produces a decrease in the amount of dietary sterol that is absorbed in the mammal. In another embodiment, the compound produces a decrease in the amount of sterol that is retained in the liver of the mammal. In another embodiment, the compound inhibits the development of foam cells within the mammal. In another embodiment, the compound causes an increase in LXR or RXR activity in the mammal. In another embodiment, the compound is identified by contacting an ABCG8 polypeptide with a test agent and determining the functional effect of the test agent upon the polypeptide, wherein a functional effect exerted on the polypeptide by the test agent indicates that the test agent is a compound useful in the treatment or prevention of the sterol-related disorder. In another embodiment, the compound is identified by contacting a cell with a test agent and determining the functional effect of the test agent upon the cell, wherein the cell expresses or is capable of expressing an ABCG8 polypeptide, and wherein a functional effect exerted on the cell by the test agent indicates that the test agent is a compound useful in the treatment or prevention of the sterol-related disorder.

In another aspect, the present invention provides a method of prescreening to identify a candidate therapeutic agent that modulates ABCG8 activity in a mammal, the method comprising (i) providing a cell which comprises an ABCG8 polypeptide; (ii) providing a test compound; and (3) determining whether the amount of sterol transport activity in the cell is increased or decreased in the presence of the test compound relative to the activity in the absence of the test compound; wherein a test compound that causes an increase or decrease in the amount of sterol transport activity is a candidate therapeutic agent for modulation of ABCG8 activity in a mammal.

In one embodiment, the method further comprises a secondary step, wherein the test compound is administered to a mammal, and the absorption of dietary sterol in the mammal is detected.

BRIEF DESCRIPTION OF THE DRAWINGS

FIG. 3. (A) ABCG8 exon 2 (reverse strand) through ABCG5 exon 2 (forward strand) (SEQ ID NO:9). The four exons are underlined and the conserved regions are in uppercase. The sequence ends in intron 2 of ABCG5 and is in the following order: ABCG8—exon 2 (reverse strand); ABCG8—intron 1 (reverse strand); ABCG8—exon 1 (reverse strand); gap between genes; ABCG5—exon 1 (forward strand); ABCG5—intron 1 (forward strand); ABCG5—exon 2 (forward strand); and ABCG5—intron 2 (forward strand, partial). (B) The sequence between ABCG5 and ABCG8 in which the control sequences (e.g., bidirectional promoter, etc.) reside (SEQ ID NO:10).

DETAILED DESCRIPTION OF THE INVENTION AND SPECIFIC EMBODIMENTS

I. Introduction

Figure 1:
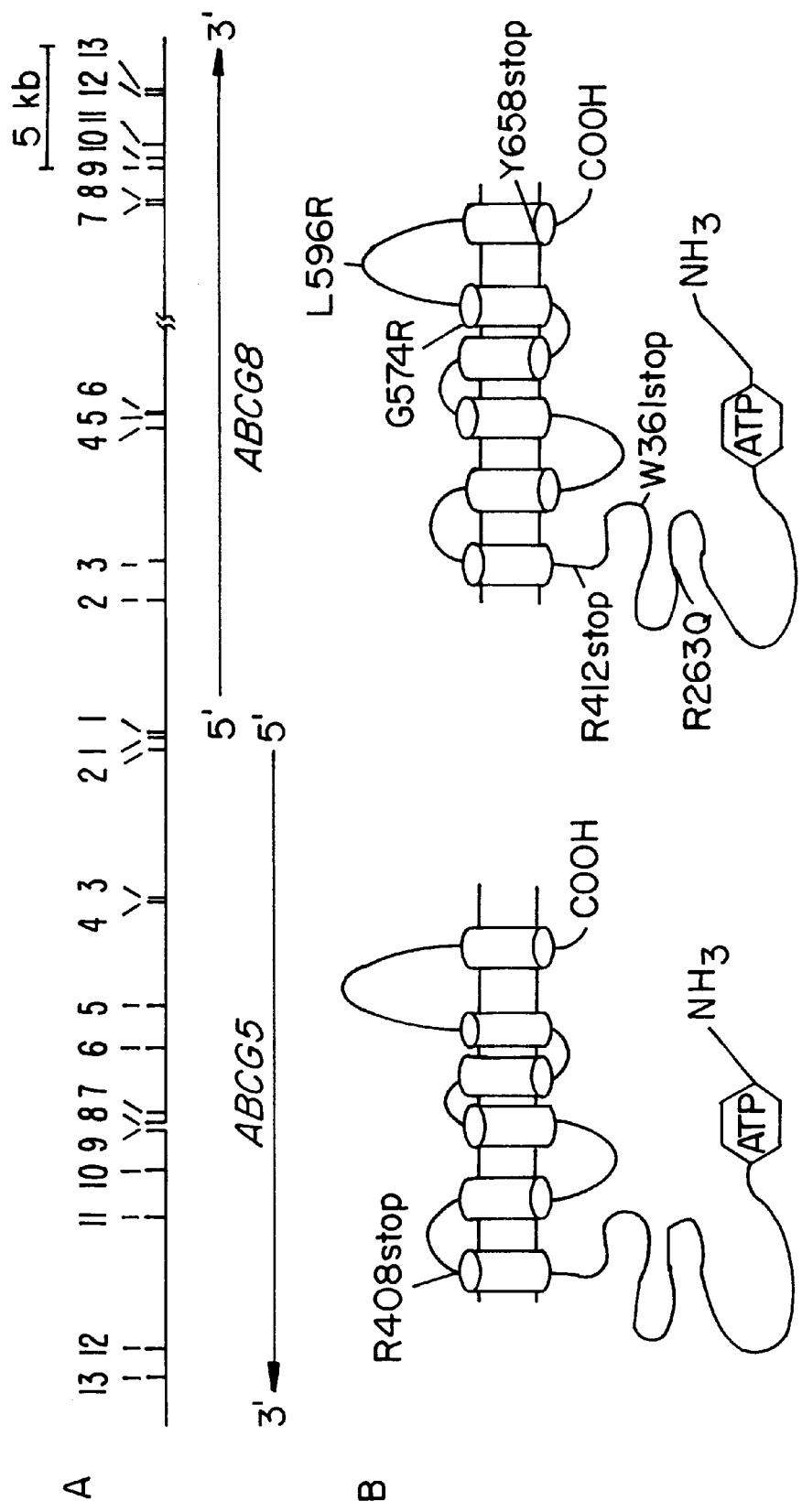
FIG. 1. Genomic structure (A), putative topology (B), and predicted amino acid sequences of ABCG5 (SEQ ID NO:6) and ABCG8 (SEQ ID NO:8) (C). ABCG5 and ABCG8 are located on chromosome 2p21 between markers D2S 177 and D2S 119. (A) ABCG5 and ABCG8 are tandemly arrayed in a head-to-head orientation separated by 374 basepairs. ABCG5 and ABCG8 are both encoded by 13 exons and each spans ~28 kb. (B) The mutations detected in patients with sitosterolemia (Table 2) are indicated on a schematic model of ABCG5 (left) and ABCG8 (right) (C) Predicted amino acid sequence of ABCG5 and ABCG8, which are 651 and 673 residues in length, respectively. Alignment of the inferred amino acid sequences indicates 28% sequence identity and 61% sequence similarity between ABCG5 and ABCG8. Both proteins are predicted to contain six transmembrane segments using the program MEMSAT 2 (Jones, et al., Biochem. 33:3038 (1994)). The putative transmembrane segments of each protein are indicated by cylinders (B) and lines (C). The Walker A motif and Walker B motifs are highlighted. The ABC signature sequence (C-motif) is indicated.

The present invention provides nucleic acids and polypeptides for ABCG8, a novel member of the ABC family of transporter molecules. Members of the ATP-binding cassette (ABC) family use ATP to drive the transport of any of a large number of molecules across membranes. ABCG8 is involved in the transport of cholesterol and other sterols, as well as other lipids, across membranes, and is associated with the human disorder sitosterolemia. ABCG8 sequences from human (see, e.g., SEQ ID NOs: 7 and 8) and mouse (see, e.g., SEQ ID NOs: 3 and 4) are provided. The genomic position of human (2p21) and mouse (chromosome 17) ABCG8 is also provided. Significantly, the map position of human ABCG8 corresponds to the map position of the sitosterolemia-causing gene (see, e.g., Patel et al., (1998) J. Clin. Invest. 102:1041–1044).

Without being bound by any theory, it is speculated that ABCG8 acts to effect sterol transport activity as a monomer or, more preferably, as a homodimer or heterodimer. In particular, it is speculated that, at least in certain cells, ABCG8 binds to the ABCG5 transporter to achieve sterol transport activity. It is speculated that ABCG5 and ABCG8 normally cooperate to limit intestinal absorption and promote biliary excretion of sterols. It is further speculated that, in patients with sitosterolemia, the gene encoding the ABCG5 moiety and/or the gene encoding the ABCG8 moiety of the ABCG5–ABCG8 heterodimer is mutated, thereby eliminating function of the heterodimer and abolishing sterol transport activity in cells. For instance, sitosterolemic patients have been found to be heterozygous for a transition mutation (CGA to TGA) in codon 408 of ABCG5 (SED ID NO:6) that introduced a premature stop codon between TM1 and TM2. Other sitosterolemic patients have been found to be either homozygous or heterozygous for a nonsense mutation (c.1083G>A) in exon 7 that introduced a premature termination signal at codon 361, thereby terminating the ABCG8 protein prior to TM1. Other sitosterolemic patients have been found to be heterozygous for another nonsense mutation in exon 13 that introduced a stop codon 15 residues from the carboxy terminal of ABCG8. Other sitosterolemic patients have been found to be heterozygous for a missense mutation in exon 6 in codon 263 (R263Q) of ABCG8, whereas others have been found to be homozygous for a missense mutation in a residue (G574R) that is conserved in both mouse and human ABCG8. Table 2, infra, lists various molecular defects that have been detected in ABCG5 and/or ABCG8 in nine unrelated individuals with sitosterolemia. It is also thought that mutations in other genes (perhaps other ABC transporters) within the genomic interval mapped by Patel et al. ((1998) *J. Clin. Invest.* 102:1041–1044) can cause sitosterolemia when present in combination with mutations in ABCG5 and ABCG8.

Because the ABCG5–ABCG8 heterodimer is speculated to cause sterol, e.g., cholesterol, efflux from cells (e.g., out of intestinal cells into the lumen, out of liver cells to allow clearance of cholesterol from the liver, and possibly out of macrophages or smooth muscle cells to counteract foam cell formation), a loss of transporter activity leads to an increase in the absorption of dietary cholesterol and other sterols and to an increase in foam cell formation. Accordingly, by increasing ABCG8 activity, it is possible to lower the absorption of dietary cholesterol and other sterols and to inhibit the development of foam cells. Such benefits can be achieved in any patient, e.g., to provide a treatment for sitosterolemia, hypercholesterolemia, atherosclerosis, coronary heart disease, hyperlipidemia, HDL deficiency, cholesterol gall stones, nutritional deficiencies, etc., or to prevent the development of any of these conditions in at risk patients.

Modulators, recombinant forms, or fragments of ABCG8 can be used to modulate sterol transport activity in cells, and can therefore be useful in the treatment or prevention of any of a large number of sterol, e.g., cholesterol, associated diseases and conditions, including, but not limited to, sitosterolemia, familial hypercholesterolemia, hyperlipidemia, atherosclerosis, coronary heart disease, HDL deficiencies, gall stones, nutritional deficiencies, and other cardiovascular diseases. It will be appreciated that the herein-described methods can be used either to increase or decrease the level of dietary sterol absorption. Thus, the present methods can be used to treat or prevent any condition associated with a sterol, e.g., cholesterol, deficiency by increasing the level of sterol absorption in patients affected with the condition. Modulation of ABCG8 can also be used to modulate the development of foam cells, e.g., by modulating sterol, e.g., cholesterol retention in macrophages. In addition, modulators, recombinant forms, or fragments of ABCG8 can be used to treat or prevent any sitosterolemia-associated condition such as arthritis, xanthomas, and chronic hemolytic anemia, in patients with sitosterolemia or in any other patient.

In numerous embodiments, the present invention provides methods of screening for modulators, e.g., activators, inhibitors, stimulators, enhancers, etc., of ABCG8 nucleic acids and proteins. Such modulators can affect ABCG8 activity in any of a number of ways, e.g., by modulating ABCG8 transcription, translation, phosphorylation, mRNA or protein stability; by altering the binding of ABCG8 to heterologous proteins or other molecules; by affecting ABCG8 protein activity, or by modulating LXR or RXR activity. In preferred embodiments, modulators that enhance ABCG8 activity or levels are used to treat any of the above-recited diseases and conditions.

In one embodiment, compounds are screened, e.g., using high throughput screening (HTS), to identify those compounds that can bind to and/or modulate the activity of an isolated ABCG8 polypeptide or fragment thereof. In another embodiment, ABCG8 proteins are recombinantly expressed in cells, and potential modulators of ABCG8 are assayed by measuring an indicator of ABCG8 activity, such as sterol transport activity.

In numerous embodiments, an ABCG8 polynucleotide or polypeptide is introduced into a cell, in vivo or ex vivo, and the ABCG8 activity in the cell is thereby modulated. For example, a polynucleotide encoding a full length ABCG8 polypeptide is introduced into a population of cells, thereby increasing the level or activity of ABCG8 in the cells. Alternatively, an antisense, ribozyme, or dominant-negative encoding polynucleotide can be introduced into a population of cells, thereby inhibiting ABCG8, and associated sterol transport, in the cells.

The present invention also provides molecular tools for the diagnosis of sitosterolemia, e.g., by examining the nucleotide or amino acid sequence of ABCG8 in a patient, or by examining the level of expression or activity of ABCG8 in a patient. In addition, the present methods can be used to identify sitosterolemia-causing mutations in heterozygous carriers. In any of these embodiments, a detection of one or more mutations in an ABCG8 gene that can diminish or alter the level of ABCG8 protein or protein activity in a cell indicates that the patient has sitosterolemia, is at risk for sitosterolemia, or is a carrier of a sitosterolemia-causing allele. The detection of mutations in an ABCG8 gene can also be used to detect the presence of or risk for developing any of the herein-described sterol-related disorders.

The present invention also provides methods for detecting ABCG8 nucleic acid and protein expression, allowing investigation into ABCG8-associated sterol transport, and for detecting cells specifically involved in sterol transport. In addition, ABCG8 nucleic acids and polypeptides provide useful markers for detecting LXR or RXR activity, e.g., to screen for LXR or RXR agonists. ABCG8 also provides useful nucleic acid probes for paternity and forensic investigations. ABCG8 polypeptides can also be used to generate monoclonal and polyclonal antibodies useful for identifying cells involved in cholesterol transport. ABCG8 expression can be identified using techniques such as reverse transcription and amplification of mRNA, isolation of total RNA or poly A$^+$RNA, northern blotting, dot blotting, in situ hybridization, RNase protection, S1 digestion, probing DNA microchip arrays, western blots, and the like.

Because the chromosome location of ABCG8 in mice and in humans is known, the present invention also provides markers for chromosome mapping studies, e.g., for meiotic mapping studies to identify the location of nearby disease-causing genes.

Functionally, ABCG8 nucleic acids encode transporter molecules that act in the transport of sterols, e.g., cholesterol, and other lipids across cell membranes. Such ABCG8 polypeptides act to effect sterol transport in a large number of cells, including, but not limited to, cells of the liver, the intestine, in macrophages, and in smooth muscle cells. ABCG8 belongs to the ABCG subfamily of transporters, and binds to ABC family members, e.g., ABCG5, to effect cholesterol transport. Structurally, the nucleotide sequence of ABCG8 (see, e.g., SEQ ID NOs:3 or 7, isolated from mice and humans, respectively) encodes polypeptides comprising one ATP binding domain, one hydrophobic domain (comprising six transmembrane segments), a Walker A motif, Walker B motif, Signature C motif, and other signature sequences typical of ABC transporters. Related ABCG8 genes from other species share at least about 60% nucleotide sequence identity over a region of at least about 50 nucleotides in length, optionally 100, 200, 500, or more nucleotides in length, to SEQ ID NO:3 or 7, or encode polypeptides sharing at least about 60% amino acid sequence identity over an amino acid region at least about 25 amino acids in length, optionally 50 to 100 amino acids in length to SEQ ID NO:4 or 8. Preferably, the ABCG8 polypeptide comprises 673 amino acids.

The present invention also provides polymorphic variants of the mouse ABCG8 protein depicted in SEQ ID NO:4 as well as polymorphic variants of the human ABCG8 protein depicted in SEQ ID NO:8. For instance, polymorphic variants of the human ABCG8 protein depicted in SEQ ID NO:8 include the following: variant #1, in which a cysteine residue is substituted for a tyrosine residue at amino acid position 54; variant #2, in which a lysine residue is substituted for a threonine residue at amino acid position 400; variant #3, in which a valine residue is substituted for an alanine residue at amino acid position 632; and variant #4, in which a phenylalanine residue is substituted for a tyrosine residue at amino acid position 641. As such, the present invention provides molecular tools that can be used to identify other sequence polymorphisms that are associated diseases such as hyperlipidemia, gall stones, atherosclerosis, etc.

Specific regions of the ABCG8 nucleotide and amino acid sequences may be used to identify polymorphic variants, interspecies homologs, and alleles of ABCG8 genes. This identification can be made in vitro, e.g., under stringent hybridization conditions, or by PCR and sequencing, or by using the sequence information in a computer system for comparison with other nucleotide sequences. Typically, identification of polymorphic variants and alleles of ABCG8 is made by comparing an amino acid sequence of about 25 amino acids or more, e.g., 50–100 amino acids. Amino acid identity of approximately at least 60% or above, optionally 65%, 70%, 75%, 80%, 85%, or 90–95% or above typically demonstrates that a protein is a polymorphic variant, interspecies homolog, or allele of ABCG8. Sequence comparison can be performed using any of the sequence comparison algorithms discussed below. Antibodies that bind specifically to ABCG8 polypeptides or a conserved region thereof can also be used to identify alleles, interspecies homologs, and polymorphic variants.

Polymorphic variants, interspecies homologs, and alleles of ABCG8 are confirmed by examining, e.g., interaction of the candidate variant, homolog, or allele to a heterologous ABC polypeptide, e.g., ABCG5, or the cholesterol transporting ability of the putative SSG polypeptide. Typically, an ABCG8 polypeptide having an amino acid sequence of SEQ ID NO:4 or SEQ ID NO:8 is used as a positive control in comparison to the putative ABCG8 protein to demonstrate the identification of a polymorphic variant or allele of the ABCG8 gene or protein.

Nucleotide and amino acid sequence information for ABCG8 may also be used to construct models of ABCG8 polypeptides in a computer system. These models are subsequently used to identify compounds that can activate or inhibit ABCG8 proteins. Such compounds that modulate the activity of ABCG8 genes or proteins can be used to investigate the role of ABCG8 genes in, e.g., sterol transport in cell, and can also be used to treat or prevent any of the herein-described conditions and diseases.

The present invention also provides assays, preferably high throughput assays, to identify compounds or other molecules that interact with and/or modulate ABCG8. In certain assays, a particular domain of ABCG8 is used, e.g., an ATP binding domain, a dimerization domain, or a transmembrane domain.

The present invention also provides methods to treat diseases or conditions associated with ABCG8 activity. For example, ABCG8 activity or expression can be altered in cells of a patient with any of a large number of disorders including, but not limited to, sitosterolemia, hypercholesterolemia, hyperlipidemia, atherosclerosis, xanthomas, arthritis, and hemolytic anemia. In such patients, increasing ABCG8 in, e.g., intestinal, liver, or macrophage cells will enhance the efflux of sterol from the cells, thereby providing a treatment for the disorder. In addition, modulation of an ABCG8 can be used to alter the amount and quality of sterols that are absorbed by a mammal from the diet. For example, increased ABCG8 activity in cells of the intestine can be used to decrease or block the amount of dietary cholesterol and other sterols, including plant sterols, absorbed by the patient.

Transgenic animals and cells lacking one or more ABCG8 alleles, or containing altered forms of ABCG8 are also provided, as are kits for using the herein-disclosed polynucleotides and polypeptides and for practicing the herein-disclosed methods, are also provided.

II. Definitions

As used herein, the following terms have the meanings ascribed to them below unless specified otherwise.

As used herein, an "ABCG8 protein" or "ABCG8 polypeptide" refers to a transporter as shown in SEQ ID NO:4 or 8, or any derivative, homolog, or fragment thereof, and an "ABCG8 polynucleotide" or ABCG8 nucleic acid" or "ABCG8 gene" refers to any nucleic acid encoding such a protein, derivative, homolog, or fragment thereof ABCG8 proteins or derivatives can be expressed in any cell type, including any eukaryotic or prokaryotic cell, or synthesized in vitro. Typically, ABCG8 nucleic acids or genes encode transporters that associate with heterologous ABC transporter proteins, e.g., ABCG5, to form a heterodimeric transporter that acts to transport cholesterol, other steroids, and other lipids out of cells. It will be recognized that derivatives, homologs, and fragments of ABCG8 can readily be used in the present invention. Such ABCG8 variants can comprise any one or more domains of the polypeptide shown as SEQ ID NO:4 or 8, or multiple copies of any one or more domains, or any number of domains in novel combinations with each other or with other proteins or protein domains.

The term "ABCG8" also refers to polymorphic variants, alleles, mutants, and interspecies homologs that: (1) have about 60% amino acid sequence identity, optionally about 75, 80, 85, 90, or 95% amino acid sequence identity to SEQ ID NO:4 or 8 over a window of about 25 amino acids, optionally 50–100 amino acids; (2) specifically bind to antibodies raised against an immunogen comprising an amino acid sequence of SEQ ID NO:4 or 8, and conservatively modified variants thereof; or (3) specifically hybridize (with a size of at least about 100, optionally at least about 500–1000 nucleotides) under stringent hybridization conditions to a sequence of SEQ ID NO:3 or 7, and conservatively modified variants thereof.

An "ABC" protein, polypeptide, nucleic acid, polynucleotide, or gene refers to any member of the ABC superfamily of transporter molecules, or to any nucleic acid encoding an ABC transporter, or to any homolog, derivative, or variant of any of the transporters or nucleic acids. An "ABC" polypeptide includes any member of the superfamily, including whole site transporters, half site transporters, or to any subfamily within the superfamily, including subfamily A, B, C, D, E, F, or G, and can be derived from any organism, including prokaryotic and eukaryotic organisms. An "ABC" transporter can be involved in the transport of any compounds, including ions, drugs, peptides, and lipids, including sterols such as cholesterol.

As used herein, an "ABCG5 protein" or "ABCG5 polypeptide" refers to a transporter as shown in SEQ ID NO:2 or 6, or any derivative, homolog, or fragment thereof, and an "ABCG5 polynucleotide" or ABCG5 nucleic acid" or "ABCG5 gene" refers to any nucleic acid encoding such a protein, derivative, homolog, or fragment thereof. It is noted that ABCG5 is also known as the "Sitosterolemia Susceptibility Gene" or "SSG" (see, U.S. Provisional Patent Application No. 60/198,465, filed Apr. 18, 2000, and No. 60/204, 234, filed May 15, 2000, the teachings of both of which are incorporated herein by reference for all purposes). ABCG5 proteins or derivatives can be expressed in any cell type, including any eukaryotic or prokaryotic cell, or synthesized in vitro. Typically, ABCG5 nucleic acids or genes encode transporters that associate with heterologous ABC transporter proteins, e.g., ABCG8, to form a heterodimeric transporter that acts to transport cholesterol, other steroids, and other lipids out of cells. It will be recognized that derivatives, homologs, and fragments of ABCG5 can readily be used in the present invention. Such ABCG5 variants can comprise any one or more domains of the polypeptide shown as SEQ ID NO:2 or 6, or multiple copies of any one or more domains, or any number of domains in novel combinations with each other or with other proteins or protein domains.

The term "ABCG5" also refers to polymorphic variants, alleles, mutants, and interspecies homologs that: (1) have about 60% amino acid sequence identity, optionally about 75, 80, 85, 90, or 95% amino acid sequence identity to SEQ ID NO:2 or 6 over a window of about 25 amino acids, optionally 50–100 amino acids; (2) specifically bind to antibodies raised against an immunogen comprising an amino acid sequence of SEQ ID NO:2 or 6, and conservatively modified variants thereof; or (3) specifically hybridize (with a size of at least about 100, optionally at least about 500–1000 nucleotides) under stringent hybridization conditions to a sequence of SEQ ID NO:1 or 5, and conservatively modified variants thereof.

Topologically, full-length ABCG5 and ABCG8 polypeptides include a "transport unit," an "ATP binding domain," "a hydrophobic domain," six "transmembrane segments," "Walker A motif" "Walker B motif," "Signature C motif" and others (see, FIG. 1). These domains can be structurally identified using methods known to those of skill in the art, such as standard sequence analysis programs and by comparison with related proteins. (see, e.g., Croop et al., (1998) *Methods in Enzymology* 292:101–162). Additional domains can be readily identified using standard methods. For example, as ABCG8 interacts with heterologous ABC family members, e.g., ABCG5, "dimerization domains" can be identified using standard methods to localize regions responsible for protein—protein interactions (e.g., cross-linking, deletion or mutation analysis, etc.).

"Biological sample," as used herein, refers to a sample of biological tissue or fluid that contains one or more ABCG8 nucleic acids encoding one or more ABCG8 proteins. Such samples include, but are not limited to, tissue isolated from humans and mice, in particular, intestine and liver. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as a chimpanzee or a human.

By "determining the functional effect" is meant assaying for a compound that modulates, e.g., increases or decreases, a parameter that is indirectly or directly under the influence of an ABCG8 polypeptide, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, changes in gene expression of ABCG8 or of any cellular activity, alterations of ABCG8 binding to heterologous proteins or other molecules, and alterations in ABCG8 activity, e.g., cholesterol transport.

"Inhibitors," "activators," and "modulators" of ABCG8 genes or proteins are used interchangeably to refer to inhibitory, activating, or modulating molecules identified using in vitro and in vivo assays for ABCG8. Inhibitors are compounds that, e.g., bind to ABCG8 proteins, partially or totally block ABCG8 activity, downregulate ABCG8 expression or stability, or prevent ABCG8 binding to heterologous molecules, e.g., ABCG5. Activators are compounds that, e.g., bind to ABCG8, stimulate ABCG8 activity, increase ABCG8 expression or stability, or facilitate ABCG8 binding to membranes or to any other protein or factor, e.g., ABCG5. Modulators may include genetically modified versions of ABCG8 proteins, e.g., dominant negative or activated forms of ABCG8. Such assays for inhibitors and activators are described below and include, e.g., expressing ABCG8 proteins in cells, applying putative modulator compounds, and then determining the functional effects of the putative modulator on ABCG8 activity. Samples or assays comprising ABCG8 polypeptides that are treated with a potential activator, inhibitor, or modulator are compared to control samples without the inhibitor, activator, or modulator to examine the effect of the candidate compound. Control samples (untreated with the compound) are typically assigned a relative ABCG8 activity value of 100%. Inhibition of an ABCG8 polypeptide is achieved when the activity value relative to the control is about 80%, optionally 50% or 25–0%. Activation of an ABCG8 polypeptide is achieved when the activity value relative to the control is 110%, optionally 150%, optionally 200–500%, or 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ABCG8 nucleic acid is separated from open reading frames that flank the ABCG8 gene and encode proteins other than ABCG8. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081(1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984)).

Another example of algorithm that is suitable for determining percent sequence identity and sequence similarity are the BLAST and BLAST 2.0 algorithms, which are described in Altschul et at., Nuc. Acids Res. 25:3389–3402 (1977) and Altschul et at., *J. Mol. Blot.* 215:403–410 (1990), respectively. Software for performing BLAST analyses is publicly available through the National Center for Biotechnology Information URL address: http file type, www host server, domain name ncbi.nlm.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et at., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci.* USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci.* USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5× SSC, and 1% SDS, incubating at 42° C., or, 5× SSC, 1% SDS, incubating at 65° C., with wash in 0.2× SSC, and 0.1% SDS at 65° C. Such washes can be performed for 5, 15, 30, 60, 120, or more minutes.

Nucleic acids that do not hybridize to each other under stringent conditions are still substantially identical if the polypeptides which they encode are substantially identical.

This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1× SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—CH$_1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see, *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4:72 (1983); Cole et al, pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-ABCG8" antibody is an antibody or antibody fragment that specifically binds a polypeptide encoded by an ABCG8 gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to an ABCG8 polypeptide from specific species such as rat, mouse, or human can be selected to obtain only those polyclonal antibodies that are specifically immunoreactive with the ABCG8 protein and not with other proteins, except for polymorphic variants and alleles of the ABCG8 protein. This selection may be achieved by subtracting out antibodies that cross-react with ABCG8 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

III. Manipulation and Detection of ABCG8 Nucleic Acids

In numerous embodiments of the present invention, nucleic acids encoding an ABCG8 polypeptide, including a full-length ABCG8 protein, or any derivative, variant, homolog, or fragment thereof, will be used. Such nucleic acids are useful for any of a number of applications, including for the production of ABCG8 protein, for diagnostic assays, for therapeutic applications, for ABCG8 specific probes, for assays for ABCG8 binding and/or modulating compounds, to identify and/or isolate ABCG8 homologs from other species, and other applications.

A. General Recombinant DNA Methods

Numerous applications of the present invention involve the cloning, synthesis, maintenance, mutagenesis, and other manipulations of nucleic acid sequences that can be performed using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., Gene 16:21–26 (1981).

B. Isolating and Detecting ABCG8 Nucleotide Sequences

In numerous embodiments of the present invention, ABCG8 nucleic acids will be isolated and cloned using recombinant methods. Such embodiments are used, e.g., to isolate ABCG8 polynucleotides for protein expression or during the generation of variants, derivatives, expression cassettes, or other sequences derived from ABCG8, to monitor ABCG8 gene expression, for the isolation or detection of ABCG8 sequences in different species, for diagnostic purposes in a patient, i.e., to detect mutations in ABCG8, or for genotyping and/or forensic applications.

Often, the nucleic acid sequences encoding ABCG8 proteins and related nucleic acid sequence homologs are cloned from cDNA and genomic DNA libraries by hybridization with probes, or isolated using amplification techniques with oligonucleotide primers. For example, ABCG8 sequences are typically isolated from mammalian nucleic acid (genomic or cDNA) libraries by hybridizing with a nucleic acid probe, the sequence of which can be derived from SEQ ID NO:3 or 7, or amplified using primers designed from SEQ ID NO:3 or 7. A suitable biological material from which RNA and cDNA for ABCG8 can be isolated is, e.g., intestine, liver, or macrophages.

Amplification techniques using primers can also be used to amplify and isolate ABCG8 sequences from DNA or RNA (see, e.g., Dieffenfach & Dveksler, *PCR Primer: A Laboratory Manual* (1995)). Primers can be used, e.g., to amplify either the full length sequence or a probe of from one to several hundred nucleotides (using, e.g., primers designed from SEQ ID NOs:3 or 7), which is then used to screen a mammalian library for full-length ABCG8 clones.

Nucleic acids encoding ABCG8 polypeptides can also be isolated from expression libraries using antibodies as probes. Such polyclonal or monoclonal antibodies can be raised using the sequence of SEQ ID NO:4 or 8, or derivatives or fragments thereof.

Polymorphic variants, alleles, and interspecies homologs that are substantially identical to an ABCG8 gene can be isolated using ABCG8 nucleic acid probes, and oligonucleotides under stringent hybridization conditions, by screening libraries. Alternatively, expression libraries can be used to clone ABCG8 polymorphic variants, alleles, and interspecies homologs, by detecting expressed homologs immunologically with antisera or purified antibodies made against an ABCG8 polypeptide, which also recognize and selectively bind to the ABCG8 homolog.

More distantly related ABCG8 homologs can be identified using any of a number of well known techniques, including by hybridizing an ABCG8 probe with a genomic or cDNA library using moderately stringent conditions, or under low stringency conditions. Also, a distant homolog can be amplified from a nucleic acid library using degenerate primer sets, i.e., primers that incorporate all possible codons encoding a given amino acid sequence, in particular based on a highly conserved amino acid stretch. Such primers are well known by those of skill, and numerous programs are available, e.g., on the Internet, for degenerate primer design.

To make a cDNA library, one should choose a source that is rich in ABCG8 mRNA, e.g., cells isolated from the intestine, the liver, or macrophage cells. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue or cells and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.,* 72:3961–3965 (1975).

An alternative method of isolating ABCG8 nucleic acid and its homologs combines the use of synthetic oligonucleotide primers and amplification of an RNA or DNA template (see, U.S. Pat. Nos. 4,683,195 and 4,683,202; PCR *Protocols: A Guide to Methods and Applications* (Innis et al., eds, 1990)). Methods such as polymerase chain reaction (PCR) and ligase chain reaction (LCR) can be used to amplify nucleic acid sequences of ABCG8 genes directly from mRNA, from cDNA, from genomic libraries or cDNA libraries. Degenerate oligonucleotides can be designed to amplify ABCG8 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of ABCG8-encoding mRNA in physiological samples, for nucleic acid sequencing, or for other purposes. Genes amplified by the PCR reaction can be purified from agarose gels and cloned into an appropriate vector.

Synthetic oligonucleotides can be used to construct recombinant ABCG8 genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of the ABCG8 nucleic acid. The specific subsequence is then ligated into an expression vector.

The nucleic acid encoding an ABCG8 polypeptide is typically cloned into intermediate vectors before transformation into prokaryotic or eukaryotic cells for replication and/or expression. These intermediate vectors are typically prokaryote vectors, e.g., plasmids, or shuttle vectors. Vectors, cells, and transfection methods are well known to those of skill and are described, e.g., in Ausubel or in Sambrook, both supra.

Optionally, nucleic acids will be used that encode chimeric proteins comprising an ABCG8 polypeptide or domains thereof in combination with a heterologous polypeptide or polypeptides. For example, a domain such as an ATP binding domain, a transmembrane domain, a transport unit, or a dimerization domain, can be covalently linked to a heterologous protein such as a heterologous transmembrane domain, transport unit, etc. Other heterologous proteins of choice include a marker protein, e.g., luciferase, green fluorescent protein (GFP), and β-gal, each of which is well known in the art.

In certain embodiments, ABCG8 polynucleotides will be detected using hybridization-based methods to determine, e.g., ABCG8 RNA levels or to detect particular DNA sequences, e.g., for diagnosis, for genotyping, or for forensic applications. For example, gene expression of ABCG8 can be analyzed by techniques known in the art, e.g., Northern blotting, reverse transcription and amplification of mRNA, dot blotting, in situ hybridization, RNase protection, probing DNA microchip arrays, and the like. In one embodiment, high density oligonucleotide analysis technology (e.g., GeneChip™) is used to identify homologs and polymorphic variants of ABCG8, or to monitor levels of ABCG8 mRNA. In the case where a homolog is linked to a known disease, they can be used with GeneChip™ as a diagnostic tool in detecting the disease in a biological sample, see, e.g., Gunthand et al., *AIDS Res. Hum. Retroviruses* 14:869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

In certain applications, an ABCG8 DNA sequence will be detected, e.g., for diagnostic or forensic applications. For example, an ABCG8 allele can be detected in a mammal using Southern blot hybridization, i.e., by isolating genomic DNA, performing a restriction digest on the isolated DNA, separating the restriction fragments electrophoretically, e.g., in an agarose gel, and transferring the separated DNA to a membrane and probing with a specific, labeled sequence. Southern blotting is well known to those of skill, and is taught in numerous sources, including Ausubel et al. and Sambrook et al.

In other embodiments, e.g., to detect tissue specific or temporal patterns of gene expression, an ABCG8 polynucleotide is detected using in situ hybridization. In in situ hybridization, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987).

C. Expression in Prokaryotes and Eukaryotes

Often, a cloned ABCG8 sequence will be expressed in a prokaryotic or eukaryotic cell to obtain expression, i.e., production of the encoded mRNA or protein. For example, in numerous embodiments, an ABCG8 polynucleotide will be introduced into a cell to modulate the level of ABCG8 activity in the cell, and thereby to modulate the level of cholesterol transport in cells of a patient, or dietary sterol absorption in the patient. To obtain high level expression of a cloned gene or nucleic acid, such as a cDNA encoding an ABCG8 polypeptide, an ABCG8 sequence is typically subcloned into an expression vector that contains a strong promoter to direct transcription, a transcription/translation terminator, and, if for a nucleic acid encoding a protein, a ribosome binding site for translational initiation. Suitable bacterial promoters are well known in the art and are described, e.g., in Sambrook et al. and Ausubel et al. Bacterial expression systems for expressing the ABCG8 protein are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

For therapeutic applications, ABCG8 nucleic acids are introduced into a cell, in vitro, in vivo, or ex vivo, using any of a large number of methods including, but not limited to, infection with viral vectors, liposome-based methods, biolistic particle acceleration (the gene gun), and naked DNA injection. Such therapeutically useful nucleic acids include, but are not limited to, coding sequences for full-length ABCG8, coding sequences for an ABCG8 fragment, domain, derivative, or variant, ABCG8 antisense sequences, and ABCG8 ribozymes. Typically, such sequences will be operably linked to a promoter, but in numerous applications a nucleic acid will be administered to a cell that is itself directly therapeutically effective, e.g., certain antisense or ribozyme molecules.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the ABCG8-encoding nucleic acid in host cells. A typical expression cassette thus contains a promoter operably linked to the nucleic acid sequence encoding an ABCG8 polypeptide, and signals required for efficient polyadenylation of the transcript, ribosome binding sites, and translation termination. The nucleic acid sequence encoding an ABCG8 polypeptide may be linked to a cleavable signal peptide sequence to promote secretion of the encoded protein by the transfected cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc, HA-tag, 6-His (SEQ ID NO: 11) tag, maltose binding protein, VSV-G tag, anti-DYKDDDDK (SEQ ID NO:12) tag, or any such tag, a large number of which are well known to those of skill in the art.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding an ABCG8 polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of an ABCG8 protein, which are then purified using standard techniques (see, e.g., Colley et al., *J. Biol. Chem.* 264:17619–17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, Methods in Enzymology 101:347–362 (Wu et al., eds, 1983).

Any of the well known procedures for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing an ABCG8 gene.

After the expression vector is introduced into the cells, the transfected cells are cultured under conditions favoring expression of the ABCG8 polypeptide, which is recovered from the culture using standard techniques identified below. Methods of culturing prokaryotic or eukaryotic cells are well known and are taught, e.g., in Ausubel et al., Sambrook et al., and in Freshney, *Culture of Animal Cells,* 3d. Ed., (1993), A Wiley-Liss Publication.

IV. Purification of ABCG8 Polypeptides

Either naturally occurring or recombinant ABCG8 polypeptides can be purified for use in functional assays, binding assays, diagnostic assays, and other applications. Optionally, recombinant ABCG8 polypeptides are purified. Naturally occurring ABCG8 polypeptides are purified, e.g., from mammalian tissue such as macrophages, liver, or intestine, or any other source of an ABCG8 homolog. Recombinant ABCG8 polypeptides are purified from any suitable bacterial or eukaryotic expression system, e.g., CHO cells or insect cells.

ABCG8 proteins may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant ABCG8 polypeptide is being purified. For example, proteins having established molecular adhesion properties can be reversibly fused to the ABCG8 polypeptide. With the appropriate ligand, an ABCG8 polypeptide can be selectively adsorbed to a purification column and then freed from the column in a relatively pure form. The fused protein is then removed by enzymatic activity. ABCG8 proteins can also be purified using immunoaffinity columns.

A. Purification of ABCG8 Protein from Recombinant Cells

Recombinant proteins are expressed by transformed bacteria or eukaryotic cells such as CHO cells or insect cells in large amounts, typically after promoter induction; but expression can be constitutive. Promoter induction with IPTG is one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of ABCG8 inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of immunologically and/or biologically active protein. Other suitable buffers are known to those skilled in the art. ABCG8 polypeptides are separated from other bacterial proteins by standard separation techniques, e.g., with Ni-NTA agarose resin.

Alternatively, it is possible to purify ABCG8 polypeptides from bacteria periplasm. After lysis of the bacteria, when an ABCG8 protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying ABCG8 Polypeptides

1. Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of an ABCG8 protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

ABCG8 proteins can also be separated from other proteins on the basis of its size, net surface charge, hydrophobicity, and affinity for heterologous molecules. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

IV. Antibodies to ABCG8 Family Members

In numerous embodiments of the present invention, antibodies that specifically bind to ABCG8 polypeptides will be used. Such antibodies have numerous applications, including for the modulation of ABCG8 activity and for immunoassays to detect ABCG8, and variants, derivatives, fragments, etc. of ABCG8. Immunoassays can be used to qualitatively or quantitatively analyze the ABCG8 polypeptide. A general overview of the applicable technology can be found in Harlow & Lane, Antibodies: A Laboratory Manual (1988).

Methods of producing polyclonal and monoclonal antibodies that react specifically with ABCG8 polypeptides are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of ABCG8-comprising immunogens may be used to produce antibodies specifically reactive with an ABCG8 polypeptide. For example, a recombinant ABCG8 protein, or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the ABCG8 polypeptide. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-ABCG8 proteins, or even related proteins from other organisms, using a competitive binding immunoassay. Specific polyclonal antisera and monoclonal antibodies will usually bind with a $K_d$ of at least about 0.1 mM, more usually at least about 1 $\mu$M, optionally at least about 0.1 $\mu$M or better, and optionally 0.01 $\mu$M or better.

Using ABCG8-specific antibodies, individual ABCG8 proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

C. Immunological Binding Assays

ABCG8 proteins can be detected and/or quantified using any of a number of well recognized immunological binding assays (see, e.g., U.S. Pat. Nos. 4,366,241; 4,376,110; 4,517,288; and U.S. Pat. No. 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case an ABCG8 protein or an antigenic subsequence thereof). The antibody (e.g., anti-ABCG8) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled ABCG8 polypeptide or a labeled anti-ABCG8 antibody. Alternatively, the labeling agent may be a third moiety, such a secondary antibody, that specifically binds to the antibody/ABCG8 complex (a secondary antibody is typically specific to antibodies of the species from which the first antibody is derived). Other proteins capable of specifically binding immunoglobulin constant regions, such as protein A or protein G, may also be used as the label agent. These proteins exhibit a strong nonimmunogenic reactivity with immunoglobulin constant regions from a variety of species (see, e.g., Kronval et al.,*J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Noncompetitive Assay Formats

Immunoassays for detecting an ABCG8 protein in a sample may be either competitive or noncompetitive. Noncompetitive immunoassays are assays in which the amount of antigen is directly measured. In one preferred "sandwich" assay, for example, the anti-ABCG8 antibodies can be bound directly to a solid substrate on which they are immobilized. These immobilized antibodies then capture the ABCG8 protein present in the test sample. The ABCG8 protein is thus immobilized is then bound by a labeling agent, such as a second ABCG8 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

2. Competitive Assay Formats

In competitive assays, the amount of ABCG8 protein present in the sample is measured indirectly by measuring the amount of a known, added (exogenous) ABCG8 protein displaced (competed away) from an anti-ABCG8 antibody by the unknown ABCG8 protein present in a sample. In one competitive assay, a known amount of ABCG8 protein is added to a sample and the sample is then contacted with an antibody that specifically binds to the ABCG8 protein. The amount of exogenous ABCG8 protein bound to the antibody is inversely proportional to the concentration of ABCG8 protein present in the sample. In a particularly preferred embodiment, the antibody is immobilized on a solid substrate. The amount of ABCG8 protein bound to the antibody may be determined either by measuring the amount of ABCG8 protein present in an ABCG8/antibody complex, or alternatively by measuring the amount of remaining uncomplexed protein. The amount of ABCG8 protein may be detected by providing a labeled ABCG8 molecule.

A hapten inhibition assay is another preferred competitive assay. In this assay the known ABCG8 protein is immobilized on a solid substrate. A known amount of anti-ABCG8 antibody is added to the sample, and the sample is then contacted with the immobilized ABCG8. The amount of anti-ABCG8 antibody bound to the known immobilized ABCG8 protein is inversely proportional to the amount of ABCG8 protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Cross-Reactivity Determinations

Immunoassays in the competitive binding format can also be used for crossreactivity determinations. For example, a protein at least partially encoded by SEQ ID NO:3 or 7 can be immobilized to a solid support. Proteins (e.g., ABCG8 proteins and homologs) are added to the assay that compete for binding of the antisera to the immobilized antigen. The ability of the added proteins to compete for binding of the antisera to the immobilized protein is compared to the ability of the ABCG8 polypeptide encoded by SEQ ID NO:3 or 7 to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an ABCG8 protein, to the immunogen protein (i.e., ABCG8 protein encoded by SEQ ID NO:3 or 7). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:3 or 7 that is required to inhibit 50% of binding, then the second protein is said to specifically bind to the polyclonal antibodies generated to an ABCG8 immunogen.

Polyclonal antibodies that specifically bind to an ABCG8 protein from a particular species can be made by subtracting out cross-reactive antibodies using ABCG8 homologs. For example, antibodies specific to human ABCG8 (SEQ ID NO:8) can be made by subtracting out antibodies that are cross-reactive with mouse ABCG8 (SEQ ID NO:4). In an analogous fashion, antibodies specific to a particular ABCG8 protein can be obtained in an organism with multiple ABCG8 genes.

4. Other Assay Formats

Western blot (immunoblot) analysis is used to detect and quantify the presence of ABCG8 protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the ABCG8 protein. The anti-ABCG8 polypeptide antibodies specifically bind to the ABCG8 polypeptide on the solid support. These antibodies may be directly labeled or alternatively may be subsequently detected using labeled antibodies (e.g., labeled sheep anti-mouse antibodies) that specifically bind to the anti-ABCG8 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

5. Reduction of Nonspecific Binding

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such nonspecific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

6. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Nonradioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize an ABCG8 protein, or secondary antibodies that recognize anti-ABCG8.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g. luminol. For a review of various labeling or signal producing systems that may be used, see, e.g., U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

V. Modulating ABCG8 Activity in Cells

A. Assays for Modulators of ABCG8 Proteins

In numerous embodiments of this invention, the level of ABCG8 activity will be modulated in a cell by administering to the cell, in vivo or in vitro, any of a large number of ABCG8-modulating molecules, e.g., polypeptides, antibodies, amino acids, nucleotides, lipids, carbohydrates, or any organic or inorganic molecule. Such ABCG8 modulators are particularly useful in the treatment of any of a large number of diseases and conditions.

To identify molecules capable of modulating ABCG8, assays will be performed to detect the effect of various compounds on ABCG8 activity in a cell. Such assays can involve the identification of compounds that interact with ABCG8 proteins, either physically or genetically, and can thus rely on any of a number of standard methods to detect physical or genetic interactions between compounds. Such assays can also involve the identification of compounds that affect ABCG8 expression, activity or other properties, such as its phosphorylation or ability to bind other proteins. Such assays can also involve the detection of ABCG8 activity in a cell, either in vitro or in vivo, and can thus involve the detection of, e.g., cholesterol transport into and out of a cell. Such cell-based assays can be performed in any type of cell, e.g., a cell that naturally expresses ABCG8, or a cultured cell that produces ABCG8 due to recombinant expression.

It will be appreciated that any of the herein-described assays to identify modulators of ABCG8 can also be used to identify modulators of LXR or RXR which, as described infra, are thought to regulate the expression of ABCG8 and other ABC transporters. Such LXR and RXR transporters are thus useful for the treatment or prevention of any of the herein-described diseases and conditions.

B. Assays for ABCG8-Interacting Compounds

In certain embodiments, assays will be performed to identify molecules that physically or genetically interact with ABCG8 proteins. Such molecules can be any type of molecule, including polypeptides, polynucleotides, amino acids, nucleotides, carbohydrates, lipids, or any other organic or inorganic molecule. Such molecules may represent molecules that normally interact with ABCG8 to effect sterol transport, or may be synthetic or other molecules that are capable of interacting with ABCG8 and that can potentially be used to modulate ABCG8 activity in cells, or used as lead compounds to identify classes of molecules that can interact with and/or modulate ABCG8. Such assays may represent physical binding assays, such as affinity chromatography, immunoprecipitation, two-hybrid screens, or other binding assays, or may represent genetic assays as described infra.

In any of the binding or functional assays described herein, in vivo or in vitro, any ABCG8 protein, or any derivative, variation, homolog, or fragment of an ABCG8 protein, can be used. Preferably, the ABCG8 protein is at least about 70% identical to SEQ ID NO:4 or 8. In numerous embodiments, a fragment of an ABCG8 protein is used. For example, a fragment that contains, for example, only a transport unit, an ATP binding domain, a dimerization domain, Walker A motif, Walker B motif, Signature C motif, a P loop, a transmembrane region, or any other subdomain or region of ABCG8, can be used. Such fragments can be used alone, in combination with other ABCG8 fragments, or in combination with sequences from heterologous proteins, e.g., the fragments can be fused to a heterologous polypeptide, thereby forming a chimeric polypeptide.

1. Assays for Physical Interactions

Compounds that interact with ABCG8 proteins can be isolated based on an ability to specifically bind to an ABCG8 protein or fragment thereof. In numerous embodiments, the ABCG8 protein or protein fragment will be attached to a solid support. In one embodiment, affinity columns are made using the ABCG8 polypeptide, and physically-interacting molecules are identified. It will be apparent to one of skill that chromatographic techniques can be performed at any scale and using equipment from many different manufacturers (e.g., Pharmacia Biotech). In addition, molecules that interact with ABCG8 proteins in vivo can be identified by co-immunoprecipitation or other methods, i.e., immunoprecipitating ABCG8 proteins using anti-ABCG8 antibodies from a cell or cell extract, and identifying compounds, e.g., proteins, that are precipitated along with the ABCG8 protein. Such methods are well known to those of skill in the art and are taught, e.g., in Ausubel et al., Sambrook et al., Harlow & Lane, all supra.

Two-hybrid screens can also be used to identify polypeptides that interact in vivo with an ABCG8 polypeptide or a fragment thereof (Fields et al., *Nature* 340:245–246 (1989)). Such screens comprise two discrete, modular domains of a transcription factor protein, e.g., a DNA binding domain and a transcriptional activation domain, which are produced in a cell as two separate polypeptides, each of which also comprises one of two potentially binding polypeptides. If the two potentially binding polypeptides in fact interact in vivo, then the DNA binding and the transcriptional activating domain of the transcription factor are united, thereby producing expression of a target gene in the cell. The target gene typically encodes an easily detectable gene product, e.g., β-galactosidase, GFP, or luciferase, which can be detected using standard methods. In the present invention, an ABCG8 polypeptide is fused to one of the two domains of the transcription factor, and the potential ABCG8-binding polypeptides (e.g., encoded by a cDNA library) are fused to the other domain. Such methods are well known to those of skill in the art, and are taught, e.g., in Ausubel et al., supra.

In other preferred embodiments, an assay such as the fluorescence polarization assay or the fluorescence resonance energy transfer assay is employed to identify candidate modulators. These assays do not require the separation of bound and free labeled test compound. Fluorescence polarization (FP) or fluorescence anisotropy is a useful tool for the study of molecular interactions (see, e.g. URL address: http file type, www host server, domain name panvera.com/tech/appguide/fpintro.html, Nov. 4, 1999). First, a molecule labeled with a fluorophore is excited with plane polarized light. If the fluorescent molecule stays stationary while in the excited state, light is emitted in the same polarized plane. If the excited fluorescently labeled molecule rotates out of the plane of the polarized light while in the excited state, light is emitted from the molecule in a different plane. For example, if vertical polarized light is used to excite the fluorophore, the emission spectra can be monitored in the vertical and horizontal planes. Fluorescence polarization is calculated as shown in the following Formula I:

$$\text{Fluorescent polarization} = P = (Int\ \ddot{y} - Int\ddot{y}) / (Int\ \ddot{y} + Int\ddot{y}) \quad \text{I}$$

In Formula I, Int $\ddot{y}$ is the intensity of the emission parallel to the excitation plane. Int$\ddot{y}$ is the intensity of the emission perpendicular to the excitation plane.

A small fluorescently labeled molecule, when free in solution, can emit depolarized light when excited with the proper wavelength of light. If, however, the molecule (e.g., a ligand) binds to a second molecule (e.g., a receptor) the fluorescently labeled molecule is more constrained so the light emitted is more polarized and the fluorescence polarization (FP) value is higher. Thus, a higher FP value indicates that the fluorescently labeled molecule is able to bind to the second molecule. A competition assay also can be performed using FP. If an unlabeled molecule is present in the solution, then it will compete for binding to the second molecule, e.g., the antibody and the FP value will be decreased. Thus, FP can be used in competitive assays.

Commercial assays exist to test the affinity of compounds for human estrogen receptor using a fluorescently labeled estrogen compound (see, Panvera, (Madison, Wis.) publications Lit.#'s L0069, L0082, L0084, L0095, L0072, L0085). Similarly, test compounds can be fluorescently labeled with a fluorophore that is active in a FP assay. For example, N-terminal amines of proteins, peptide, or peptide analogs can be labeled with fluorescein (Panvera, publications Lit. # L0057 and L0059) or a small fluorescent compound. Briefly, a fluorescein-$C_6$-succinimidyl ester can be conjugated to peptides or proteins. The fluorescein labeled peptide/protein can then be purified from the unreacted fluorescein-C6-succinimidyl ester using thin-layer chromatography or gel filtration chromatography. If the labeled test compound can bind to a polypeptide that has an ABCG8 binding domain, the level of polarization is increased.

Alternatively, a test compound can be screened for its ability to decrease the FP of a fluorescently labeled known ABCG8 binding protein complexed with an ABCG8 polypeptide. Briefly, a known ABCG8 binding protein is labeled with a fluorescent moiety. A test compound that decreases the FP value of the fluorescently labeled ABCG8 binding protein and ABCG8 is displacing or inhibiting the ability of the fluorescently labeled ABCG8 binding protein to bind to the ABCG8.

Methods employing the technique of fluorescence resonance energy transfer (FRET) can be employed using the methods and compositions of the present invention. FRET occurs between two fluorophores when the excitation of the donor fluorophore is transferred to the acceptor fluorophore. This interaction is dependent on the distance between the donor and acceptor fluorophore and distance-dependent interaction between a donor and acceptor molecule. The donor and acceptor molecules are fluorophores. If the fluorophores have excitation and emission spectra that overlap, then in close proximity (typically around 10–100 angstroms) the excitation of the donor fluorophore is transferred to the acceptor fluorophore. The relative proximity of the first and second labels is determined by measuring a change in the intrinsic fluorescence of the first or second label. Commonly, the emission of the first label is quenched by proximity of the second label.

Many appropriate interactive labels for FRET are known. For example, fluorescent labels, dyes, enzymatic labels, and antibody labels are all appropriate. Examples of preferred interactive fluorescent label pairs include terbium chelate and TRITC (tetrarhodamine isothiocyanate), europium cryptate and allophycocyanin and many others known to one of skill. Similarly, two colorimetric labels can result in combinations that yield a third color, e.g., a blue emission in proximity to a yellow emission produces an observed green emission.

With regard to preferred fluorescent pairs, there are a number of fluorophores which are known to quench each other. Fluorescence quenching is a bimolecular process that reduces the fluorescence quantum yield, typically without changing the fluorescence emission spectrum. Quenching can result from transient excited interactions, (collisional quenching) or, e.g., from the formation of nonfluorescent ground state species. Self-quenching is the quenching of one fluorophore by another; it tends to occur when high concentrations, labeling densities, or proximity of labels occurs. Some excited fluorophores interact to form excimers, which are excited state dimers that exhibit altered emission spectra (e.g., phospholipid analogs with pyrene sn-2 acyl chains); See Haugland (1996) Handbook of Fluorescent Probes and Research Chemicals, published by Molecular Probes, Inc., Eugene, Oreg.

The Forster radius ($R_o$) is the distance between fluorescent pairs at which energy transfer is 50% efficient (i.e., at which 50% of excited donors are deactivated by FRET). The magnitude of $R_o$ is dependent on the spectral properties of donor and acceptor dyes: $R_o = [8.8 \times 10^{23} \cdot K^2 \cdot n^{-4} \cdot QY_D \cdot J(\ )]^{1/6}$ Å; where $K^2$=dipole orientation range factor (range 0 to 4, $K^2 = 2/3$ for randomly oriented donors and acceptors); $QY_D$= fluorescence quantum yield of the donor in the absence of the acceptor; n=refractive index; and J(1)=spectral overlap integral=$\ddot{y}_A(\ ) \cdot F_D \cdot (4) d\ cm^3 M^{-1}$, where $_A$=extinction coefficient of acceptor and $F_D$=fluorescence emission intensity of donor as a fraction of total integrated intensity. Some typical $R_o$ are listed for typical donor acceptor pairs in Table 1:

TABLE 1

| Donor | Acceptor | $R_o$ ($\ddot{y}$) |
|---|---|---|
| Fluorescein | Tetramethylrhodamine | 55 |
| IAEDANS | Fluorescein | 46 |
| EDANS | DABCYL | 33 |
| BODIPY FL | BODIPY FL | 57 |
| Fluorescein | QSY-7 dye | 61 |

An extensive compilation of $R_o$ values are found in the literature; see Haugland (1996), supra. In most uses, the donor and acceptor dyes are different, in which case FRET can be detected by the appearance of sensitized fluorescence of the acceptor or by quenching of the donor fluorescence. When the donor and acceptor are the same, FRET is detected by the resulting fluorescence depolarization.

In addition to quenching between fluorophores, individual fluorophores are also quenched by nitroxide-labeled molecules such as fatty acids. Spin labels such as nitroxides are also useful in the liquid phase assays of the invention.

Test compounds and an ABCG8 polypeptide can be labeled with FRET pairs. If the test compound can directly interact with the ABCG8 polypeptide, fluorescence resonance energy transfer can take place and the affinity can be measured. Alternatively, a known ABCG8 binding protein can be labeled with an appropriate FRET label and incubated with an FRET fluorophore labeled polypeptide that includes an ABCG8. Fluorescence resonance energy transfer can take place between the labeled ABCG8 binding protein and the labeled ABCG8. If a test compound were incubated with the two labeled components, the amount of FRET would be lowered if the test compound can inhibit or displace the binding of the labeled ABCG8 binding protein to the ABCG8.

Additional methods for assaying the ability of test compounds to modulate ABCG8 interactions with other proteins employ peptide sensors. These assays can be adapted from those described in WO 99/27365. Briefly, these assays use a peptide sensor to which is attached a detectable label. The peptides can be naturally occurring peptides that interact with ABCG8, or can be obtained through randomizing residues and selecting for binding to the ABCG8 polypeptide. Panels of predetermined or randomized candidate sensors can be screened for ABCG8 binding.

In typical embodiments, the sensor peptides are labeled with a detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry,* 2nd ed., Springer Verlag, N.Y. and in Haugland (1996) *Handbook of Fluorescent Probes and Research Chemicals,* a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., 3H, 125I, 35S, 14C, 32P, 33P, etc.), enzymes (e.g., horse radish peroxidase, alkaline phosphatase etc.), spectral colorimetric labels such as colloidal gold or colored glass or plastic (e.g., polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions. In a presently preferred embodiment, the detectable label is a fluorescent label, in which case fluorescence polarization detection provides a sensitive and efficient means of detecting whether the peptide sensor is bound to the ABCG8 polypeptide. See, e.g., Schindler et al. (1995) *Immunity* 2:689–697).

The sensor peptide and the ABCG8 polypeptide are incubated under conditions that are suitable for sensor binding to the ABCG8 polypeptide. In some embodiments, a candidate modulator of ABCG8 binding to a corepressor, coactivator or other ligand is included in the reaction mixture. If a candidate modulator increases or decreases binding of the sensor peptide to the ABCG8 polypeptide, the candidate modulator is a potential lead compound for modulating ABCG8-mediated sterol transport in cells.

C. Assays for ABCG8 Protein Activity

ABCG8 genes and their alleles and polymorphic variants encode transporters that promote the translocation of cholesterol and other sterols, as well as other lipids, across cell membranes, e.g., from the cytoplasm to the cell exterior. Accordingly, the activity of ABCG8 polypeptides can be assessed using a variety of in vitro and in vivo assays to determine functional, chemical, and physical effects, e.g., directly measuring the cholesterol or other lipid transport into and out of cells, measuring ABCG8 protein and/or RNA levels, or measuring other aspects of ABCG8 polypeptides, e.g., phosphorylation levels, transcription levels, and the like. Such assays can be used to test for both activators and inhibitors of ABCG8 proteins. Modulators can also be genetically altered versions of ABCG8 proteins, e.g., dominant negative forms of ABCG8 or of proteins that interact with ABCG8, e.g., ABCG5. Such modulators of activity are useful for, e.g., many diagnostic and therapeutic applications.

Any assays for cholesterol transport can be used in the present invention. For example, to assess the level of cholesterol (or other sterol or lipid) efflux in cells in culture, radioactively labeled cholesterol, e.g., $^{14}$C-cholesterol, is added to culture medium, and the amount of labeled cholesterol in the cell (e.g., in cell lysates) or outside of the cell (e.g., in culture medium) in the presence or absence of a test agent is detected. (see, e.g., Klucken et al., (2000) *PNAS* 97:817–822).

Other, animal-based models of ABCG8 activity can also be used. For example, a given amount of radiolabeled $^{14}$C-cholesterol is added to the diet of a mammal that also contains a test agent. The ability of the test agent to affect the level of cholesterol absorption is then assayed by monitoring the amount of labeled cholesterol taken up by the intestine of the mammal. In addition, the ability of any test agent can be assessed by virtue of an alteration in any characteristic of sitosterolemia, e.g., atherosclerosis, xanthomas, arthritis, chronic hemolytic anemia, etc.

The ABCG8 protein of any of the herein-described assays will typically be a recombinant or naturally occurring polypeptide with a sequence of SEQ ID NO:4 or 8 or conservatively modified variants thereof. Alternatively, the ABCG8 protein of the assay will be derived from a eukaryote and include an amino acid subsequence having amino acid sequence identity to SEQ ID NO:4 or 8. Generally, the amino acid sequence identity will be at least 60%, optionally at least 70% to 85%, optionally at least 90–95%. Optionally, the polypeptide of the assays will comprise a domain of an ABCG8 protein, such as a transport unit, ATP binding domain, or transmembrane domain. In certain embodiments, a domain of an ABCG8 protein is bound to a solid substrate and used, e.g., to isolate any molecules that can bind to and/or modulate their activity. In certain embodiments, a domain of an ABCG8 polypeptide is fused to a heterologous polypeptide, thereby forming a chimeric polypeptide. Such chimeric polypeptides are also useful, e.g., in assays to identify modulators of ABCG8.

Samples or assays that are treated with a potential ABCG8 protein inhibitor or activator are compared to control samples without the test compound, to examine the extent of modulation. Control samples (untreated with activators or inhibitors) are assigned a relative ABCG8 activity value of 100. Inhibition of an ABCG8 protein is achieved when the ABCG8 activity value relative to the control is about 90%, optionally 50%, optionally 25–0%. Activation of an ABCG8 protein is achieved when the ABCG8 activity value relative to the control is 110%, optionally 150%, 200–500%, or 1000–2000%.

The effects of the test compounds upon the function of the polypeptides can be measured by examining any of the parameters described above. Any suitable physiological change that affects ABCG8 activity can be used to assess the influence of a test compound on the polypeptides of this invention.

In another preferred embodiment, a "knock-in" assay is used in which the coding sequence for a marker gene, e.g., luciferase or GFP, is used to replace, e.g., by homologous recombination, the coding sequence for a gene of interest, e.g., ABCG8, in a cell. In this way, the marker gene serves as a direct reporter for the expression of the gene of interest. In a typical such embodiment, a coding sequence for an ABCG8 gene is replaced by homologous recombination with a coding sequence for luciferase in a mammalian cell. The cell is then exposed to a test agent and the expression of the luciferase is detected, preferably in a homogeneous format, most preferably using high throughput screening methods.

D. Modulators and Binding Compounds

The compounds tested as modulators of an ABCG8 protein can be any small chemical compound, or a biological entity, such as a protein, sugar, nucleic acid or lipid. Alternatively, modulators can be genetically altered versions of a ABCG8 gene. Typically, test compounds will be small chemical molecules and peptides. Essentially any chemical compound can be used as a potential modulator or binding compound in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. *J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. No. 5,525,735 and U.S. Pat. No. 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

1. Solid State and Soluble High Throughput Assays

In one embodiment, the invention provides soluble assays using an ABCG8 polypeptide, or fragment thereof, either alone or covalently linked to a heterologous protein to create a chimeric molecule. In another embodiment, the invention provides solid phase based in vitro assays in a high throughput format, where a domain, chimeric molecule, ABCG8 protein, or cell or tissue expressing an ABCG8 protein is attached to a solid phase substrate.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000–20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly poly-gly sequences of between about 5 and 200 amino acids (SEQ ID NO:13). Such flexible linkers are known to persons of skill in the art. For example, poly (ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:6031–6040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996)(all describing arrays of biopolymers fixed to solid substrates). Nonchemical approaches for fixing tag binders to substrates include other common methods, such as heat, cross-linking by UV radiation, and the like.

2. Computer-Based Assays

Yet another assay for compounds that modulate ABCG8 protein activity involves computer assisted drug design, in which a computer system is used to generate a three-dimensional structure of an ABCG8 protein based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind. These regions are then used to identify compounds that bind to the protein.

The three-dimensional structural model of the protein is generated by entering protein amino acid sequences of at least 10 amino acid residues or corresponding nucleic acid sequences encoding an ABCG8 polypeptide into the computer system. The nucleotide sequence encoding the polypeptide preferably comprises SEQ ID NO:3 or SEQ ID NO:7, and conservatively modified versions thereof. The amino acid sequence, preferably comprising SEQ ID NO:4 or 8, or conservatively modifies versions thereof, represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential modulator binding regions are identified by the computer system. Three-dimensional structures for potential modulators are generated by entering amino acid or nucleotide sequences or chemical formulas of compounds, as described above. The three-dimensional structure of the potential modulator is then compared to that of the ABCG8 protein to identify compounds that bind to the protein. Binding affinity between the protein and compound is determined using energy terms to determine which compounds have an enhanced probability of binding to the protein.

Computer systems are also used to screen for mutations, polymorphic variants, alleles and interspecies homologs of ABCG8 genes. Such mutations can be associated with disease states or genetic traits. As described above, Gene-Chip™ and related technology can also be used to screen for mutations, polymorphic variants, alleles and interspecies homologs. Once the variants are identified, diagnostic assays can be used to identify patients having such mutated genes. Identification of the mutated ABCG8 genes involves receiving input of a first nucleic acid sequence of SEQ ID NO:3 or 7, or a first amino acid sequence of SEQ ID NO:4 or 8, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various ABCG8 genes, and mutations associated with disease states and genetic traits.

VI. Modulating ABCG8 Activity/Expression to Treat Diseases or Conditions.

In numerous embodiments of this invention, a compound, e.g., nucleic acid, polypeptide, or other molecule is administered to a patient, in vivo or ex vivo, to effect a change in ABCG8 activity or expression in the patient. Such compounds can be nucleic acids encoding full length ABCG8 polypeptides, e.g., as shown as SEQ ID NO:4 or 8, or any derivative, fragment, or variant thereof, operably linked to a promoter. Suitable nucleic acids also include inhibitory sequences such as antisense or ribozyme sequences, which can be delivered in, e.g., an expression vector operably linked to a promoter, or can be delivered directly. Also, any nucleic acid that encodes a polypeptide that modulates the expression of ABCG8 can be used. In general, nucleic acids can be delivered to cells using any of a large number of vectors or methods, e.g., retroviral, adenoviral, or adeno-associated virus vectors, liposomal formulations, naked DNA injection, and others. All of these methods are well known to those of skill in the art.

Proteins can also be delivered to a patient to modulate ABCG8 activity. In preferred embodiments, a polyclonal or monoclonal antibody that specifically binds to ABCG8, particularly to an ATP binding domain, a tranport unit, or a dimerization domain, will be delivered. In addition, any polypeptide that interacts with and/or modulates ABCG8 activity can be used, e.g., a polypeptide that is identified using the presently described assays, or any dominant negative form of ABCG8 or an ABCG8-interacting protein, e.g., ABCG5, etc. In addition, any polypeptides that affect ABCG8 expression can be used.

Further, any compound that is found to or designed to interact with and/or modulate the activity of ABCG8 can be used. For example, any compound that is found, using the methods described herein, to bind to or modulate the activity of ABCG8 can be used.

In a preferred embodiment, a compound that affects the activity of an RXR-LXR heterodimer is used. For example, an LXR agonist can be administered to the cell, thereby causing an increase in the expression of ABCG8 as well as other ABCs such as ABCG5. Such LXR agonists include, e.g., cholesterol as well as synthetic compounds such as Compounds A, B, C, and others. Alternatively, RXR agonists can be used. In other embodiments, nucleic acids encoding LXR or RXR can be introduced into cells of interest, thereby causing an increase in the level of LXR-RXR activity, and thereby causing an increase in ABCG8-mediated transport activity. Additional LXR agonists can be identified using assays as described in U.S. Application Serial Nos. 60/115,292, 60/124,525, Ser. No. 09/525,861, and Ser. No. 09/479,315, and in TTC Reference Nos. 018781-003010 and 018781-003310, and using any of the biochemical, genetic, or cell-based assays described herein.

Any of the above-described molecules can be used to increase or decrease the expression or activity of ABCG8, or to otherwise affect the properties and/or behavior of ABCG8 polypeptides or polynucleotides, e.g., stability, phosphorylation, kinase activity, interactions with other proteins, etc. The present compounds can thus be used to treat any of a number of diseases, including, but not limited to, sitosterolemia, atherosclerosis, hyperlipidemia, gall stones (e.g., cholesterol stones) hypercholesterolemia (e.g., familial hypercholesterolemia) coronary heart disease, HDL deficiency, nutritional deficiency, arthritis, xanthomas, and hemolytic anemia.

The present methods can also be used simply to lower the amount of cholesterol and other sterols absorbed in the diet of any mammal, to lower the amount of cholesterol retained in the liver of any mammal, and to prevent the formation of foam cells in a mammal, thereby preventing the development of the above-described diseases and conditions in any mammal. Further, such compounds can be administered specifically to one or another cell type, for example, specifically to cells lining the intestinal lumen, thereby preventing absorption of dietary cholesterol and other sterols, or specifically to macrophage cells, e.g., in the vicinity of an atherosclerotic plaque, thereby inhibiting the development of foam cells. Such cells can be targeted in any of a number of well known ways, for example by local administration of the compound, or by delivering the compound in combination with a moiety that can specifically target the compound to the cell of interest, e.g., a cell specific antibody or ligand.

A. Administration and Pharmaceutical Compositions

Administration of any of the present molecules can be achieved by any of the routes normally used for introducing a modulator compound into ultimate contact with the tissue to be treated. The modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, $17^{th}$ ed. 1985)).

The ABCG8 modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and nonaqueous solutions, isotonic sterile solutions, which can contain antioxidants, buffers, bacteriostats, and solutes that render the formulation isotonic, and aqueous and nonaqueous sterile suspensions that can include suspending agents, solubilizers, thickening agents, stabilizers, and preservatives. In the practice of this invention, compositions can be administered, for example, orally, nasally, topically, intravenously, intraperitoneally, intravesically or intrathecally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered, a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the compound at various concentrations, as applied to the mass and overall health of the subject. Administration can be accomplished via single or divided doses.

VII. Transgenic Animals

Transgenic and chimeric non-human mammals and methods for generating them are described below. The mammals are useful, inter alia, for testing the function of ABCG8 in vivo, to generate models for the study of cholesterol-associated diseases and conditions, and for the development of potential treatments for ABCG8 related diseases and conditions, such as sitosterolemia and other cardiovascular disorders.

Transgenic and chimeric non-human mammals are generated that contain cells that lack at least one functional endogenous allele for ABCG8. A "chimeric animal" includes some cells that lack the functional ABCG8 gene of interest and other cells that do not have the inactivated gene. A "transgenic animal," in contrast, is made up of cells that have all incorporated the specific modification which renders the ABCG8 gene inactive or otherwise altered. While a transgenic animal is typically always capable of transmitting the mutant ABCG8 gene to its progeny, the ability of a chimeric animal to transmit the mutation depends upon whether the inactivated gene is present in the animal's germ cells. The modifications that inactivate or otherwise alter the ABCG8 gene can include, for example, insertions, deletions, or substitutions of one or more nucleotides. The modifications can interfere with transcription of the gene itself, with translation and/or stability of the resulting mRNA, or can cause the gene to encode an inactive or otherwise altered ABCG8 polypeptide, e.g., an ABCG8 polypeptide with modified binding properties or transport activity.

The claimed methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, Calif., Ed., *Transgenic Animal Technology: A Laboratory Handbook*, Academic Press, 1994.

In preferred embodiments, transgenic mice will be produced as described in Thomas et al., (1999) *Immunol.* 163:978–84; Kanakaraj et al. (1998) *J. Exp. Med.* 187:2073–9; or Yeh et al., (1997) *Immunity* 7:715–725.

Typically, a modified ABCG8 gene is introduced, e.g., by homologous recombination, into embryonic stem cells (ES), which are obtained from preimplantation embryos and cultured in vitro. See, e.g., Hooper, ML, *Embryonal Stem Cells: Introducing Planned Changes into the Animal Germline* (Modem Genetics, v. 1), Int'l. Pub. Distrib., Inc., 1993; Bradley et al. (1984) *Nature* 309:255–258. Subsequently, the transformed ES cell is combined with a blastocyst from a non-human animal, e.g., a mouse. The ES cells colonize the embryo and in some embryos form the germ line of the resulting chimeric animal. See, Jaenisch (1988) *Science* 240:1468–1474. Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385:810–813.

Other methods for obtaining a transgenic or chimeric animal having a mutant ABCG8 gene in its genome is to contact fertilized oocytes with a vector that includes a polynucleotide that encodes a modified, e.g., inactive, ABCG8 polypeptide. In some animals, such as mice, fertilization is typically performed in vivo and fertilized ova are surgically removed. In other animals, particularly bovines, it is preferably to remove ova from live or slaughterhouse animals and fertilize the ova in vitro. See, DeBoer et al., WO 91/08216. In vitro fertilization permits the modifications to be introduced into substantially synchronous cells.

Fertilized oocytes are typically cultured in vitro until a pre-implantation embryo is obtained containing about 16–150 cells. The 16–32 cell stage of an embryo is described as a morula, whereas pre-implantation embryos containing more than 32 cells are termed blastocysts. These embryos show the development of a blastocoel cavity, typically at the 64 cell stage. The presence of a desired ABCG8 mutation in the cells of the embryo can be detected by methods known to those of skill in the art, e.g., Southern blotting, PCR, DNA sequencing, or other standard methods. Methods for culturing fertilized oocytes to the pre-implantation stage are described, e.g., by Gordon et al. (1984) *Methods Enzymol.* 101:414; Hogan et al. *Manipulation of the Mouse Embryo: A Laboratory Manual*, C.S.H.L. N.Y. (1986) (mouse embryo); Hammer et al. (1985) *Nature* 315:680 (rabbit and porcine embryos); Gandolfi et al. (1987) *J. Reprod. Fert.* 81:23–28; Rexroad et al. (1988) *J. Anim. Sci.* 66:947–953 (ovine embryos) and Eyestone et al. (1989) *J. Reprod. Fert.* 85:715–720; Camous et al. (1984) *J. Reprod. Fert.* 72:779–785; and Heyman et al. (1987) *Theriogenology* 27:5968 (bovine embryos). Pre-implantation embryos may also be stored frozen for a period pending implantation.

Pre-implantation embryos are transferred to an appropriate female resulting in the birth of a transgenic or chimeric animal, depending upon the stage of development when the transgene is integrated. Chimeric mammals can be bred to form true germline transgenic animals. Chimeric mice and germline transgenic mice can also be ordered from commercial sources (e.g., Deltagen, San Carlos, Calif.).

Other methods for introducing mutations into mammalian cells or animals include recombinase systems, which can be employed to delete all or a portion of a locus of interest. Examples of recombinase systems include, the cre/lox system of bacteriophage P1 (see, e.g., Gu et al. (1994) *Science* 265:103–106; Terry et al. (1997) *Transgenic Res.* 6:349–356) and the FLP/FRT site specific integration system (see, e.g., Dymecki (1996) *Proc. Natl. Acad. Sci. USA* 93:6191–6196). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the ABCG8 gene of interest, e.g., by using a tissue specific promoter to drive the expression of the recombinase. See, e.g., Tsien et al. (1996) *Cell* 87:1317–26; Brocard et al. (1996) *Proc. Natl. Acad. Sci. USA* 93:10887–10890; Wang et al. (1996) *Proc. Natl. Acad. Sci. USA* 93:3932–6; Meyers et al. (1998) *Nat. Genet.* 18:136–41).

The presence of any mutation in an ABCG8 gene in a cell or animal can be detected using any method described herein, e.g., Southern blot, PCR, or DNA sequencing. See, e.g., Ausubel et al., supra.

VIII. Kits

ABCG8 genes and their homologs are useful tools for a number of applications, including, but not limited to, diagnosing sitosterolemia and other cardiovascular disorders, for forensics and paternity determinations, and for treating any of a large number of ABCG8 associated diseases. ABCG8 specific reagents that specifically hybridize to ABCG8 nucleic acids, such as ABCG8 probes and primers, and ABCG8 specific reagents that specifically bind to or modulate the activity of an ABCG8 protein, e.g., ABCG8 antibodies or other compounds can thus be provided in a kit for the practice of any of the applications described herein.

Nucleic acid assays for the presence of DNA and RNA for a ABCG8 polynucleotide in a sample include numerous techniques known to those skilled in the art, such as Southern analysis, Northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, an ABCG8 protein can be detected with the various immunoassay techniques described above. The test sample is typically compared to both a positive control (e.g., a sample expressing a recombinant ABCG8 protein) and a negative control.

The present invention also provides kits for screening for modulators of ABCG8 proteins or nucleic acids. Such kits can be prepared from readily available materials and reagents. For example, such kits can comprise any one or more of the following materials: ABCG8 nucleic acids or proteins, reaction tubes, and instructions for testing ABCG8 activity. Optionally, the kit can contain a biologically active ABCG8 protein. A wide variety of kits and components can be prepared according to the present invention, depending upon the intended user of the kit and the particular needs of the user.

IX. Examples

As explained above, it was hypothesized that sitosterolemic patients might have defects in other genes that limit cholesterol absorption and that the expression of these genes would be regulated by LXR. To test this idea DNA microarrays were used to search for mRNAs that are induced by the LXR agonist T091317 in mouse liver and intestine (Repa, et al., *Science* 289:1524 (2000). Total RNA was prepared from the liver, intestine and kidney of C57BL/6 mice treated with the LXR agonist T091317 (50 mg/kg). Duplicate RNA samples were labeled with two fluorescence dyes and hybridized to mouse GEM1 microarrays (performed at Incyte Genomics, Inc.). Data analysis revealed the relative expression levels of 8734 genes in tissues from the treated versus the untreated mouse tissues. A transcript corresponding to a murine EST (AA237916) was induced ~2.5-fold in the livers and intestines of treated mice. This EST resembled three Drosophila genes that encode ABC half-transporters (brown, scarlet and white) expressed in the pigmentary cells of the eye (Sullivan, et al., *J. Exp. Zool.* 188:225 (1974); Bingham, et al., *Cell* 25:693 (1981); C. Higgins, *Annu. Rev. Cell Biol.* 8:67 (1992)). These ABC half-transporters contain six membrane spanning domains and form two types of heterodimers that transport guanine (brown/white) or tryptophan (scarlet/white). Since a human homolog of white (ABCG1) is implicated in cellular cholesterol efflux from macrophages (Klucken, et al., *Proc. Natl. Acad. Sci. U.S.A.* 97:817 (2000); Venkateswatan, et al., *J. Biol. Chem.* 12:147000 (2000)), we reasoned that the LXR-induced protein encoded by AA237916 might be involved in sterol trafficking in liver and intestine, and hence this gene was a candidate for the defect in sitosterolemia.

A full-length cDNA corresponding to AA237916 was isolated from a mouse liver cDNA library (Origene), and this sequence was used to identify a human ortholog in the GENBANK EST database (T86384). A full-length human sequence was obtained by iterative EST database searches and by cloning from human liver cDNA libraries (Origene and Clontech). The human cDNA predicts a 651 amino acid protein (FIG. 1C) that shares 82% sequence identity with the mouse sequence (data not shown). Following the standard system of nomenclature in the ABC transporter field, this protein has been named ABCG5. The amino terminal half of ABCG5 contains the ATP-binding motifs (Walker A and B motifs) and an ABC transporter signature motif (C motif), while the carboxyl terminal region is predicted to contain six transmembrane (TM) segments (FIG. 1B) (C. Higgins, *Annu. Rev. Cell Bid.* 8:67 (1992) Walker et al., *Embo. J.* 1:945 (1982) Jones et at., *Biochem.* 33:3038 (1994)). A human EST clone (Unigene T93792) from ABCG5 mapped to chromosome 2p21 between markers D2S177 and D2S119 and the map position was confirmed using a radiation hybrid panel. Chromosomal localization of ABCG5 was confirmed using primers derived from exon 7 of ABCG5 to amplify a gene-specific fragment from the TNG panel of radiation hybrids from Stanford Human Genome Center (Research Genetics, Inc). The result was submitted to the RH Server URL address: http file type, www host server, domain name-shgc.stanford.edu), which linked ABCG5 to SHGC 14952, which is between markers D2S177 and D2SL 19. Patel and colleagues previously mapped the human sitosterolemia gene to this same region of chromosome 2 in ten independent sitosterolemic families (Patel et at., *J. Clin. Invest.* 102:1041 (1998)).

The structure of the human ABCG5 gene was characterized by analysis of a bacterial artificial chromosome (BAC) clone that contained the entire gene (FIG. 1A). The gene spans ~28 kb and has 13 exons and 12 introns. The last 3 exons of ABCG5 were contained in the GenBank sequence entry AC011242 and were further confirmed by PCR analysis from human genomic DNA. The remaining 10 exon/intron boundaries were determined using PCR and cDNA primers to amplify the exon sequences and the intron/exon boundaries using genomic DNA and cDNA primers followed by sequence analysis. The coding sequences and consensus splicing sequences were amplified from genomic DNA by PCR and sequenced in nine unrelated subjects with sitosterolemia (see, Table 2, infra). A sitosterolemic patient from Hong Kong (proband 9) was heterozygous for a transition mutation (CGA to TGA) in codon 408 that introduced a premature stop codon between TM1 and TM2. This mutation was not present in 65 normolipidemic individuals, including 40 Chinese subjects. No other potential disease-causing mutations were identified in ABCG5. A transversion in codon 604 that substituted a glutamic acid for glutamine (Q604E) in the loop between TM5 and TM6 was found in five sitosterolemic probands, but was also present in 23% of the alleles from normolipidemic Caucasians (n=50).

ESTs in the public database. Eleven of the 13 exons of the new gene, which was named ABCG8, were identified in the databases and the remaining two exons were identified by sequencing PCR-amplified cDNAs from human hepatic polyA+mRNA. ABCG8 shares ~28% amino acid identity with ABCG5 (FIG. 1C). Its sequence is most similar to ABCG1, which resembles the Drosophila white gene (Bingham et al., *Cell*, 25:693 (1981)).

TABLE 2[1, 2]

| Subject (age) | Ethnicity | MutantAlleles | Nucleotide Change | Amino Acid Change(s) | Comments | Ref. |
|---|---|---|---|---|---|---|
| 1 (8 y) | German/ Swiss | ABCG8 ABCG8 | c.1083G>A c.1083G>A | W361Stop W361Stop | Original case. C = 195 mg/dl | 1 |
| 2 (13 y) | Amish | ABCG8 ABCG8 | c.1720G>A c.1720G>A | G574R G574R | 13-year-old died of CAD | 34 |
| 3 (8 mo) | Caucasian American | ABCG8 ABCG8 | c.1083G>A c.1974C>G | W361Stop Y658Stop | C fell from 800 to 151 mg/dl on low C diet | |
| 4 (<10 y) | Chinese | ABCG8 ABCG8 | c.788G>A c.691A>C | R263Q P231T | C = 556 mg/dl | |
| 5 (5 y) | Caucasian American | ABCG8 ABCG8 | c.1083G>A c.1234C>T | W361Stop R412Stop | C fell from 375 to 201 mg/dl on low C diet | 5 |
| 6 (2 y) | Caucasian American | ABCG8 ? | c.1787T>G ? | L596R ? | C fell from 753 to 106 mg/dl on low C diet | 32 |
| 7 | Mexican-American | ABCG8 ABCG8 | 1234C>T 547-delete | R412Stop 191Stop | LDL-C fell from 380 to 200 mg/dl | |
| 8 (3.5 y) | Caucasian N. Zealander | ABCG8 ? | c.1083G>A ? | W361Stop ? | C fell from 718 to 127 mg/dl on low C diet | 31 |
| 9 (<10 y) | Chinese | ABCG5 ? | c.1222C>T ? | R408 Stop ? | C = 620 mg/dl | |

[1]Molecular defects in nine unrelated individuals with sitosterolemia. Genomic DNA was extracted from cultured fibroblasts or lymphoblasts from the proband or another family member with sitosterolemia (Hobbs, et al, Hum. Mutat. 1:445 (1992)). All subjects had elevated plasma sitosterol levels (except proband 6 in which plasma sitosterol level were not measured). The age at the time of diagnosis or at the first appearance of xanthomas is provided (when available).
The exons and flanking splice site consensus sequences were screened for sequence variations using SSCP and dideoxy-sequencing (Walker, et al., Embo. J. 1:945 (1982)). None of the mutations were found in 100 alleles from normolipidemic controls. The nucleotides are numbered consecutively starting at the A of the initiation condon ATG. Plasma cholesterol levels were obtained from referring physicians or from publications.
[2]Abbreviations: y, years; C, fasting plasma cholesterol level; ref., reference; CAD, coronary artery disease; G, Gly; Q, Gln; L, Leu, P, Pro; R, Arg; T, Thr; W, Trp; Y, Tyr.

Genes encoding members of the ABC transporter family are often clustered in the genome (Le Saux et at., *Nat. Genet.* 25:223 (2000)). Since only a single ABCG5 mutation was identified in our collection of nine sitosterolemic probands, the public and Celera genome sequences were searched for other ABC transporters adjacent to ABCG5. An EST (T84531) that shared weak homology with the Drosophila white gene was identified and expanded using exons predicted by the computer program GENSCAN. The 3'-end of ABCG5 was located on BAC RP11-489K22, which had been partially sequenced, but no other ABC transporters were identified on this BAC. A BAC end sequences (BES) in the Genome Survey Sequence database that was located on BAG RP11-489K22 was used to search the Celera Human Fragments database. The public and Celera database were used to assemble most of the genomic sequences in the region, resulting in the identification of EST T84531, which shared weak homology with the drosophila white gene (Repa et at., *Science* 289:1524 (2000)). The GENSCAN Web Server URL address: http file type, www host server, domain name genes.mit.edu/GENSCAN.html) was used to identify additional exons within this gene. The sequence of the ~30 kb region was assembled (excluding three gaps) using the Celera Human Fragments database and mouse ESTs in the public database. Eleven of the 13 exons of the new gene, which was named ABCG8, were identified in the databases and the remaining two exons were identified by sequencing PCR-amplified cDNAs from human hepatic polyA+mRNA. ABCG8 shares ~28% amino acid identity with ABCG5 (FIG. 1C). Its sequence is most similar to ABCG1, which resembles the Drosophila white gene (Bingham et al., *Cell*, 25:693 (1981)).

The translational start sites of ABCG8 and ABCG8 are separated by only 374 basepairs and the two genes are arranged in a head to head orientation (FIG. 1A). Both genes contain a translation initiation codon with an upstream in-frame stop codon. The close proximity and opposite orientation of ABCG5 and ABCG8 suggest that the two genes have a bidirectional promoter and share common transcriptional and regulatory elements (Ikeda, et al., *Biochem. Biophys. Res. Commun.* 273:1063 (2000); Pollner, et al, *FEBS Lett.* 405:31 (1997)). Other gene pairs with bi-directional promoters form functional complexes (Pollner, et al, *FEBS Lett.* 405:31 (1997)), as is thought to be the case for ABCG5 and ABCG8.

The predicted intron-exon boundaries of human ABCG8 were confirmed by DNA sequencing. The single strand conformation polymorphism technique was used to screen the exons and flanking intron sequences of ABCG8 in the nine sitosterolemic subjects (see, Table 2, supra) (Orita, et al., *Genomics* 5:874 (1989); Hobbs, et al, *Hum. Mutat.* 1:445 (1992)). DNA sequencing of abnormally-migrating fragments revealed six different mutations (see, Table 2 and FIG. 1B). The first patient to be described with sitosterolemia (proband 1) was homozygous for a nonsense mutation (c.1083G>A) in exon 7 (FIG. 1B) that introduced a premature termination signal codon at codon 361, terminating the protein prior to TM1 (Bhattacharyya, et al., *J. Clin. Invest.* 53:1033 (1974)). Three other unrelated Caucasian sitosterolemic subjects (probands 3, 5 and 8) were heterozygous for the same mutation (Salen, et al., *J. Lipid Res.* 33:945 (1992); Nye, et. al, *N. Z. Med. J.* 101:418 (1988); Stell and Sprecher, *Top. Clin. Nutr.* 5:63 (1990)). One of these probands (proband 5) were originally given the diagnosis of pseudohomozygous familial hypercholesterolemia, an autosomal recessive disorder characterized by hypercholesteromia, tendon xanthomas and exquisite sensitivity to dietary cholesterol (Morganroth, et al., *J. Pediatr.* 85:639 (1974); Stell and Sprecher, *Top. Clin. Nutr.* 5:63 (1990)). Many of the patients originally diagnosed with pseudohomozygous FH were subsequently found to have sitosterolemia, as was the case with this patient and proband 6 (Morganroth, et al., *J. Pediatr.* 85:639 (1974); Stell and Sprecher, *Top. Clin. Nutr.* 5:63 (1990)). Proband 3 was heterozygous for another nonsense mutation in exon 13 that introduced a stop codon 15 residues from the carboxyl terminus of ABCG8. The resulting protein would lack part of the last predicted transmembrane domain, and the short cytoplasmic domain, which contains a cluster of positively charged residues that may be important in positioning these proteins in the membrane (Ewart, et al., *J. Biol. Chem.* 269:10370–7 (1994)).

Two missense mutations identified in ABCG8 produced nonconservative amino acid changes in residues that are conserved between the humans and mouse proteins (data not shown) as well as in ABCG5. One Chinese patient (proband 4) was heterozygous for a missense mutation in exon 6 in codon 263 (R263Q). An Amish subject with sitosterolemia was homozygous for a missense mutation (G574R) in a residue that is conserved in mouse and human ABCG8. Genomic DNA was available from an additional three of the four living affected family members in this large Amish pedigree (Kwiterovich, Jr., et al., *Lancet* 1:466 (1981) Beaty, et al., *Am. J Hum. Genet.* 38:492 (1981)) and these individuals were homozygous for this same missense mutation (data not shown). A third nonconservative missense mutation was an arginine substitution for a leucine in codon 596. The corresponding sequence in ABCG5 is another nonpolar amino acid, glutamine. None of these three missense mutations were identified in 100 alleles from ethnically-matched normolipidemic subjects, which is consistent with these being disease-causing mutations. A common polymorphism (Y54C) with an allele frequency of 23% in control subjects (n=100 alleles) was also identified in ABCG8.

Thus, two mutant alleles at the ABCG8 locus have been identified in four of the nine sitosterolemic patients. Four patients had a single mutant allele in ABCG8 and one patient had a single mutant allele in ABCG5. The identification of multiple different ABCG8 mutations in subjects with sitosterolemia, including nonsense mutations that appear incompatible with protein function, provides strong evidence that sitosterolemia is caused by defects in this gene. It also seems likely that the mutation found in ABCG5 causes sitosterolemia, although it is thought that additional mutations in this gene may also be possible. It is possible that some mutations causing sitosterolemia were not detected by SSCP or because they were located in sequences not screened in this study, including regulatory sequences or those required for mRNA processing. Alternatively, it remains possible that mutations in other genes (perhaps other ABC transporters) within the genomic interval mapped by Patel, et al. (Patel, et al., *J. Clin. Invest.* 102:1041 (1998)) can cause sitosterolemia when present in combination with mutations in ABCG5 or ABCG8.

Figure 2:
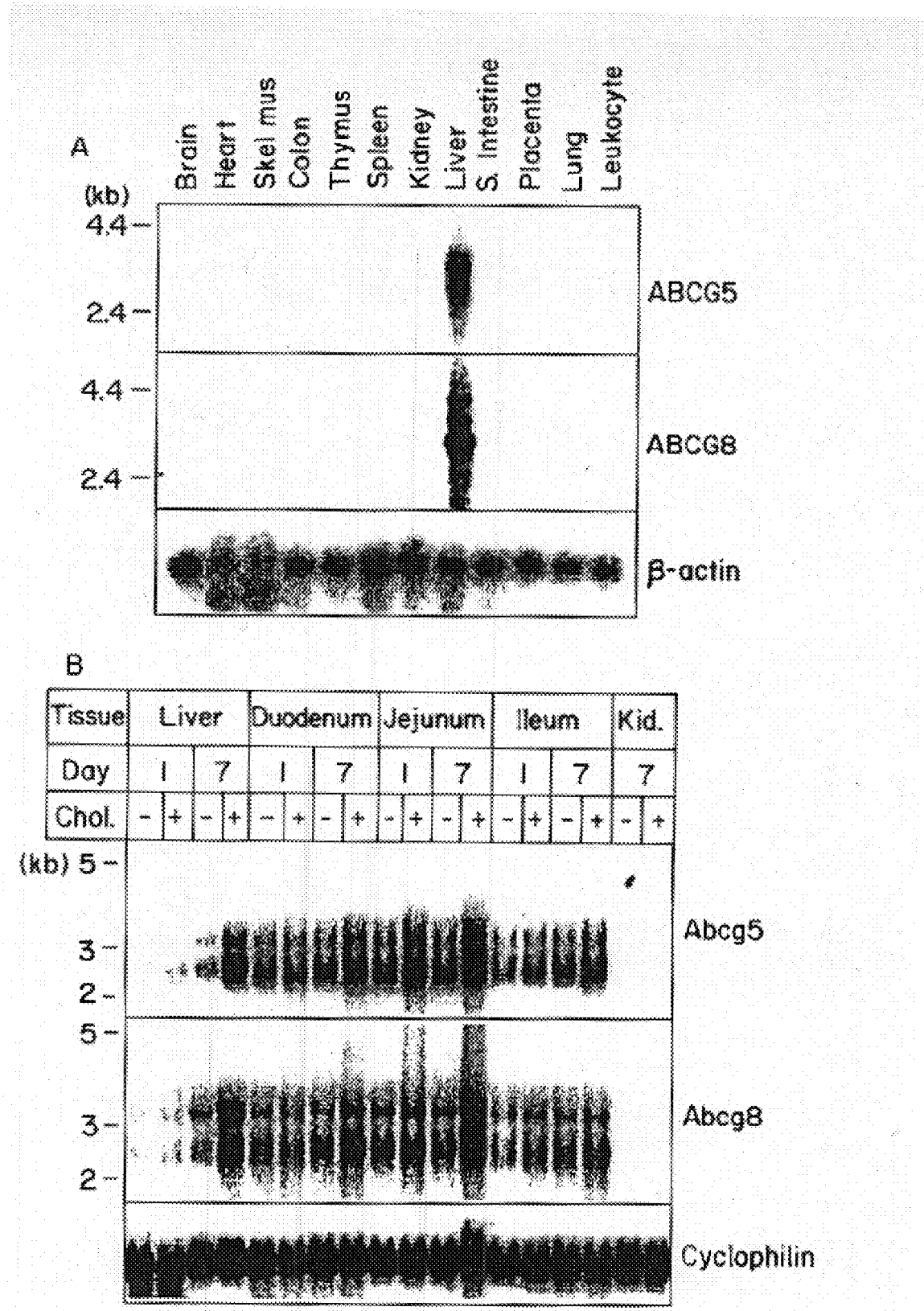
FIG. 2. Expression of ABCG5 and ABCG8 in human tissues (A) and the effect of cholesterol feeding on levels of ABCG5 and ABCG8 mRNAs in mouse liver and intestines (B). (A) Northern blot analysis of human tissues. The coding sequence of ABCG5 and ABCG8 were amplified from liver polyA$^+$RNA (Clontech) and the fragments were cloned into the plasmid vector pGEM-T (Promega). The coding region of the cDNA was amplified and the fragment radiolabeled (Megaprime DNA Labeling System, Amersham) prior to incubation with the blot in Rapid-hyb buffer ($1\times10^6$ cpm/ml) (Amersham). The blot was washed and subjected to autoradiography for 18 h using Kodak X-OMAT-blue film (Jokinen, et al., J. Biol. Chem. 269:26411 (1994)). The results were identical when probes generated from the 3' untranslated regions of both cDNAs were used. (B) Cholesterol feeding-induces coordinate increases in levels of ABCG5 and ABCG8 mRNA. Seven-week-old male mice (129S3/SvImj) were fed powdered chow (Harlan Teklad Rodent Diet) in the absence or presence of cholesterol (2%, w/v). Mice were killed after one or seven days in the light phase of the cycle. Total RNA was isolated using RNA-STAT (TelTest) from the liver and three equal segments of the small intestine (duodenum, jejunum and ileum). The tissue RNAs were pooled from three animals and aliquots (15 μg) used to make duplicate northern blots (Hobbs, et al, Hum. Mutat. 1:445 (1992)). The mouse cDNAs for ABCG5 and ABCG8 were used as probes. Cyclophilin was used as an internal standard. The results were identical when probes generated from the 3' untranslated regions of both cDNAs were used.

To determine if ABCG5 and ABCG8 are regulated coordinately, the tissue distributions of their mRNAs in humans and mice were examined, and their responses to cholesterol feeding in mice. In humans, liver was the major site of expression of both genes (FIG. 2A). For both ABCG5 and ABCG8, one major transcript predominated, but other mRNAs were visible by RNA blotting. Additional studies will be required to determine the identity of these transcripts, which presumable result from alternative splicing of differential polyadenylation. RNAs of the same sizes as those seen in the liver were seen in the small intestine on a longer exposure times (data not shown). Transcripts for both ABCG5 and ABCG8 could be PCR-amplified from human intestinal mRNA, but not from human cholesterol-loaded differentiated monocytes (THP-1 cells) (data not shown). In mice, Abcg5 and Abcg8 were expressed at higher levels in the intestine than in the liver, although the relative amounts of expression in these two tissues may be strain- and sex-specific (data not shown).

If ABCG5 and ABCG8 protect against the accumulation of sterols, then their expression levels would be predicted to increase with cholesterol feeding. To test this hypothesis, mice were fed a high cholesterol diet (2%) and killed after 1, 7 or 14 days. The mRNA levels of both genes increased ~2-fold in intestine and much more markedly in liver within one week of initiation of the high cholesterol diet (FIG. 2B). These changes were maintained at two weeks (data not shown). As expected, the plasma levels of cholesterol did not significantly change in the cholesterol-fed mice (from 95 mg/dl versus 93 mg/dl) since mice rapidly and efficiently convert dietary cholesterol into bile acids and excrete both cholesterol and bile acids into the bile (Russell and Setchell, *Biochem.* 31:4737 (1992)). LXR plays a central role in this regulated process by increasing the expression of multiple hepatic genes that promote bile acid synthesis and biliary secretion (Repa, et al., *Science* 289:1524 (2000)). The ligands for LXR include hydroxylated sterols that are derived from cholesterol (Janowski, et al., *Nature* 383:728 (1996); Janowski, et al, *Proc. Natl. Acad. Sci. U.S.A.* 96:266 (1999)). Since ABCG5 is induced by an LXR agonist, it is possible that dietary sterols induce these genes through LXR.

The aforementioned data indicate that ABCG5 and ABCG8 are putative ABC half-transporters that may partner to generate a functional protein. The juxtaposition of these two genes on chromosome 2, the coordinate regulation of their mRNAs in the liver and intestine with cholesterol feeding, and the observation that mutations in either gene are associated with sitosterolemia, suggest that these two proteins form a functional complex that mediates efflux of dietary cholesterol from the intestine, and thus protects humans from sterol overaccumulation. This protection is especially important in Western societies that consume high cholesterol diets. Loss of function of these proteins causes sitosterolemia. It seems possible that subtle defects in these proteins or in their regulation may underlie the variable responses of individuals to high cholesterol diets.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An isolated nucleic acid encoding an ABCG8 polypeptide, said polypeptide comprising an amino acid sequence that is at least 80% identical to the full-length of an amino acid sequence as set forth in SEQ ID NO: 8, wherein said polypeptide exhibits sterol transport activity.

2. The nucleic acid of claim 1, wherein said polypeptide comprises an amino acid sequence having 100% identity to the full length of SEQ ID NO: 8.

3. The nucleic acid of claim 1, wherein said polypeptide is at least 95% identical to an amino acid sequence as set forth in SEQ ID NO: 8.

4. The nucleic acid of claim 1, wherein said polypeptide is at least 90% identical to an amino acid sequence as set forth in SEQ ID NO: 8.

5. The nucleic acid of claim 1, wherein said polypeptide is at least 85% identical to an amino acid sequence as set forth in SEQ ID NO: 8.

6. The nucleic acid of claim 1, wherein said nucleic acid comprises a nucleotide sequence having 100% identity to the full-length of SEQ ID NO: 7.

7. The nucleic acid of claim 1, wherein said nucleic acid comprises a nucleotide sequence at least 95% identical to a sequence as set forth in SEQ ID NO: 7.

8. The nucleic acid of claim 1, wherein said nucleic acid comprises a nucleotide sequence at least 90% identical to a sequence as set forth in SEQ ID NO: 7.

9. The nucleic acid of claim 1, wherein said nucleic acid comprises a nucleotide sequence at least 85% identical to a sequence as set forth in SEQ ID NO: 7.

10. The nucleic acid of claim 1, wherein said nucleic acid hybridizes under the following moderately stringent hybridization conditions:
   (1) hybridization at 37° C. in a hybridization buffer comprising 40% formamide, 1 M NaCl, and 1% SDS and;
   (2) washing at 45° C. in a wash solution comprising 1×SSC;
to a nucleic acid comprising a nucleotide sequence as set forth in SEQ ID NO:7.

11. The nucleic acid of claim 1, wherein said nucleic acid hybridizes under the following stringent hybridization conditions:
   (1) hybridization at 42° C. in a hybridization buffer comprising 50% formamide, 5×SSC, and 1% SDS and;
   (2) washing at 65° C. in a wash solution comprising 0.2×SSC and 0.1% SDS;
to a nucleic acid comprising a nucleotide sequence as set forth in SEQ ID NO:7.

12. The nucleic acid of claim 1, wherein said nucleic acid comprises a conserved exon sequence selected from the group consisting of CTGGTAGGTGAGATCTCTGAC-CTCCAGAGTGTTGGACTGTTGGACTGAC-CACTGTAG GTGAAGTACAGACTGTTGTCACTTTC-CCGAGGAGAACAAGCTTCCTGGAGGCC (bp 3–104 of SEQ ID NO: 9) and CGAAGCATCCTGAAGTACAGTC-CCATTCCACAGCTGGGTCTCTTCTTTTGGTTTTCTC AGCAT (bp 3436–5005 of SEQ ID NO: 9).

13. The nucleic acid of claim 1, wherein said polypeptide forms a dimer with a second ABC polypeptide, and wherein said dimer exhibits sterol transport activity.

14. The nucleic acid of claim 13, wherein said dimer is a heterodimer.

15. The nucleic acid of claim 14, wherein said second ABC polypeptide is an ABCG5 polypeptide.

16. The nucleic acid of claim 13, wherein said sterol is cholesterol.

17. The nucleic acid of claim 1, wherein said nucleic acid is from a mouse or a human.

18. The nucleic acid of claim 1, wherein said nucleic acid is expressed in the intestine or in the liver in the presence of an LXR agonist.

19. The nucleic acid of claim 1, wherein said nucleic acid is expressed in a tissue selected from the group consisting of liver, jejunum, ileum, and duodenum.

20. An expression cassette comprising the nucleic acid of claim 1 operably linked to promoter.

21. An isolated cell comprising the expression cassette of claim 20.

22. A method of making an ABCG8 polypeptide, the method comprising:
 (i) introducing a nucleic acid of claim 1 into a host cell or cellular extract; and
 (ii) incubating said host cell or cellular extract under conditions such that said ABCG8 polypeptide is expressed in the host cell or cellular extract.

23. The method of claim 22, further comprising recovering the ABCG8 polypeptide from the host cell or cellular extract.

24. An isolated ABCG8 polypeptide, said polypeptide comprising an amino acid sequence that is at least 80% identical to the full-length of an amino acid sequence as set forth in SEQ ID NO: 8 wherein said polypeptide exhibits sterol transport activity.

25. The polypeptide of claim 24, wherein said polypeptide is 100% identical to an amino acid sequence as set forth in SEQ ID NO: 8.

26. The polypeptide of claim 24, wherein said polypeptide is at least 95% identical to an amino acid sequence as set forth in SEQ ID NO: 8.

27. The polypeptide of claim 24, wherein said polypeptide is at least 90% identical to an amino acid sequence as set forth in SEQ ID NO: 8.

28. The polypeptide of claim 24, wherein said polypeptide is at least 85% identical to an amino acid sequence as set forth in SEQ ID NO: 8.

29. The polypeptide of claim 24, wherein said polypeptide forms a dimer with a second ABC polypeptide, and wherein said dimer exhibits sterol transport activity.

30. The polypeptide of claim 29, wherein said dimer is a heterodimer.

31. The polypeptide of claim 29, wherein said sterol is cholesterol.

32. The polypeptide of claim 30, wherein said second ABC polypeptide is an ABCG5 polypeptide.

33. The polypeptide of claim 24, wherein said polypeptide is from a mouse or a human.

34. The polypeptide of claim 24, wherein said polypeptide is expressed in the intestine or in the liver in the presence of an LXR agonist.

35. The polypeptide of claim 24, wherein said polypeptide is expressed in a tissue selected from the group consisting of liver, jejunum ileum, and duodenum.

* * * * *